(12) United States Patent
Smith et al.

(10) Patent No.: US 6,960,601 B2
(45) Date of Patent: Nov. 1, 2005

(54) PREPARATION AND USE OF IMIDAZOLE DERIVATIVES FOR TREATMENT OF OBESITY

(75) Inventors: Roger A. Smith, Madison, CT (US); Stephen J. O'Connor, Guilford, CT (US); Stephan-Nicholas Wirtz, Wuppertal (DE); Wai C. Wong, Hamden, CT (US); Soongyu Choi, Trumbull, CT (US); Harold C. E. Kluender, Trumbull, CT (US); Ning Su, Hamden, CT (US); Gan Wang, Wallingford, CT (US); Furahi Achebe, West Haven, CT (US); Shihong Ying, Orange, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 107 days.

(21) Appl. No.: 10/255,049

(22) Filed: Sep. 24, 2002

(65) Prior Publication Data

US 2004/0063691 A1 Apr. 1, 2004

Related U.S. Application Data

(60) Provisional application No. 60/324,473, filed on Sep. 24, 2001.

(51) Int. Cl.[7] .................... C07D 233/90; A61K 31/445
(52) U.S. Cl. ...................................... 514/326; 546/210
(58) Field of Search .......................... 546/210; 514/326

(56) References Cited

U.S. PATENT DOCUMENTS

| | | | |
|---|---|---|---|
| 4,924,000 A | 5/1990 | Hesse et al. ............... 548/343 |
| 5,091,405 A | 2/1992 | Stevenson et al. ........... 514/403 |
| 5,164,406 A | 11/1992 | Helman et al. ............. 514/357 |
| 5,179,210 A | 1/1993 | Ebel ........................ 548/335.1 |
| 5,519,143 A | 5/1996 | Harris ....................... 548/253 |
| 5,550,147 A | 8/1996 | Matsuo et al. .............. 514/406 |
| 5,565,577 A | 10/1996 | Mokhallalati et al. ... 548/333.5 |
| 5,616,601 A | 4/1997 | Khanna et al. ............. 514/399 |
| 5,624,941 A | 4/1997 | Barth et al. ................. 514/326 |

FOREIGN PATENT DOCUMENTS

| | | |
|---|---|---|
| DE | 140966 | 4/1980 |
| WO | 9314082 | 7/1993 |
| WO | 9603388 | 2/1996 |
| WO | 9827065 | 6/1998 |
| WO | 9932454 | 7/1999 |
| WO | 0069848 | 11/2000 |
| WO | 0069849 | 11/2000 |
| WO | 0140207 | 6/2001 |
| WO | 02064136 | 8/2002 |
| WO | 03027076 | 4/2003 |
| WO | WO 2003027076 A2 * 4/2003 ......... C07D/233/90 |

OTHER PUBLICATIONS

Papadopoulos, Reactions of Imidazoles with Isocyanates at Elevated Temperatures, J. Org. Chem. 42:39253929, 1977.
Ueda et al., A Novel Ring Transformation of 5–Acylaminouracils and 5–Acylaminopyrimidin–4(3H)–ones into Imidazoles, Tetrahedron Lett. 29:4607–4610, 1988.
Ueda et al., Synthesis and in vitro Antibacterial Activity of new Semi–Synthetic Noviosylcoumarin Antibiotics: Chemical Modification at the C–3 Ester, Bioorg Med. Chem. Lett. 4:1623–1628, 1994.
Matsuura et al., Synthesis of 1H–Imidazoles by the Simple Ring Transformation of 5–Acylaminouracils and 5–Acylaminopyrimidin–4(3H)–ones, J. Chem. Soc. Perkin Trans. 1:2821–2826, 1991.
Khanna et al., 1,2–Diarylimidazoles as Potent, Cyclooxygenase–2 Selective, and Orally Active Antiinflammatory Agents, J. Med. Chem. 40:1634–1647, 1997.

* cited by examiner

*Primary Examiner*—James O. Wilson
*Assistant Examiner*—Jason H. Johnsen
(74) *Attorney, Agent, or Firm*—Susan M. Pellegrino

(57) ABSTRACT

This invention relates to substituted imidazole derivatives which have been found to suppress appetite and induce weight loss. The invention also provides methods for synthesis of the compounds, pharmaceutical compositions comprising the compounds, and methods of using such compositions for inducing weight loss and treating obesity and obesity-related disorders.

8 Claims, No Drawings

PREPARATION AND USE OF IMIDAZOLE DERIVATIVES FOR TREATMENT OF OBESITY

This application claims benefit of U.S. Provisional Application Ser. No. 60/324,473, filed Sep. 24, 2001, the contents of which are incorporated herein by reference in their entirety.

FIELD OF THE INVENTION

This invention relates to the field of pharmaceuticals, in particular to the field of obesity treatment. More specifically, it relates to certain imidazole compounds which are useful in the treatment of obesity and obesity-related disorders, and as weight-loss and weight-control agents.

BACKGROUND OF THE INVENTION

Obesity, which is defined as an excess of body fat relative to lean body mass, is a well-established risk factor for a number of potentially life-threatening diseases such as atherosclerosis, hypertension, diabetes, stroke, pulmonary embolism, sleep apnea, and cancer. Furthermore, it complicates numerous chronic conditions such as respiratory diseases, osteoarthritis, osteoporosis, gall bladder disease, and dyslipidemias. The enormity of this problem is best reflected in the fact that death rates escalate with increasing body weight. More than 50% of all-cause mortality is attributable to obesity-related conditions once the body mass index (BMI) exceeds 30 kg/m$^2$, as seen in 35 million Americans (Lee, JAMA 268:2045–2049, 1992). By contributing to greater than 300,000 deaths per year, obesity ranks second only to tobacco smoking as the most common cause of potentially preventable death (McGinnis, JAMA 270:2207–2212, 1993). Accompanying the devastating medical consequences of this problem is the severe financial burden placed on the health care system in the United States. It is estimated that 30–50% of the middle-age population may be considered as obese (Kuczmarski et al., JAMA 272:205–211, 1994). The economic impact of obesity and its associated illnesses from medical expenses and loss of income are reported to be in excess of $68 billion/a year (Colditz, Am. J. Clin. Nutr. 55:503S–507S, 1992). This figure does not include the greater than $30 billion per year spent on weight loss foods, products, and programs (Wolf, Pharmacoeconomics. 5:34–37, 1994).

The accumulation or maintenance of body fat bears a direct relationship to caloric intake. Comprehensive treatment programs, therefore, focused on behavior modifications to reduce caloric intake and increase physical activity using a myriad of systems. These methods have limited efficacy and are associated with recidivism rates exceeding 95% (NIH Technology Assessment Conference Panel, Ann. Intern. Med. 119:764–770, 1993).

Obesity has also been treated by administering specific agents, for example, anorectic agents, to obese subjects. However, anorectic agents such as dextroamphetamine, the combination of the non-amphetamine drugs phentermine and fenfluramine (Phen-Fen), and dexfenfluramine (Redux) alone, are associated with serious side effects. Indigestible materials such as olestra (OLEAN®, mineral oil or neopentyl esters (see U.S. Pat. No. 2,962,419)) have been proposed as substitutes for dietary fat. Garcinia acid and derivatives thereof have been described as treating obesity by interfering with fatty acid synthesis. Swellable crosslinked vinyl pyridine resins have been described as appetite suppressants via the mechanism of providing non-nutritive bulk (see, e.g., U.S. Pat. No. 2,923,662).

Surgical interventions, such as gastric partitioning procedures, jejunoileal bypass, and vagotomy, have also been developed to treat severe obesity (Greenway, Endo. Metab. Clin. N. Amer. 25:1005–1027, 1996). Although these surgical procedures are somewhat more effective in the long run, the acute risk benefit ratio has reserved these invasive procedures for morbidly obese patients according to the National Health Institutes (NIH) consensus conference on obesity surgery (BMI>40 kg/m$^2$) (NIH Conference, Ann. Intern. Med. 115:956–961, 1991). Therefore, this approach is not an alternative for the majority of overweight patients unless and until they become profoundly obese and are suffering the attendant complications.

Thus, new methods and compositions that promote weight-loss are urgently needed.

SUMMARY OF THE INVENTION

The present invention provides substituted imidazole derivatives which have been found to suppress appetite and induce weight loss in laboratory animals. The invention also provides methods for synthesis of the compounds, pharmaceutical compositions comprising the compounds, and methods of using such compositions for inducing weight loss and treating obesity and obesity-related disorders.

DETAILED DESCRIPTION OF THE INVENTION

The invention relates to substituted imidazole derivatives that have utility in the treatment of obesity, said derivatives having Formula I

(I)

wherein
R$^1$ and R$^2$ are identical or different and are selected from
  a phenyl group optionally substituted with one or more halogen, (C$_1$–C$_6$)alkyl, (C$_1$–C$_6$)alkoxy, trifluoromethyl, cyano, nitro, (C$_1$–C$_6$)alkyl sulfonyl, (C$_1$–C$_6$)alkyl sulfonyl-amino, (C$_1$–C$_6$)alkyl carbonyl-amino, (C$_1$–C$_6$) alkyl amino-carbonyl-amino, or phenyl,
  (C$_2$–C$_6$)alkyl,
  cyclohexyl optionally substituted with (C$_1$–C$_6$)alkyl, (C$_1$–C$_6$)alkoxy, trifluoromethyl, cyano, or with one or more fluorine,
  1-naphthyl or 2-naphthyl optionally substituted with halogen, (C$_1$–C$_6$)alkyl, (C$_1$–C$_6$)alkoxy, trifluoromethyl, or cyano,
  benzyl optionally substituted on the phenyl ring with one or more halogen, (C$_1$–C$_6$)alkyl, (C$_1$–C$_6$)alkoxy, trifluoromethyl, or cyano,
  a 5- to 10-membered saturated or unsaturated heterocyclic radical optionally substituted with fluorine, (C$_1$–C$_6$)alkyl, (C$_1$–C$_6$)alkoxy, trifluoromethyl, or cyano, and
  a 5- to 10-membered aromatic monocyclic or bicyclic heterocyclic radical optionally substituted with one or more halogen, (C$_1$–C$_6$)alkyl, (C$_1$–C$_6$)alkoxy, trifluoromethyl, cyano, nitro, or phenyl;
R$^3$ is hydrogen, (C$_1$–C$_6$)alkyl, benzyl, chloro, or bromo;

X is

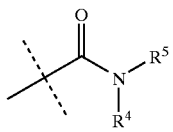

where $R^4$ is hydrogen or $(C_1-C_6)$alkyl;
$R^5$ is selected from
$(C_2-C_9)$alkyl or $(C_7-C_{11})$bicycloalkyl, each of which may optionally be substituted with one or more phenyl, hydroxy, benzyloxy, $(C_1-C_6)$alkoxy, $(C_1-C_6)$alkyl-amino, bis[$(C_1-C_3)$alkyl]-amino, 1-piperidinyl, 1-pyrrolidinyl, 2,3-dihydro-1,4-benzodioxin-2-yl, hydroxy-substituted $(C_1-C_6)$alkyl, or fluorine,
benzyl, 2-phenyl-ethyl, benzocyclohexyl or benzocyclopentyl, each of which may optionally be substituted on one of the alkyl carbons with hydroxy, benzyloxy, or hydroxy $(C_1-C_6)$alkyl, and optionally substituted on the phenyl ring with one or more halogen, $(C_1-C_6)$alkyl, $(C_1-C_6)$alkoxy, trifluoromethyl, cyano, hydroxy, benzyloxy, or nitro,
piperidin-4-yl, piperidin-3-yl, or pyrrolidin-3-yl, each of which may optionally be substituted on the nitrogen atom of the piperidine or pyrrolidine ring with $(C_1-C_6)$alkyl, hydroxy-substituted $(C_1-C_6)$alkyl, $(C_1-C_3)$alkoxy-substituted $(C_1-C_3)$alkyl, benzyl, or phenyl optionally substituted with one or more of $(C_1-C_6)$alkyl, $(C_1-C_6)$alkoxy, trifluoromethyl, cyano, hydroxy, benzyloxy, nitro, or halogen,
—$NR^6R^7$
where $R^6$ is hydrogen or $(C_1-C_6)$alkyl;
$R^7$ is $(C_1-C_9)$alkyl; or phenyl optionally substituted with one or more of $(C_1-C_6)$alkyl, hydroxy-substituted $(C_1-C_6)$alkyl, $(C_1-C_3)$alkoxy-substituted $(C_1-C_3)$alkyl, phenyl, hydroxy, benzyloxy, $(C_1-C_6)$alkoxy, trifluoromethyl, cyano, nitro, or a halogen atom, or
$R^6$ and $R^7$, taken together with the nitrogen atom to which they are attached, form a 5- to 10-membered saturated or unsaturated heterocyclic ring which is optionally substituted by one or more $(C_1-C_6)$alkyl, $(C_1-C_6)$alkoxy, hydroxy-substituted $(C_1-C_3)$alkyl, $(C_1-C_3)$alkoxy-substituted $(C_1-C_3)$alkyl, benzyl, phenyl, hydroxy, benzyloxy, or fluorine;
or
$R^4$ and $R^5$, taken together with the nitrogen atom to which they are attached, form a 5- to 1 0-membered saturated or unsaturated heterocyclic radical optionally substituted with one or more of fluorine, $(C_1-C_6)$alkyl, $(C_1-C_6)$alkoxy, $(C_1-C_6)$alkyl-amino, bis[$(C_1-C_3)$alkyl]-amino, trifluoromethyl, hydroxy, hydroxy-substituted $(C_1-C_6)$alkyl, phenyl-substituted $(C_1-C_6)$alkyl, cyano, a 5- to 10-membered aromatic monocyclic or bicyclic heterocyclic radical, or phenyl optionally substituted with one or more $(C_1-C_6)$alkyl, hydroxy, benzyloxy, $(C_1-C_6)$alkoxy, trifluoromethyl, cyano, nitro, or halogen;
or X is

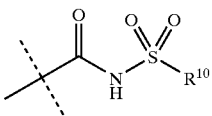

where $R^{10}$ is $(C_1-C_9)$alkyl optionally substituted with one or more phenyl, hydroxy, benzyloxy, $(C_1-C_6)$alkoxy, or a fluorine atom, or
phenyl, benzocyclohexyl or benzocyclopentyl optionally substituted on the phenyl ring with one or more of a phenyl, hydroxy, benzyloxy, $(C_1-C_6)$alkoxy, or halogen;
and pharmaceutical salts and esters thereof.

Another embodiment of the invention consists of imidazole derivatives having Formula I wherein
$R^1$ and $R^2$ are identical or different and are selected from
a phenyl group optionally substituted with one or more halogen, $(C_1-C_6)$alkyl, $(C_1-C_6)$alkoxy, trifluoromethyl, cyano, nitro, $(C_1-C_6)$alkyl carbonyl-amino, $(C_1-C_6)$alkyl amino-carbonyl-amino, or phenyl,
$(C_2-C_6)$alkyl,
cyclohexyl optionally substituted with $(C_1-C_6)$alkyl, $(C_1-C_6)$alkoxy, trifluoromethyl, cyano, or with one or more fluorine,
1- or 2-naphthyl optionally substituted with halogen, $(C_1-C_6)$alkyl, $(C_1-C_6)$alkoxy, trifluoromethyl, or cyano,
benzyl optionally substituted on the phenyl ring with one or more halogen, $(C_1-C_6)$alkyl, $(C_1-C_6)$alkoxy, trifluoromethyl, or cyano,
a 5- to 10-membered saturated or unsaturated heterocyclic radical optionally substituted with fluorine, $(C_1-C_6)$alkyl, $(C_1-C_6)$alkoxy, trifluoromethyl, or cyano, and
a 5- to 10-membered aromatic monocyclic or bicyclic heterocyclic radical optionally substituted with one or more halogen, $(C_1-C_6)$alkyl, $(C_1-C_6)$alkoxy, trifluoromethyl, cyano, nitro, or phenyl, with the proviso that $R^2$ is not an unsubstituted 4-pyridyl or an unsubstituted 4-pyrimidinyl group;
$R^3$ is hydrogen, $(C_1-C_6)$alkyl, benzyl, chloro, or bromo;
X is

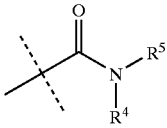

where $R^4$ is hydrogen or $(C_1-C_6)$alkyl;
$R^5$ is phenyl substituted with one or more $(C_1-C_6)$alkyl, hydroxy $(C_1-C_6)$alkyl, $(C_1-C_6)$alkoxy, phenyl, hydroxy, benzyloxy, trifluoromethyl, or halogen, or
a 5- to 10-membered aromatic monocyclic or bicyclic heterocyclic radical optionally substituted with one or more $(C_1-C_6)$alkyl, $(C_1-C_6)$alkoxy, or trifluoromethyl;
or
X is

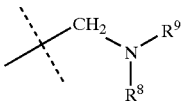

where $R^8$ is a hydrogen or $(C_1-C_6)$alkyl;

R[9] is a $(C_1–C_9)$alkyl or $(C_7–C_{11})$bicycloalkyl group, each of which is optionally substituted with one or more of phenyl, hydroxy, benzyloxy, $(C_1–C_6)$alkoxy, or fluorine, benzyl in which the phenyl ring is optionally substituted with one or more of $(C_1–C_6)$alkyl, hydroxy, benzyloxy, $(C_1–C_6)$alkoxy, trifluoromethyl, cyano, nitro, or halogen, or phenyl, benzocyclohexyl or benzocyclopentyl optionally substituted on the phenyl ring with one or more of a phenyl, hydroxy, benzyloxy, $(C_1–C_6)$alkoxy, or halogen;

or

R[8] and R[9], together with the nitrogen atom to which they are attached, form a 5- to 10-membered saturated or unsaturated heterocyclic radical optionally substituted with one or more of $(C_1–C_6)$alkyl, benzyl, hydroxy, benzyloxy, $(C_1–C_6)$alkoxy, halogen, a 5- to 10-membered saturated or unsaturated heterocyclic radical; or phenyl optionally substituted with one or more of $(C_1–C_6)$alkyl, hydroxy, benzyloxy, $(C_1–C_6)$alkoxy, trifluoromethyl, cyano, nitro, or halogen;

or
X is

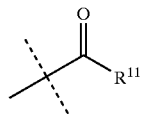

where R[11] is $(C_2–C_9)$alkyl optionally substituted with one or more phenyl, hydroxy, benzyloxy, $(C_1–C_6)$alkoxy, or fluorine, phenyl in which the phenyl ring is optionally substituted with one or more of $(C_1–C_6)$alkyl, hydroxy, benzyloxy, $(C_1–C_6)$alkoxy, trifluoromethyl, cyano, nitro, or halogen, benzyl, 2-phenyl-ethyl, benzocyclohexyl or benzocyclopentyl, each of which may be optionally substituted on one of the alkyl carbons with hydroxy, benzyloxy, or hydroxy $(C_1–C_6)$alkyl, and optionally substituted on the phenyl ring with halogen, $(C_1–C_6)$alkyl, $(C_1–C_6)$alkoxy, trifluoromethyl, cyano, hydroxy, benzyloxy or nitro, or a 5- to 10-membered aromatic monocyclic or bicyclic heterocyclic radical;

and pharmaceutical salts and esters thereof.

The terms identified above have the following meaning throughout:

"Halogen" means fluorine, chlorine, bromine or iodine.

The terms "$(C_1–C_3)$alkyl", "$(C_1–C_6)$alkyl", "$(C_2–C_6)$alkyl", "$(C_1–C_9)$alkyl", and "$(C_2–C_9)$alkyl" mean $C_1–C_3$, $C_1–C_6$, $C_2–C_6$, $C_1–C_9$, and $C_2–C_9$ linear or branched alkyl groups, respectively, that may also include a cyclic alkyl radical as part of the alkyl group. For example, this includes groups such as cyclopropyl, cyclohexyl, cyclopropyl-methyl, and cycloheptyl-methyl groups. The preferred alkyl groups are methyl, ethyl, propyl, and isopropyl groups.

"$(C_1–C_3)$alkoxy" and "$(C_1–C_6)$alkoxy" mean $(C_1–C_3)$alkyl-oxy and $(C_1–C_6)$alkyl-oxy, respectively.

"$(C_7–C_{11})$bicycloalkyl" means a $C_7–C_{11}$ bicyclic alkyl group, such as octahydro-2-pentalenyl, bicyclo[2.2.1]hept-2-yl, and bicyclo[3.2.1]oct-8-yl, that is optionally substituted with one or more methyl groups.

The term "5- to 10-membered saturated or unsaturated heterocyclic radical" means a fused or bridged, mono-, bi-, or tri-cyclic, non-aromatic heterocyclic radical which may contain one to three of the heteroatoms nitrogen, oxygen, or sulfur. These radicals include the following radicals, for example, pyrrolidin-1-yl, piperidin-1-yl, piperazin-1-yl, azepan-1-yl, morpholin-4-yl, hexahydrocyclopenta[c]pyrrol-2(1H)-yl, and thiomorpholin-4-yl.

The term "5- to 10-membered aromatic monocyclic or bicyclic heterocyclic radical" means a 5- or 6-membered aromatic heterocyclic radical or a fused bicyclic aromatic heterocyclic radical, which may contain one to three of the heteroatoms nitrogen, oxygen, or sulfur. These radicals include the following radicals, for example, furyl, thienyl, isoxazolyl, pyridyl, pyrimidinyl, benzofuranyl, and benzothienyl.

When any moiety is described as being substituted, it can have one or more of the indicated substituents that can be located at any available position on the moiety. When there are two or more substituents on any moiety, each term shall be defined independently of any other in each occurrence.

Representative salts of the compounds of Formula I include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The esters in the present invention are non-toxic, pharmaceutically acceptable ester derivatives of the alcohols of Formula I. This includes ester derivatives prepared from acetic, benzoic, mandelic, stearic, lactic, salicylic, hydroxynaphthoic, glucoheptonic, and gluconic acid. The alcohol compounds of Formula I may be esterified by a variety of conventional procedures including reacting the appropriate anhydride, carboxylic acid, or acid chloride with the alcohol group of the Formula I compound. The appropriate anhydride is reacted with the alcohol in the presence of an acylation catalyst such as 1,8-bis[dimethylamino]naphthalene or DMAP (N,N-dimethylaminopyridine). An appropriate carboxylic acid may be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and optionally, an acylation catalyst. Esterification may also be reached using the appropriate carboxylic acid in the presence of trifluoroacetic anhydride and optionally, pyridine, or in the presence of N,N-carbonyldiimidazole with pyridine. Reaction of an acid chloride with the alcohol may be carried out with an acylation catalyst such as DMAP or pyridine. One skilled in the art would readily know how to successfully carry out these as well as other methods of esterification of alcohols. Sensitive or reactive groups on the compound of Formula I may need to be protected during any of the above methods for forming esters, and protecting groups may be added and removed by conventional methods well known in the art.

It will be appreciated that diastereomers and enantiomers of the exemplified structures will often be possible, and that pure isomers represent preferred embodiments. It is intended that pure stereoisomers, and mixtures thereof, are within the scope of the invention.

The compounds of this invention may, either by nature of asymmetric centers or by restricted rotation, be present in the form of isomers. Any isomer may be present in the (R)-, (S)-, or (R,S) configuration, preferably in the (R)- or (S)- configuration, whichever is most active.

All isomers, whether separated, pure, partially pure, or in racemic mixture, of the compounds of this invention are encompassed within the scope of this invention. The purification of said isomers and the separation of said isomeric mixtures may be accomplished by standard techniques known in the art.

Geometric isomers by nature of substituents about a double bond or a ring may be present in cis (=Z—) or trans (=E—) form, and both isomeric forms are encompassed within the scope of this invention.

The particular process to be utilized in the preparation of the compounds of this invention depends upon the specific compound desired. Such factors as the selection of the specific moieties and the specific substituents on the various moieties, all play a role in the path to be followed in the preparation of the specific compounds of this invention. These factors are readily recognized by one of ordinary skill in the art.

For synthesis of any particular compound, one skilled in the art will recognize that the use of protecting groups may be required for the synthesis of compounds containing certain substituents. A description of suitable protecting groups and appropriate methods of adding and removing such groups may be found in: Protective Groups in Organic Synthesis, Second Edition, T. W. Greene, John Wiley and Sons, New York, 1991.

In the Reaction Schemes below, one skilled in the art will recognize that reagents and solvents actually used may be selected from several reagents and solvents well known in the art to be effective equivalents. When specific reagents or solvents are shown in a Reaction Scheme, therefore, they are meant to be illustrative examples of conditions desirable for the execution of that particular Reaction Scheme. Abbreviations not identified in accompanying text are listed later in this disclosure under "Abbreviations and Acronyms."

Another object of this invention is to provide methods of making the compounds of the invention. The compounds may be prepared from readily available materials by the methods outlined in Reaction Schemes 1 and 2 below, and by obvious modifications thereto.

The present invention relates to the use of the compounds of this invention for the treatment of bulimia and obesity including associated dyslipidemia and other obesity- and overweight-related complications such as, for example, cholesterol gallstones, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, Syndrome X, type II diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease and peripheral vessel disease. The compounds of this invention may also be useful for treating physiological disorders related to, for example, regulation of insulin sensitivity, inflammatory response, plasma triglycerides, HDL, LDL and cholesterol levels and the like.

The compounds of Formula I of this invention are expected to be valuable as therapeutic agents. Accordingly, an embodiment of this invention includes a method of treating the various conditions identified above in a patient (including mammals) which comprises administering to said patient a composition containing an amount of the compound of Formula I that is effective in treating the target condition.

Compounds of Formula I may be administered alone or in combination with one or more additional therapeutic agents. Combination therapy includes administration of a single pharmaceutical dosage formulation which contains a compound of Formula I and one or more additional therapeutic agents, as well as administration of the compound of Formula I and each additional therapeutic agents in its own separate pharmaceutical dosage formulation. For example, a compound of Formula I and a therapeutic agent may be administered to the patient together in a single oral dosage composition such as a tablet or capsule, or each agent may be administered in separate oral dosage formulations.

Where separate dosage formulations are used, the compound of Formula I and one or more additional therapeutic agents may be administered at essentially the same time (e.g., concurrently) or at separately staggered times (e.g., sequentially).

For example, the compounds of Formula I may be used in combination with other therapies and drugs useful for the treatment of obesity, for example, in combination with $\beta_3$-adrenoreceptor agonists such as CL-316,243, or in combination with a drug compound that modulates digestion and/or metabolism such as drugs that modulate thermogenesis, lipolysis, gut motility, fat absorption, and satiety.

In addition, the compounds of Formula I may be administered in combination with one or more of the following hypoglycemic agents for the treatment of diabetes or diabetes-related disorders: insulin; biguanidines such as metformin or buformin; sulfonylureas such as acetohexamide, chloropropamide, tolazamide, tolbutamide, glyburide, glipizide, glyclazide; or any other insulin secretagogue such as, for example, repaglinide and nateglinide; or α-glycosidase inhibitors such as acarbose, voglibose, or miglitol. Also, the compounds of Formula I may be used in combination with HMG Co-A reductase inhibitors (statins), bile acid binding resin, or fibric acid derivatives to improve the lipid profile of subjects with dyslipidemia. Compounds of Formula I may also be used in combination with agents that regulate hypertension (e.g., inhibitors of angiotension converting enzyme (ACE), β-blockers, calcium channel blockers).

Furthermore, compounds of the present invention were determined, following oral dosing in rodents, to be present in significant concentrations in the brain. Therefore, the compounds of this invention may have utility for the treatment of any of various CNS (central nervous system) or psychological disorders, such as the treatment of substance or behavioral addiction, and the treatment of disorders associated with the use of psychotropic substances. Likewise, the compounds of this invention may have utility for the management and treatment of cognition and memory disorders.

The compounds of Formula I may also be utilized, in free base form or in compositions, as well as in research and diagnostics or as analytical reference standards, and the like, which are well known in the art. Therefore, the present invention includes compositions which are comprised of an inert carrier and an effective amount of a compound of Formula I, or a salt, or ester thereof. An inert carrier is any material which does not interact with the compound to be carried and which lends support, means of conveyance, bulk, traceable material, and the like to the compound to be carried. An effective amount of the compound is that amount which produces a result or exerts an influence on the particular procedure being performed.

It is anticipated that prodrug forms of the compounds of this invention will prove useful in certain circumstances, and such compounds are also intended to fall within the scope of the invention. Prodrug forms may have advantages over the parent compounds exemplified herein, in that they are better absorbed, better distributed, more readily penetrate the central nervous system, are more slowly metabolized or cleared, etc. Prodrug forms may also have formulation advantages in terms of crystallinity or water solubility. For example, compounds of the invention having one or more hydroxyl groups may be converted to esters or carbonates bearing one or more carboxyl, hydroxyl or amino groups, which are hydrolyzed at physiological pH values or are cleaved by endogenous esterases or lipases in vivo. See for example U.S. Pat. Nos. 4,942,184; 4,960,790; 5,817,840; and 5,824,701 (all of which are incorporated herein by reference in their entirety), and references therein.

An object of this invention is to provide a method of inducing weight loss in an individual by administration of a compound of the invention. The method of the invention comprises administering to an individual a therapeutically effective amount of at least one compound of the invention, or a prodrug thereof, which is sufficient to induce weight loss. The invention further comprises a method of preventing weight gain in an individual by administering an amount of at least one compound of the invention, or a prodrug thereof, which is sufficient to prevent weight gain.

General Preparation of Compounds of Formula I

Compounds of Formula I are prepared by a variety of methodologies. The selection of the particular method to be used depends upon such factors as the availability of appropriate starting materials, compatibility of functional groups with the reagents used, and the ultimate structural features present in the final compound being prepared. It will be understood by those skilled in the art that more than one method may, in some cases, be useful for the preparation of individual compound examples of Formula I.

In general, the compounds of Formula I are prepared from the intermediate compound of Formula VI by the methods outlined in Reaction Scheme 2; the compound of formula VI is prepared by the methods outlined in Reaction Scheme 1, by one of the two paths as shown. For the compounds of Formulas Ia–d and II–XIII, unless specifically defined otherwise, R, $R^1$—$R^{11}$, and X are as defined above for Formula I.

Reaction Scheme 1

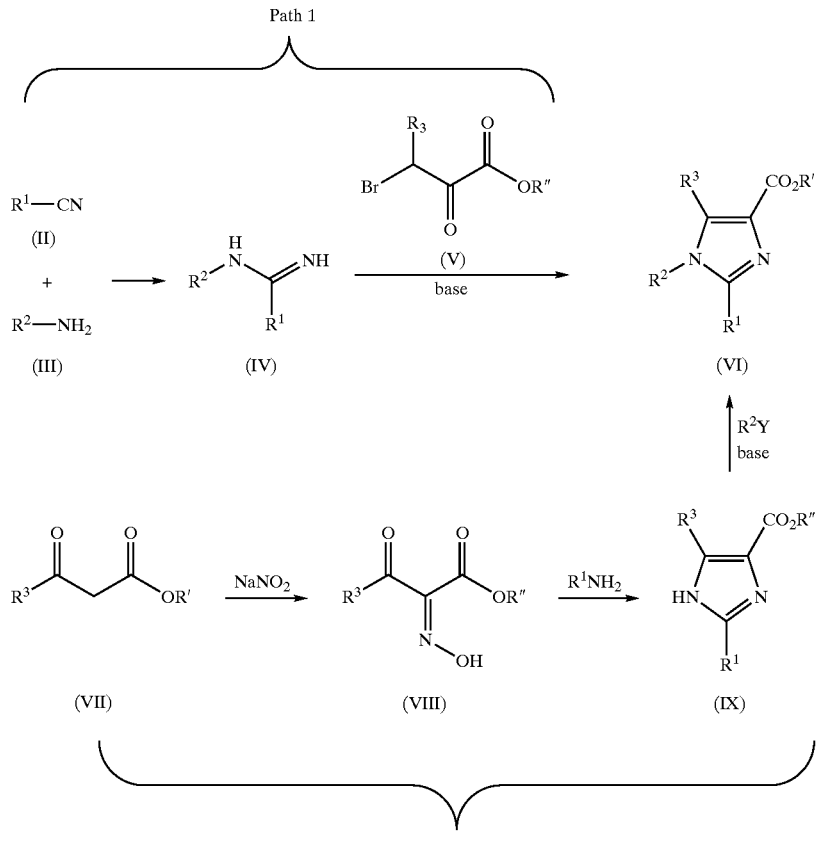

R' = H or lower alkyl
R" = lower alkyl
Y = halo, OTs or OMs

Preparation of Intermediates of Formula VI (Reaction Scheme 1)

In Path 1, an imidamide of Formula IV is prepared by reaction of an amine of Formula III with a nitrile of Formula II. This reaction is either conducted using a strong base such as a Grignard reagent (e.g., EtMgBr) in a neutral solvent (e.g., THF) at room temperature, or with a Lewis Acid (e.g., AlCl$_3$) in an inert solvent (e.g., toluene) with heating. The product, imidamide IV, is then allowed to react with a 3-bromopyruvate of Formula V by mixing together in an inert solvent (e.g., toluene or THF), with optional heating, to give the imidazole intermediate of Formula VI. This reaction may be further facilitated by the addition of a base (e.g., propyl amine, sodium carbonate, and the like) to remove excess HBr produced as a side product. Alternatively, the conversion of IV to VI may be accomplished in a stepwise manner, i.e., first carrying out the reaction of IV with V and isolation of the crude product, and then heating the residue with the R$^1$NH$_2$ compound in acetic acid complete the cyclization to imidazole VI.

In path 2, ketoesters of Formula VII are converted to an oxime compound of Formula VIII, by reaction with sodium nitrite in a protic solvent, typically acetic acid/water, while cooling. The product VIII is then heated with an amine of formula R$^1$NH$_2$ in a polar solvent such as acetonitrile, to provide the imidazole of Formula IX. Finally, N-substitution may be carried out by treatment of IX with a base and a compound of formula R$^2$Y, where Y is a leaving group such as halogen, mesylate, or tosylate. For this pathway, when the R$^2$ is aryl, it is generally an activated (electrophilic) haloarene such as 4-halonitrobenzene or a 2- or 4-halopyridine, capable of undergoing nucleophilic aromatic substitution reactions.

The compounds of Formula VI, in which R' is H, may be made from the compounds of Formula VI in which R' is alkyl, by ester hydrolysis methods well known in the art.

Reaction Scheme 2

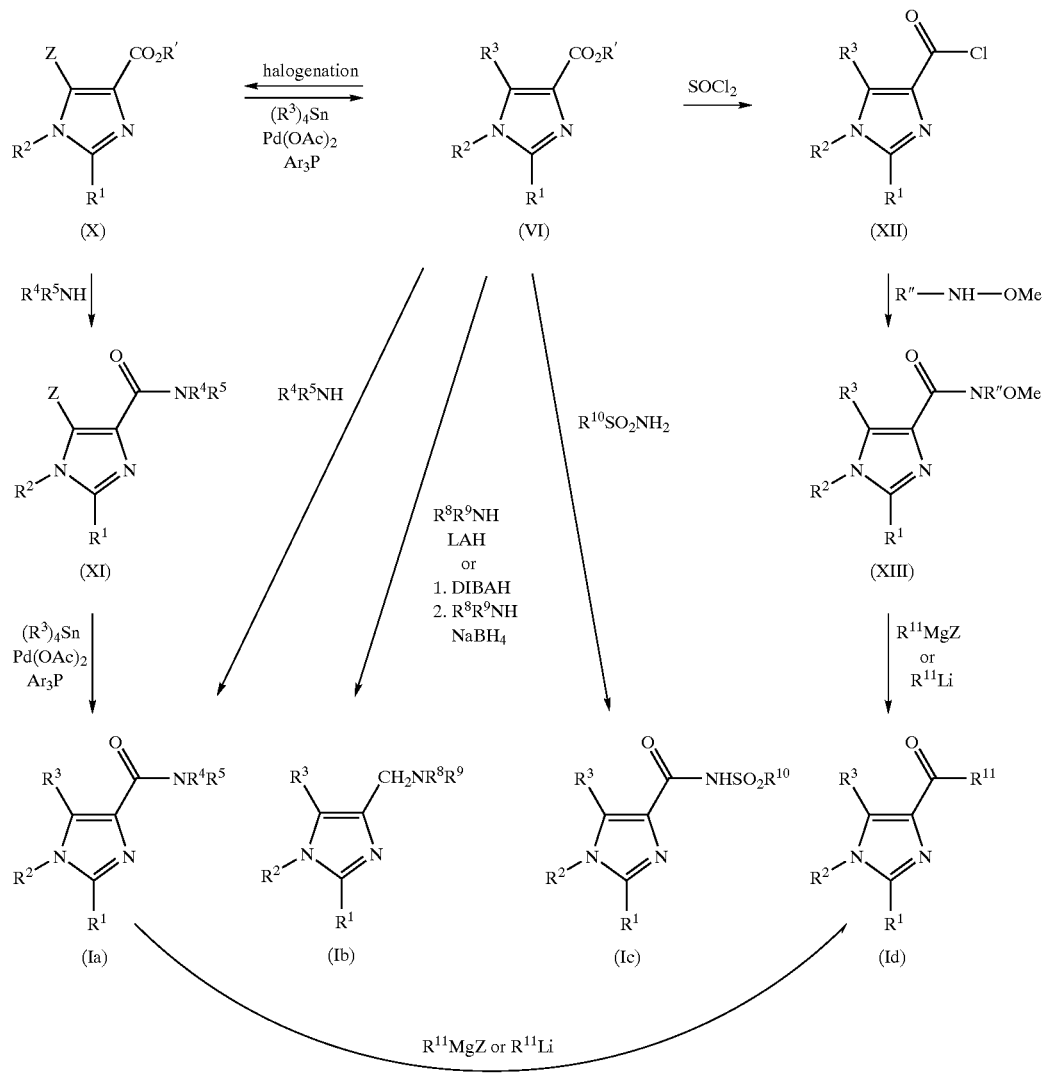

Z = halogen
R' = H or lower alkyl
R" = lower alkyl

Preparation of Compounds of Formula I (Reaction Scheme 2)

The compounds of Formula VI, prepared as shown in Reaction Scheme 1, may then be used for the preparation of the compounds of Formula I. To illustrate the methods which are useful for the preparation of the Formula I compounds, synthetic routes are shown for the more specific compounds of Formula Ia, Ib, Ic, and Id. These four structures represent the variants of the Formula I compounds when X=—C(=O)NR$^4$R$^5$, —CH$_2$NR$^8$R$^9$, —C(=O)NHSO$_2$R$^{10}$, and —C(=O)R$^{11}$, respectively.

The synthetic methods for the preparation of each of these variants of the Formula I compounds are illustrated in Reaction Scheme 2.

In one such method, compounds of Formula VI, in which R'=H, the carboxylic acid group is first activated as an acid halide (e.g., using SOCl$_2$ or TFFH) and subsequently treated with a compound of formula R$^4$R$^5$NH, usually with base present such as triethyl amine or PS-DIEA (polystyrene bound-diisopropylethylamine). Alternatively, the acid may be activated as a carbodiimide adduct (e.g., with 1-(3-dimethylaminopropyl, triethylamine, and 1-hydroxy-7-azabenzotriazole)-3-ethylcarbodiimide hydrochloride) or as a hexafluorophenyl ester (prepared from hexafluorophenol and EDCI). Following activation, a compound represented as R$^4$R$^5$NH is added to complete the reaction to the Formula Ia compound. One-pot variations of this conversion may also be carried out, for example, by mixing a coupling reagent such as HATU and the R$^4$R$^5$NH compound at the same time.

Compounds of Formula Ia may also be prepared from compounds of Formula VI where R'=alkyl by heating together the R$^4$R$^5$NH compound and trimethylaluminum.

Compounds of Formula Ia may also be prepared as shown, from an ester of Formula VI where R$^3$ is H, by first halogenating the imidazole by standard means (e.g., NBS or SO$_2$Cl$_2$) to give the haloimidazole of Formula X. While this intermediate may be used to prepare Formula VI intermediates where R$^3$≠H, using such methods as Pd-catalyzed organotin coupling reactions (e.g., when R$^3$ is methyl), Formula X compounds may also be converted to the amides of Formula XI under the same conditions described above for conversion of Formula VI compounds to Formula IA. The resulting amide of Formula XI may then be converted to a Formula Ia compound, where R$^3$≠H, by Pd-catalyzed organotin coupling reactions.

Formula Ib compounds may be prepared from Formula VI compounds in the presence of an amino compound of Formula R$^8$R$^9$NH under reductive conditions. When R$^8$ is hydrogen, a Formula VI compound where R'=alkyl, is first partially reduced to the aldehyde with, for example, diisobutylaluminum hydride (DIBAH), the R$^8$R$^9$NH compound is added to form an imine intermediate in situ, which is then reduced with sodium borohydride. When R$_8$≠H, the reductive alkylation may be accomplished in one step with the R$^8$R$^9$NH compound and lithium aluminum hydride by using the procedure described by Khanna et al., (Synthesis 607–608, 1975).

The acylsulfonamides of Formula Ic may be prepared by reaction of the Formula VI compound (where R'=H) with a sulfonamide of Formula R$^{10}$SO$_2$NH$_2$, facilitated by a coupling agent such as, for example, a N,N'-dialkyl carbodiimide such as N,N'-dicyclohexyl carbodiimide and a base such as, for example, DMAP.

Formula Id compounds may be prepared by conversion of an acid chloride represented by Formula XII, prepared as described above from VI (where R'=H) and SOCl$_2$, to an amide of Formula XIII, which is then allowed to undergo reaction with a organometallic reagent such as, for example, an alkyl or aryl Grignard reagent of Formula R$^{11}$MgBr, prepared by standard methods. The resulting product is the ketone of Formula Id. This Formula Id ketone may also be prepared by similar reaction of aryl- or alkllithium reagents, such as, for example, R$^{11}$Li, with Formula XIII, or certain Formula Ia amides where R$^4$R$^5$NH is 4-piperidone.

Conversion of the substituted compounds of Formula Ia, Ib, Ic, and Id to differently substituted Formula I compounds may be carried out using standard functional group conversion chemistry. For example, keto substituents may be reduced with reagents such as Na$_2$BH$_4$, to the corresponding hydroxy substituted compounds. Other such examples are 1) the conversion of nitrophenyl substituent to the corresponding aminophenyl substituent, and 2) O- or N-alkylation or acylation of OH or NH substituents to give the corresponding O- or N-alkyl or O- or N-acyl substituted compounds.

EXPERIMENTAL EXAMPLES

The following specific preparative examples are included as illustrations of preparation of specific compounds of the invention, and are not to be construed as limiting the scope of the invention in any way.

NMR Methods:

Proton ($^1$H) nuclear magnetic resonance (NMR) spectra were measured with a General Electric GN-Omega 300 (300 MHz) spectrometer with either Me$_4$Si (δ 0.00) or residual protonated solvent (CHCl$_3$ δ 7.26; MeOH δ 3.30; DMSO δ 2.49) as reference standard. Carbon ($^{13}$C) NMR spectra were measured with a General Electric GN-Omega 300 (75 MHz) spectrometer with solvent (CDCl$_3$ δ 77.0; d$_3$-MeOD; δ 49.0; d$_6$-DMSO δ 39.5) as reference standard.

LC-MS Instrumentation:

(a) a Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120–800 amu over 1.5 seconds. ELSD (Evaporative Light Scattering Detector) data was also acquired as an analog channel.

(b) a Hewlett-Packard 1100 HPLC equipped with a quaternary pump, a variable wavelength detector set at 254 nm, a YMC pro C-18 column (2×23 mm, 120 A), and a Finnigan LCQ ion trap mass spectrometer with electrospray ionization. Spectra were scanned from 120–1200 amu using a variable ion time according to the number of ions in the source.

HPLC conditions. In the Examples and Tables provided below, LC-MS data are given with retention times (RT) determined by using one of the following methods:

Method 1. Eluents were A: 2% acetonitrile in water with 0.02% TFA, and B: 2% water in acetonitrile with 0.02% TFA. Elution conditions consisted of a flow rate of 1.0 mL/min with an initial hold at 10% B for 0.5 minutes, followed by gradient elution from 10% B to 95% B over 3.5 minutes, followed by a final hold at 95% B for 0.5 minutes. Total run time was 6.5 minutes.

Method 2. Eluents as above; elution at a flow rate of 1.5 mL/min with an initial hold at 10% B for 0.5 minutes, followed by gradient elution from 10% B to 90% B over 3.5 minutes, followed by a final hold at 90% B for 0.5 minutes. Total run time was 4.8 minutes.

Abbreviations and Acronyms

When the following abbreviations are used herein, they have the following meaning:

| | |
|---|---|
| BINAP | 2,2'-bis(diphenylphosphino)- 1,1'-binaphthyl |
| CD$_3$OD | methanol-d$_4$ |
| Celite ® | diatomaceous earth filter agent, ®Celite Corp. |
| DMAP | 4-(N,N-dimethylamino)pyidine |
| DMF | N,N-dimethylformamide |
| DMSO | dimethylsulfoxide |
| EDCI | 1-(3-dimethylaminopropyl)-3-ethylcarbodiimide hydrochloride |
| ELSD | evaporative light scattering detector |
| EtOAc | ethyl acetate |
| EtOH | ethanol (100%) |
| Et$_2$O | diethyl ether |
| Et$_3$N | triethylamine |
| h | hour(s) |
| HATU | O-(7-azabenzotriazol-1-yl)-N,N,N',N'-tetramethyluronium hexafluorophosphate |
| HPLC | high performance liquid chromatography |
| LC-MS | liquid chromatography-mass spectroscopy |
| min | minute(s) |
| m/z | mass-to-charge ratio |
| MeCN | acetonitrile |
| Ms | methanesulfonyl |
| NBS | N-bromosuccinimide |
| NMM | 4-methylmorpholine |
| OMs | methanesulfonyl-oxy |
| OTs | 4-toluenesulfonyl-oxy |
| PS-DIEA | Polystyrene-bound diisopropylethylamine |
| Rf | retention factor (TLC) |
| RT | retention time (HPLC) |
| rt | room temperature |
| THF | tetrahydrofuran |
| TFA | trifluoroacetic acid |
| TFFH | Fluoro-N,N,N',N'-tetramethylformamidinium hexafluorophosphate |
| TLC | thin layer chromatography |
| Ts | 4-toluenesulfonyl |

Example 1

Preparation of 2,4-dichloro-N-(4-chlorophenyl) benzenecarboximidamide

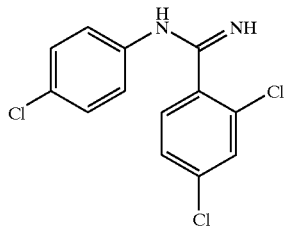

Under argon, 4-chloroaniline (6.67 g, 52.5 mmol) was slowly added to EtMgBr (52 mL, 1 M in THF, 52 mmol) portion wise. After the solution was stirred for 0.5 h, 2,4-dichlorobenzonitrile (9.03 g, 52.5 mmol) was added. The resulting solution was stirred at rt overnight. The reaction mixture was carefully quenched with water and extracted with ethyl acetate. The organic layer was dried over MgSO$_4$, filtered, and concentrated. Crude product (16.26 g,) was obtained as a sticky brown foam which was used without purification for the next step. LC-MS m/z 299.3 (MH$^+$), retention time 1.75 min (MDLC 1); $^1$H NMR (300 MHz, CDCl$_3$) δ 4.92 (2H, br), 7.09–7.51 (7H, m).

Example 2

Preparation of N-(4-chlorophenyl)-3-methylbutanimidamide

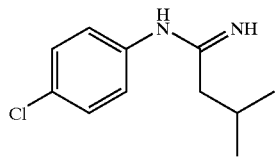

To a solution of 3-methylbutanenitrile (250 mg, 3.0 mmol) and AlCl$_3$ (400 mg, 3.0 mmol) in toluene (6 mL) was added 4-chloroaniline (383 mg, 3.0 mmol). The resulting solution was stirred at reflux for 2 h, diluted with water, and extracted with EtOAc. The aqueous layer was neutralized with saturated NaHCO$_3$ solution and extracted with EtOAc. The combined extracts were dried over MgSO$_4$, filtered, and concentrated. The crude product (364 mg, 58% yield) was used for the next step without purification.

Example 3

Preparation of ethyl 1-(4-fluorophenyl)-2-(2-chlorophenyl)-1H-imidazole-4-carboxylate

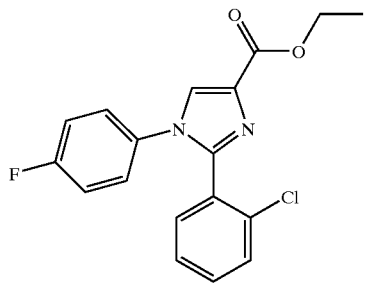

To a solution of crude 2-chloro-N-(4-fluorophenyl) benzenecarboximidamide (6.8 g, 27 mmol) in toluene (100 mL), ethyl bromopyruvate (3.5 mL, 27 mmol) was added. The resulting solution was heated at 115° C. for 90 minutes. The reaction mixture was cooled to rt. Propylamine (2.2 mL, 27 mmol) was added. The reaction mixture was diluted with ethyl acetate and washed with saturated NaCl solution. The organic layer was dried over MgSO$_4$, filtered, and concentrated. The residue was purified by flash chromatography over silica gel (30% ethyl acetate in hexane) to give the product (3.4 g, 37% overall yield from 4-fluoroaniline) as a light yellow solid: LC-MS m/z 345.2 (MH$^+$), retention time 2.78 min (method 1); Rf=0.20 (30% EtOAc in hexane). $^1$H NMR (300 MHz, CDCl$_3$) δ 1.38–1.43 (3H, t, J=6.9 Hz), 4.39–4.46 (2H, q, J=3.9 Hz), 6.98–7.52 (8H, m), 7.89 (1H, s).

Example 4

Preparation of ethyl 1-(4-chlorophenyl)-2-(2,4-dichlorophenyl)-1H-imidazole-4-carboxylate

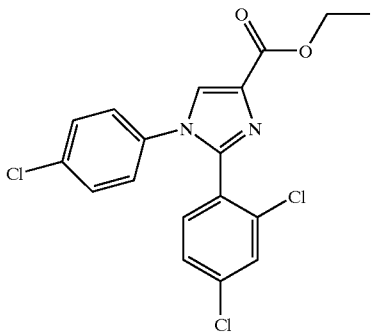

To a solution of crude 2,4-dichloro-N-(4-chlorophenyl) benzenecarboximidamide (10.3 g, 34.6 mmol) in toluene (100 mL), ethyl bromopyruvate (4.3 mL, 34.6 mmol) and Na$_2$CO$_3$ (7.3 g, 41.6 mmol) were added. The resulting solution was heated at reflux for 3 h. The reaction mixture was cooled to rt. The solid was filtered off and the solvent was evaporated. The residue was purified by flash chromatography over silica gel (40% ethyl acetate in hexane) to give the product (7.5 g, 52% overall yield from 4-chroloaniline) as a light yellow solid: LC-MS m/z 395 (MH$^+$), retention time 3.91 min (method 1); mp 143–144° C.; Rf=0.63 (50% EtOAc in hexane). $^1$H NMR (300 MHz, CDCl$_3$) δ 1.39–1.43 (3H, t, J=7.2 Hz), 4.39–4.46 (2H, q, J=6.9 Hz), 7.04–7.08 (2H, m), 7.25–7.50 (5H, m), 7.89 (1H, s).

Example 5

Preparation of ethyl 2-(2-chlorophenyl)-1-(4-chlorophenyl)-5-ethyl-1H-imidazole-4-carboxylate

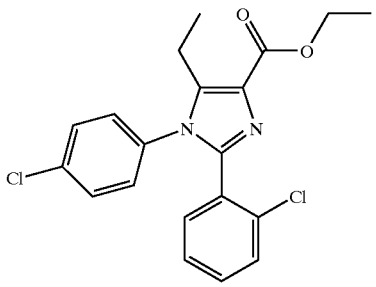

A solution of 2-dichloro-N-(4-chlorophenyl) benzenecarboximidamide (10 g, 37.7 mmol) in THF (100 mL) was treated with K$_2$CO$_3$ (5.2 g, 37.7 mmol) followed by the slow addition of ethyl 3-bromo-2-oxopentanoate (10.1 g, 45 mmol) over 3 h. The reaction mixture was stirred at rt overnight. The solid was then filtered off and the solvent was evaporated. The residue (20 g, 37.7 mmol) was dissolved in acetic acid (100 mL) and heated at reflux for 1 h. The reaction mixture was cooled to rt, diluted with water (200 mL), and extracted with ethyl acetate. The organic layer was washed with water. The aqueous layer was neutralized with saturated NaHCO$_3$, and extracted with ethyl acetate. The combined extracts were dried over MgSO$_4$, filtered, and concentrated. The residue was purified by flash chromatography over silica gel (40% ethyl acetate in hexane) to give the product (8.5 g, 40% overall yield from 4-chroloaniline) as a light yellow solid: LC-MS m/z 389 (MH$^+$), retention time 3.31 min (method 1); Rf=0.28 (40% EtOAc in hexane). $^1$H NMR (300 MHz, CDCl$_3$) δ 1.05–1.10 (3H, t, J=7.5 Hz), 1.40–1.44 (3H, t, J=7.2 Hz), 2.85–2.92 (2H, q, J=4.2 Hz), 4.39–4.46 (2H, q, J=7.2 Hz), 7.09–7.41(8H, m).

Example 6

Preparation of 2-(2-chlorophenyl)-1-(4-chlorophenyl)-5-ethyl-N-(1-piperidinyl)-1H-imidazole-4-carboxamide

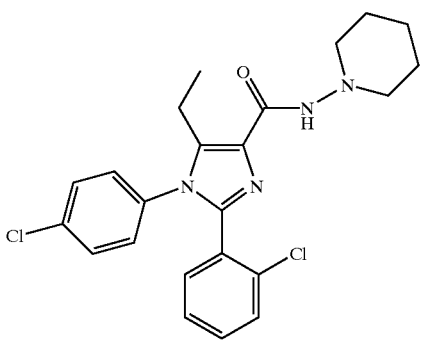

To a solution of 1-aminopiperidine (2.48 mL, 23 mmol) in CH$_2$Cl$_2$ (15 mL) was added trimethylaluminum (11.5 mL, 2 M in hexane, 23 mmol). After the mixture was stirred for 0.5 h, a solution of ethyl 2-(2-chlorophenyl)-1-(4-chlorophenyl)-5-ethyl-1H-imidazole-4-carboxylate (3.0 g, 7.7 mmol) in CH$_2$Cl$_2$ (10 mL) was added. The reaction mixture was heated at reflux for 2 h and cooled to rt. Water was slowly added dropwise to the reaction mixture at 0° C. until no more gas bubbled out. The mixture was dried over Mg$_2$SO$_4$, filtered, and concentrated. The residue was purified by flash chromatography over silica gel (40% then 60% ethyl acetate in hexane) to give the product (2.4 g, 64% yield) as a white solid: LC-MS m/z 443 (MH$^+$), retention time 2.95 min (method 1); mp 208–209° C.; Rf=0.74 (EtOAc). $^1$H NMR (300 MHz, CDCl$_3$) δ 0.98–1.03 (3H, t, 7.8 Hz), 1.35–1.37 (2H, m), 1.58–1.70 (4H, m), 2.77–2.88 (6H, m), 6.70–7.30 (8H, m), 7.84 (1H, s).

Example 7

Preparation of 1-(4-chlorophenyl)-2-(2,4-dichlorophenyl)-5H-imidazole-4-carboxylic acid

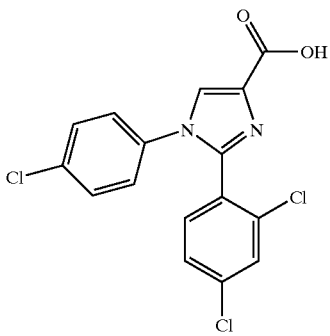

To a solution of ethyl 1-(4-chlorophenyl)-2-(2,4-dichlorophenyl)-1H-imidazole-4-carboxylate (1.1 g, 2.79 mmol) in MeOH (20 mL), a solution of KOH (2.2 g, 39 mmol) in H$_2$O (20 mL) was added. The mixture was heated at 90° C. for 3 h. The reaction mixture was cooled to rt and the MeOH was evaporated. HCl (1N) was added until a white precipitate formed. The solid was filtered off, and dried under vacuum. The product (1.0 g, 98% yield) was obtained as a white solid: LC-MS m/z 367 (MH+), retention time is 3.43 min (method 1); mp 150–151° C.; ¹H NMR (300 MHz, CDCl₃) δ 7.24–7.65 (7H, m), 8.26 (1H, s).

Example 8

Preparation of 1-(4-chlorophenyl)-2-(2,4-dichlorophenyl)-N-(4-morpholin)l)-1H-imidazole-4-carboxamide

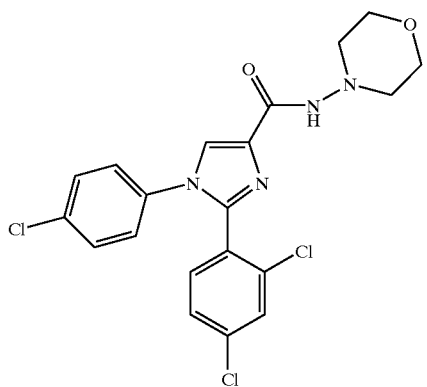

To a solution of 1-(4-chlorophenyl)-2-(2,4-dichlorophenyl)-5H-imidazole-4-carboxylic acid (50 mg, 0.137 mmol) in CH₂Cl₂ (5 mL), 1-(3-dimethylaminopropyl)-3-ethylcarbodiimide hydrochloride (58 mg, 0.164 mmol), 1-hydroxy-7-azabenzotriazole (40 mg, 0.164 mmol), and triethylamine (1.5 mL) were added. After the mixture was stirred for 15 minutes, 4-morpholinamine (0.164 mmol) was added. The reaction mixture was stirred at rt overnight, and washed with water. The organic layer was dried over MgSO₄, filtered, and concentrated. The residue was purified by HPLC (YMC-packed PRO C18 15×200 mm column, 10–90% CH₃CN in H₂O/TFA, 20 mL/min.) to give the product (10 mg, 16% yield) as a yellow oil: LC-MS m/z 451 (MH+), retention time 3.03 min (method 1); Rf=0.57 (50% EtOAc in hexane); ¹H NMR (300 MHz, CDCl₃) δ 2.97–3.00 (4H, t, J=4.5 Hz), 3.83–3.86 (4H, t, J=4.2 Hz), 7.04–7.39 (8H, m), 7.92 (1H, s).

Example 9

Preparation of 2-(2-chlorophenyl)-1-(4-chlorophenyl)-N-(3-pyridinyl)-1H-imidazole-4-carboxamide

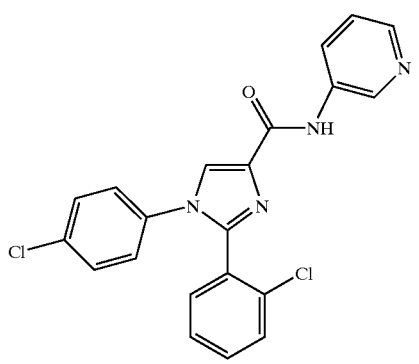

2-(2-chlorophenyl)-1-(4-chlorophenyl)-1H-imidazole-4-carboxylic acid (403 mg, 1.2 mmol) was dissolved in dichloromethane (5 mL) and treated with O-(7-azabenzotriazol-1-yl)-N,N,N',N'-tetramethyluronium hexafluorophosphate (HATU) (459 mg, 1.56 mmol) and N-methylmorpholine (NMM) (182 mg, 1.8 mmol). The mixture was stirred under argon for 15 minutes before 3-aminopyridine (349 mg, 3.6 mmol) was added. Stirring at rt was continued overnight. The reaction mixture was then adsorbed onto silica gel and chromatographed (2–3% MeOH in CH₂Cl₂) to afford 2-(2-chlorophenyl)-1-(4-chlorophenyl)-N-(3-pyridinyl)-1H-imidazole-4-carboxamide (266 mg, 54% yield): LC-MS m/z 409.3, retention time 2.43 min (method 1).

Example 10

Preparation of 2-(2-chlorophenyl)-1-(4-chlorophenyl)-N'-[2-(trifluoromethyl)phenyl]-1H-imidazole-4-carbohydrazide

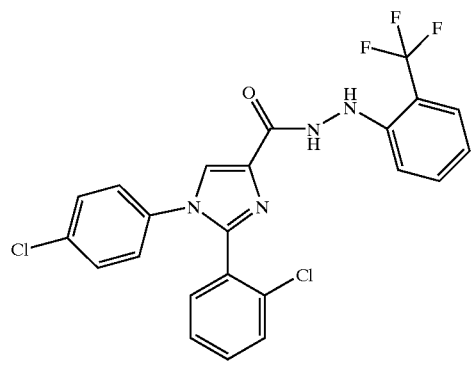

In a 20-mL screw-cap vial, 100 mg (0.3 mmol) 2-(2-chlorophenyl)-1-(4-chlorophenyl)-1H-imidazole-4-carboxylic acid, 87 mg (0.33 mmol) TFFH (Advanced Chemtech, Louisville, Ky.), and 5.0 equiv. PS-DIEA (Argonaut Technologies Inc., San Carlos, Calif.) (loading level: 3.50 mmol/g, 429 mg, 1.5 mmol) were heated in 8 mL 1,2-dichloroethane at 35° C. overnight. The formation of acyl fluoride was monitored by LC-MS. To the mixture, 1.1 equiv. (58 mg, 0.33 mmol) 2-(trifluoromethyl)phenyl hydrazine was added and the reaction continued overnight. The mixture was filtered through a filter tube (polypropylene frit), and the filtrate was evaporated under reduced pressure. The crude product was redissolved in 1 mL MeOH and purified by preparative HPLC to give 41.8 mg of 2-(2-chlorophenyl)-1-(4-chlorophenyl)-N'-[2-(trifluoromethyl)phenyl]-1H-imidazole-4-carbohydrazide as the trifluoroacetate salt (light yellow solid, 23% yield). ¹H NMR (400 MHz, CDCl₃) δ 8.70 (s, 1 H), 7.85 (s, 1 H), 7.45 (m, 2 H), 7.20–7.38 (m, 6 H), 7.12 (d, 1 H), 7.00 (d, 2 H), 6.88 (t, 1 H), 6.60 (s, 1 H); LC-MS m/z 491.2 (MH+), retention time 4.02 min (method 2).

The free base form of the product was obtained by dissolving the TFA salt in dichloromethane, washing with saturated aqueous sodium carbonate solution and water, followed by drying the organic phase with magnesium sulfate, and evaporation of the organic phase under reduced pressure. The hydrochloride salt form of the product was obtained by treating the free base in dichloromethane with 1.0 M hydrogen chloride in diethyl ether until no more precipitate was formed, followed by evaporation of solvent under reduced pressure.

Example 11

Preparation of 1-{[2-(2-chlorophenyl)-1-(4-chlorophenyl)-1H-imidazol-4-yl]carbonyl}-4-[4-(trifluoromethyl)phenyl]piperazine

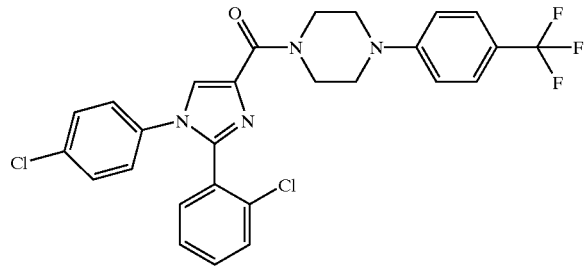

In a 20-mL screw-cap vial, 100 mg (0.3 mmol) 2-(2-chlorophenyl)-1-(4-chlorophenyl)-1H-imidazole-4-carboxylic acid, 87 mg (0.33 mmol) TFFH, and 5.0 equiv. PS-DIEA (loading level: 3.50 mmol/g, 429 mg, 1.5 mmol) were heated in 8 mL 1,2-dichloroethane at 35° C. overnight. The formation of acyl fluoride was monitored by LC-MS. To the mixture, 1.1 equiv. (76 mg, 0.33 mmol) 1-(4-trifluormethylphenyl)-piperazine was added and the reaction continued overnight. The mixture was filtered through a filter tube (polypropylene frit), and the filtrate was evaporated under reduced pressure. The crude product was redissolved in 1 mL MeOH and purified by preparative HPLC to give 45.9 mg of 1-{[2-(2-chlorophenyl)-1-(4-chlorophenyl)-1H-imidazole-4-yl]carbonyl}-4-[4-(trifluoromethyl)phenyl]piperazine as the trifluoroacetate salt (yellow oil, 23% yield). $^1$H NMR (400 MHz, CD$_3$COCD$_3$) δ 7.95 (s, 1 H), 7.60 (m, 1 H), 7.30–7.50 (m, 7 H), 7.25 (d, 2 H), 7.05 (d, 2 H), 4.5 (bs, 2 H), 3.80 (bs, 2 H), 3.35 (m, 4 H); LC-MS m/z 545.3 (MH$^+$), retention time 4.21 min (method 2).

Example 12

2-(2,4-dichlorophenyl)-N-(trans-2-hydroxycyclohexyl)-1-(4-methoxyphenyl)-1H-imidazole-4-carboxamide

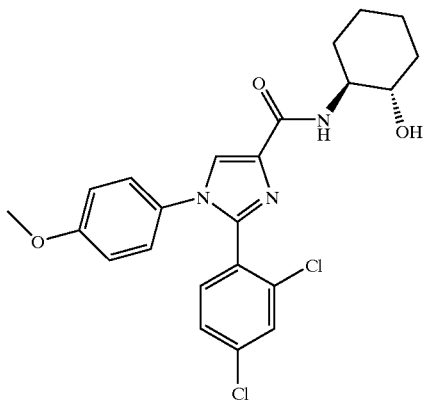

In a 20-mL screw-cap vial, 182 mg (0.5 mmol) 2-(2,4-dichlorophenyl)-1-(4-methoxyphenyl)-1H-imidazole-4-carboxylic acid, 145 mg (0.55 mmol) TFFH, and 5.0 equiv. PS-DIEA (loading level: 3.50 mmol/g, 716 mg, 2.5 mmol) were heated in 10 mL 1,2-dichloroethane at 35° C. overnight. The formation of acyl fluoride was monitored by LC-MS. To the mixture, 1.1 equiv. (84 mg, 0.55 mmol) trans-2-aminocyclohexanol hydrochloride was added and the reaction continued overnight. The mixture was filtered through a filter tube (polypropylene frit), and the filtrate was evaporated under reduced pressure. The crude product was redissolved in 1 mL MeOH and purified by preparative HPLC to give 53 mg of 2-(2,4-dichlorophenyl)-N-(trans-2-hydroxycyclohexyl)-1-(4-methoxyphenyl)-1H-imidazole-4-carboxamide (amber oil, 23% yield). $^1$H NMR (400 MHz, CD$_2$Cl$_2$) δ 7.90 (s, 1 H), 7.30–7.50 (m, 4 H), 7.10 (d, 2 H), 6.90 (d, 2 H), 3.85 (s, 3 H), 3.80 (m, 1 H), 3.50 (m, 1 H), 3.25 (bs, 1 H), 2.0 (m, 2 H), 1.75 (m, 2 H), 1.30–1.50 (m, 4 H); LC-MS m/z 460.2 (MH$^+$), retention time 3.31 min (method 2).

Example 13

Preparation of 1-{[2-(2-chlorophenyl)-1-(4-chlorophenyl)-1H-imidazol-4-yl]carbonyl}4-piperidinone

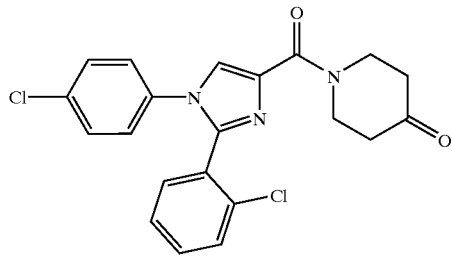

Step 1. Thionyl chloride (0.66 mL, 9 mmol) was added to a solution of 2-(2-chlorophenyl)-1-(4-chlorophenyl)-1H-imidazole-4-carboxylic acid (1 g, 3 mmol) in toluene (10 mL). The mixture was refluxed under argon for 1.5 h and concentrated to provide 2-(2-chlorophenyl)-1-(4-chlorophenyl)-1H-imidazole-4-carbonyl chloride, which was used in the next step without purification. $^1$H NMR (300 MHz, CD$_2$Cl$_2$) δ 8.40 (s, 1H), 7.69–7.09 (m, 8H).

Step 2. Triethylamine (1.46 mL, 10.45 mmol) was added to a suspension of 4-piperidinone trifluoroacetate (0.76 g, 3.58 mmol) in CH$_2$Cl$_2$ (10 mL) and a solution of 2-(2-chlorophenyl)-1-(4-chlorophenyl)-1H-imidazole-4-carbonyl chloride in CH$_2$Cl$_2$ (5 mL) was added. The mixture was stirred at rt under argon for 17 h, diluted with CH$_2$Cl$_2$ (50 mL), washed with water (2×50 mL), dried over MgSO$_4$, and concentrated to give 1-{[2-(2-chlorophenyl)-1-(4-chlorophenyl)-1H-imidazol4-yl]carbonyl}-4-piperidinone as a yellow solid (0.96 g, 77%). MS (Electrospray) 414 (MH$^+$), $^1$H NMR (300 MHz, CD$_2$Cl$_2$) δ 7.80 (s, 1H), 7.37–7.20 (m, 6H), 7.06–7.00 (m, 6H), 4.47 (br, 2H), 3.92 (br, 2H), 2.46 (t, 4H).

Example 14

5-Butyl-2-(2-chlorophenyl)-1-(4-chlorophenyl)-N-(1-piperidinyl)-1H-imidazole-4-carboxamide

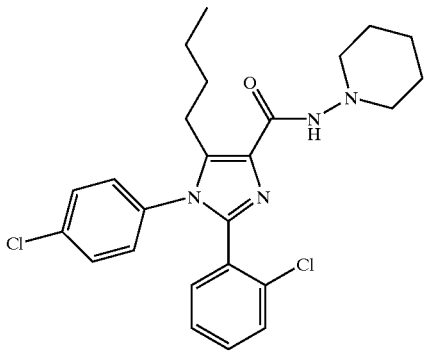

Step 1. To a solution of 5-butyl-2-(2-chlorophenyl)-1-(4-chlorophenyl)-1H-imidazole-4-carboxylic acid (438 mg, 1.12 mmol) in dry toluene (3 mL), at rt was added thionyl chloride (401 µL, 3.4 mmol). The solution was stirred overnight at rt, and then heated at 110° C. for 5 h. The resulting reaction was cooled to rt, and the solvents evaporated, to give 5-butyl-2-(2-chlorophenyl)-1-(4-chlorophenyl)-1H-imidazole-4-carbonyl chloride (455 mg, 100%), which was used in the next step without purification. LC-MS m/z 407 (MH$^+$), retention time 3.62 min (method 2).

Step 2. To a solution of 5-butyl-2-(2-chlorophenyl)-1-(4-chlorophenyl)-1H-imidazole-4-carbonyl chloride (227 mg, 0.56 mmol) in CH$_2$Cl$_2$ (5 mL), were added 1-aminopiperidine (113 mg, 1.12 mmol) and Et$_3$N (234 µL, 1.68 mmol). The solution was stirred overnight at rt, and then the solvents were evaporated under reduced pressure. The residue was purified by preparative reversed-phase HPLC, using 20 to 100% MeCN in water as gradient, to provide 125 mg (48%) of 5-butyl-2-(2-chlorophenyl)-1-(4-chlorophenyl)-N-(1-piperidinyl)-1H-imidazole-4-carboxamide as a white powder. $^1$H NMR (400 MHz, CDCl$_3$) δ 7.49–7.27 (m, 8 H), 2.93 (t, 2 H), 2.82 (bs, 4 H), 1.77–1.71 (m, 4 H), 1.46–1.37 (m, 4 H), 1.25–1.20 (2 H), 0.79 (t, 3 H). LC-MS m/z 471.33 (MH$^+$), retention time 2.88 min (method 2).

Example 15

Preparation of N-exo-bicyclo[2.2.1]hept-2-yl-2-(2-chlorophenyl)-1-(4-chlorophenyl)-1H-imidazole-4-carboxamide

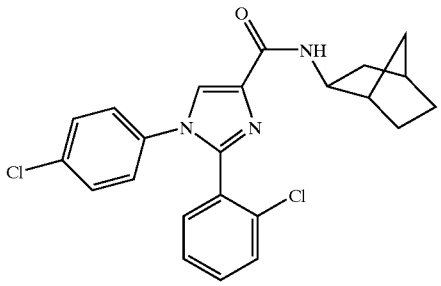

Step 1. 2-(2-Chlorophenyl)-1-(4-chlorophenyl)-1H-imidazole-4-carboxylic acid (1.5 g, 4.5 mmol) was dissolved in dichloromethane (40 mL). 1-(3-Dimethylaminopropyl)-3-ethylcarbodiimide hydrochloride (EDCI, 946 mg, 4.95 mmol) and triethylamine (500 mg, 4.95 mmol) were added followed by pentafluorophenol (815 mg, 4.37 mmol). The mixture was stirred at rt under argon for one hour before it was washed with 5% HCl, sodium bicarbonate solution, and then brine. The organic layer was dried (MgSO$_4$), filtered, and concentrated to give the crude product (1.26 g) which was chromatographed over silica gel (20% EtOAc in hexanes) to afford pentafluorophenyl 2-(2-chlorophenyl)-1-(4-chlorophenyl)-1H-imidazole-4-carboxylate (0.73 g, 32% yield): LC-MS m/z 499.0 (MH$^+$), retention time 3.93 min (method 1).

Step 2. The pentafluorophenol ester (60 mg, 0.12 mmol) and exo-norbornylamine (40 mg, 0.36 mmol) were dissolved in dichloromethane (2 mL), treated with triethylamine (49 mg, 0.48 mmol), and stirred at rt overnight. The mixture was then washed with 5% aqueous HCl, sodium bicarbonate solution and brine, dried (MgSO$_4$), filtered, and concentrated. Pure N-exo-bicyclo[2.2.1]hept-2-yl-2-(2-chlorophenyl)-1-(4-chlorophenyl)-1H-imidazole-4-carboxamide was thus obtained (30 mg, 59% yield): LC-MS m/z 426.1 (MH$^+$), retention time 3.49 min (method 1).

Example 16

Preparation of N-{[2-(2-chlorophenyl)-1-(4-chlorophenyl)-1H-imidazol-4-yl]carbonyl}-4-(trifluoromethyl) benzenesulfonamide

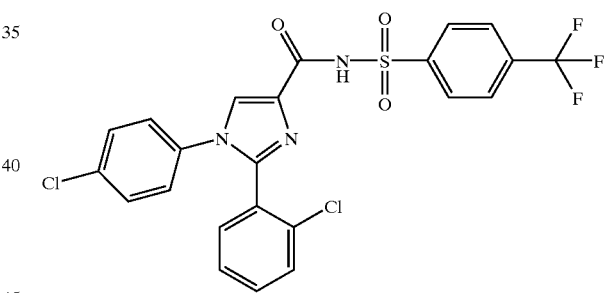

In a 20-mL screw-cap vial, 250 mg (0.75 mmol) 2-(2-chlorophenyl)-1-(4-chlorophenyl)-1H-imidazole-4-carboxylic acid, 18.3 mg DMAP (0.15 mmol), 1.25 g PS-Carbodimide (1.5 mmol) (polystyrene-supported cyclohexylcarbodiimide, Argonaut Technologies Inc., San Carlos, Calif.), 169 mg α,α,α-trifluoro-p-toluenesulfonamide (0.75 mmol), and 12 mL dichloromethane were added, and the reaction mixture was mixed by orbital shaking at rt overnight. The reaction mixture was filtered through a filter tube (polypropylene frit), and the filtrate was evaporated under reduced pressure. The crude product was redissolved in 2 mL MeOH and purified by preparative HPLC to give 39.3 mg of N-{[2-(2-chlorophenyl)-1-(4-chlorophenyl)-1H-imidazol-4-yl]carbonyl}-4-(trifluoromethyl)benzenesulfonamide (beige solid, 10% yield). $^1$H NMR (400 MHz, CD3COCD3) δ 8.25 (d, 2 H), 7.85 (s, 1 H), 7.75 (s, 2H), 7.20–7.40 (m, 6 H), 6.95 (t, 2 H); LC-MS m/z 540 (MH$^+$), retention time 3.36 min (method 2).

Example 17

Preparation of 1-{[2-(2-chlorophenyl)-1-(4-chlorophenyl)-1H-imidazol-4-yl]carbonyl}-4-(4-fluorophenyl)-4-piperidinol

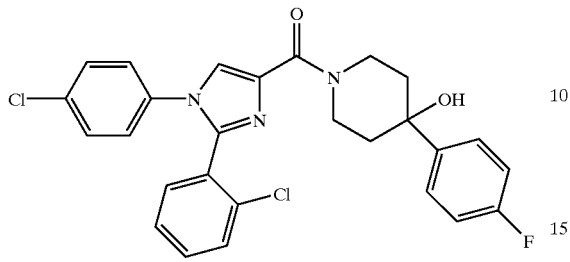

A solution of 1-{[2-(2-chlorophenyl)-1-(4-chlorophenyl)-1H-imidazol-4-yl]carbonyl}-4-piperidinone (0.1 g, 0.24 mmol, prepared as described in Example 13) in THF (4 mL) was added dropwise to a solution of 4-fluorophenylmagnesium bromide (0.6 mL, 0.60 mL) at −78° C. The mixture was stirred at −78° C. for 2 h then allowed to warm up to 30° C. Saturated NH$_4$Cl (3 mL) was added slowly followed by water (3 mL). The mixture was extracted with ethyl acetate (3×20 mL) and dried over MgSO$_4$. The product (0.056 g, 46%) was isolated by column (50% ethyl acetate in hexane). MS (Electrospray) 510.1 (M)$^+$; $^1$H NMR (300 MHz, CD$_2$Cl$_2$) δ 7.81 (s, 1H), 7.50–7.24 (m, 8H), 7.10–6.98 (m, 4H), 5.33–5.17 (m, 1H), 4.74–4.57 (m, 1H), 3.68 (t, 1H), 3.31 (t, 1H), 2.15 (br, 2H), 1.83 (d, 2H).

Example 18

Preparation of 1-{[2-(2-chlorophenyl)-1-(4-chlorophenyl)-1H-imidazol-4-yl]carbonyl}-4-(2-furyl)-4-piperidinol

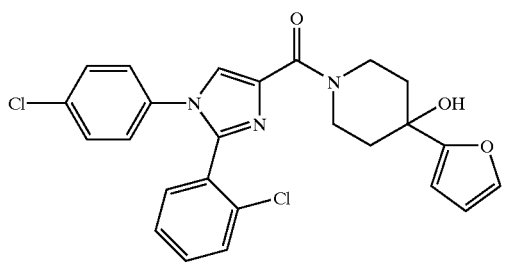

BuLi (0.875 mL, 1.40 mmol, 1 M solution in THF) was added slowly to a solution of furan (0.106 mL, 1.45 mmol) in THF (2 mL) at −78° C., and the mixture was stirred at −78° C. for 1 h. A solution of 1-{[2-(2-chlorophenyl)-1-(4-chlorophenyl)-1H-imidazol-4-yl]carbonyl}-4-piperidinone (0.3 g, 0.68 mmol) in THF (1 mL) was added slowly. The mixture was stirred at −78° C. for 2 h and saturated NH$_4$Cl (3 mL) and water added. The mixture was extracted with ethyl acetate (3×20 mL) and dried over MgSO$_4$. The product (0.142 g, 61%) was isolated by column (ethyl acetate). MS (Electrospray) 482 (M)$^+$; $^1$H NMR (300 MHz, CD$_2$Cl$_2$) δ .7.85 (s, 1H), 7.51–7.31 (m, 7H), 7.10–6.98 (m, 4H), 7.17–7.10 (m, 2H), 6.39 (s, 1H), 6.29 (s, 1H), 4.68 (br, 1H), 4.28 (br, 1H), 3.94 (br, 1H), 3.57 (br, 1H), 2.26–1.91 (m, 4H).

Example 19

Preparation of t-butyl 2-hydroxyimino-3-oxobutanoate

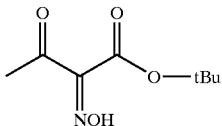

t-Butyl acetoacetate (5.0 g, 31.6 mmol) was dissolved in acetic acid (4.5 mL), cooled by an ice water bath, and treated with sodium nitrite (2.45 g, 35.5 mmol) in water (5.5 mL) while the internal temperature was kept at <10° C. (see, e.g., U.S. Pat. No. 4,743,586). After the addition was complete, the mixture was stirred at rt for 30 minutes before water (16 mL) was added. After 2 h, extraction with ether (3×25 mL), which was washed with water (10 mL), sodium bicarbonate solution (3×10 mL), and water (20 mL), gave t-butyl 2-hydroxyimino-3-oxobutanoate as a white solid (5.52 g, 93%): $^1$H NMR (300 MHz, CDCl$_3$) δ 8.61 (s, 1H), 2.39 (s, 3H), 1.58 (s, 9H).

Example 20

Preparation of t-Butyl 2-(2-chlorophenyl)-5-methyl-1H-imidazole-4-carboxylate

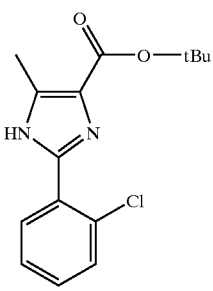

t-Butyl 2-hydroxyimino-3-oxobutanoate (0.50 g, 2.67 mmol) was mixed with 2-chlorobenzylamine (0.34 mL, 2.82 mmol) in anhydrous acetonitrile (10 mL), and heated at reflux for 3 h. Upon cooling, the suspension was filtered, and the filtered material was washed with a small amount of acetonitrile to afford a white solid (0.379 g). The filtrate was concentrated and the residue chromatographed over silica gel (25% EtOAc in hexane) to give t-butyl 2-(2-chlorophenyl)-5-methyl-1H-imidazole-4-carboxylate as a yellow foam (0.262 g, 82% combined yield): $^1$H NMR (300 MHz, CDCl$_3$) δ 10.43 (br, 1H), 8.29 (m, 1H), 7.38 (m, 3H), 2.52 (s, 3H), 1.60 (s, 9H).

Example 21

Preparation of t-Butyl 2-(2-chlorophenyl)-5-methyl-1-(4-nitrophenyl)-1H-imidazole-4-carboxylate

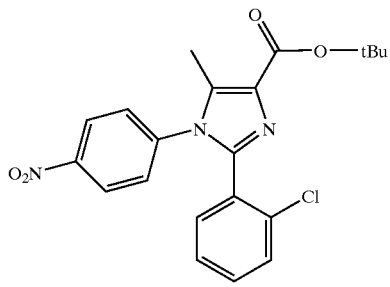

t-Butyl 2-(2-chlorophenyl)-5-methylimidazole-4-carboxylate (70 mg, 0.24 mmol) was mixed with 4-fluoro-1-nitrobenzene (27 µL, 0.25 mmol) and potassium carbonate (66 mg, 0.48 mmol) in dry DMF and heated at 120° C. for 4 h. The mixture was diluted with water and filtered to give a yellow solid which was chromatographed over silica gel (40% EtOAc in hexane) to afford a yellow solid (72 mg, 73%): $^1$H NMR (300 MHz, CDCl$_3$) δ 8.20 (m, 2H), 7.51 (m, 1H), 7.25 (m, 5H), 2.45 (s, 3H), 1.66 (s, 9H).

Example 22

Preparation of 2-(2-chlorophenyl)-5-methyl-1-(4-nitrophenyl)-1H-imidazole-4-carboxylic acid

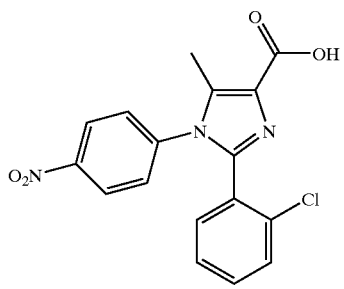

t-Butyl 2-(2-chlorophenyl)-5-methyl-1-(4-nitrophenyl)-1H-imidazole-4-carboxylate (69 mg, 0.17 mmol) was dissolved in dry dichloromethane (2 mL) and treated dropwise with trifluoroacetic acid (2 mL). After stirring at rt for 2 h, the solution was concentrated to give 2-(2-chlorophenyl)-5-methyl-1-(4-nitrophenyl)-1H-imidazole-4-carboxylic acid as a yellow foam, which was used without purification in the preparation of Example 23.

Example 23

Preparation of N-cyclohexyl-2-(2-chlorophenyl)-5-methyl-1-(4-nitrophenyl)-1H-imidazole-4-carboxamide

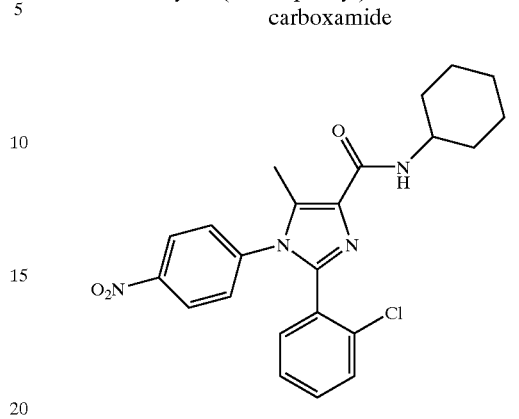

The carboxylic acid obtained from Example 22 was dissolved in dry dichloromethane (3 mL), cooled by an ice water bath, and treated with 1-(3-dimethylamino)propyl-3-ethylcarbodiimide hydrochloride (39 mg, 0.20 mmol) and dimethylaminopyridine (46 mg, 0.38 mmol). The mixture was stirred at rt for 1 h before cyclohexylamine (23 µL, 0.20 mmol) was added. The solution was stirred overnight, diluted with dichloromethane, washed with water and ammonium chloride solution, dried (sodium sulfate), and filtered. The filtrate was concentrated to afford a yellow oil (70 mg) which was chromatographed over silica gel (35% EtOAc in hexane) to give N-cyclohexyl-2-(2-chlorophenyl)-5-methyl-1-(4-nitrophenyl)-1H-imidazole-4-carboxamide as a yellow solid (50 mg, 67%): mp 217–220° C.; $^1$H NMR (300 MHz, CDCl$_3$) δ 8.20 (d, 2H), 7.41 (m, 1H), 7.25 (m, 5H), 7.12 (m, 1H), 3.95 (m, 1H), 2.55 (s, 3H), 2.00 (m, 2H), 1.75 (m, 2H), 1.61 (m, 1H), 1.30 (m, 5H); LC-MS m/z 439.2 (MH$^+$), retention time 3.41 min (method 1).

Example 24

Preparation of tert-butyl 1-(4-chlorobenzyl)-2-(2-chlorophenyl)-5-methyl-1H-imidazole-4-carboxylate

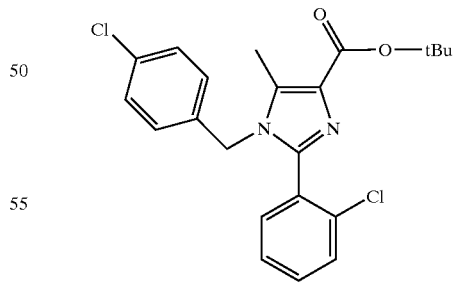

t-Butyl 2-(2-chlorophenyl)-5-methylimidazole-4-carboxylate (70 mg, 0.24 mmol) was mixed with 4-chlorobenzyl bromide (50 mg, 0.24 mmol) and potassium carbonate (66 mg, 0.48 mmol) in dry acetonitrile (3 mL) and heated at reflux overnight. The next day, additional 4-chlorobenzyl bromide (10 mg, 0.05 mmol) was added, and the reaction mixture was again heated at reflux overnight.

The next day, water was added to the cooled mixture, which was subsequently extracted with EtOAc. The extract was washed with aqueous NaCl, dried (NaSO₄), filtered, and concentrated to give a colorless oil (113 mg). It was chromatographed over silica gel (25% EtOAc in hexane) to afford tert-butyl 1-(4-chlorobenzyl)-2-(2-chlorophenyl)-5-methyl-1H-imidazole-4-carboxylate as a white foam (61 mg, 61% yield): $^1$H NMR (300 MHz, CDCl₃) δ 7.48 (d, 1H), 7.40 (m, 1H), 7.27 (m, 2H), 7.17 (d, 2H), 6.78 (d, 2H), 5.33 (br, 2H), 2.55 (s, 3H), 1.50 (s, 9H); LC-MS m/z 417.1 (MH⁺), retention time 3.23 min (method 1).

Example 25

Preparation of ethyl 5-bromo-1-(4-chlorophenyl)-2-(2,4-dimethylphenyl)-1H-imidazole-4-carboxylate

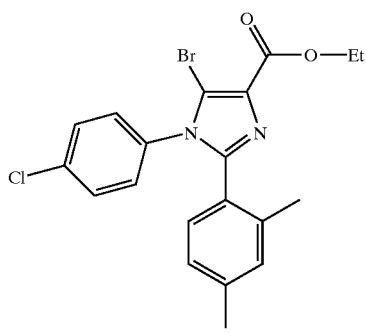

Ethyl 1-(4-chlorophenyl)-2-(2,4-dimethylphenyl)-1H-imidazole-4-carboxylate (1.23 g, 3.47 mmol) was dissolved in EtOH (15 mL) and treated with N-bromosuccinimide (1.25 g, 7.02 mmol). The solution was stirred at rt for 3 h. Water was added. Extraction with dichloromethane, which was then washed with NaCl solution, gave an orange solid (1.94 g). Purification by chromatography over silica gel (20% EtOAc in hexane) afforded a light tan solid (1.028 g, 68%): $^1$H NMR (300 MHz, CDCl₃) δ 7.35 (d, 2H), 7.03 (d, 2H), 7.00 (m, 1H), 6.86 (m, 2H), 4.44 (q, 2H), 2.26 (s, 3H), 2.10 (s, 3H), 1.43 (t, 3H); LC-MS m/z 433.1 (MH⁺), retention time 3.84 min (method 1).

Example 26

Preparation of ethyl 1-(4-chlorophenyl)-5-methyl-2-(2,4-dimethylphenyl)-1H-imidazole-4-carboxylate

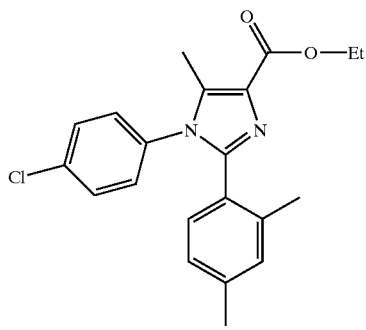

Ethyl 5-bromo-1-(4-chlorophenyl)-2-(2,4-dimethylphenyl)-1H-imidazole-4-carboxylate (430 mg, 0.99 mmol) was dissolved in dry DMF (5 mL) in a pressure tube and treated with tetramethyltin (1.3 mL, 9.38 mmol), palladium acetate (9 mg, 0.04 mmol), and tri-(o-tolyl) phosphine (26 mg, 0.085 mmol). The mixture was heated at 110° C. for 15 minutes. After the mixture was cooled to rt, water was added (25 mL). The mixture was extracted with dichloromethane (2×25 mL), and the organic phase was washed with water, dried (Na₂SO₄), filtered, and concentrated, to give a light brown oil (436 mg). Purification by chromatography over silica gel (33% EtOAc in hexane) afforded ethyl 1-(4-chlorophenyl)-5-methyl-2-(2,4-dimethylphenyl)-1H-imidazole-4-carboxylate as a white foam (338 mg, 93% yield): $^1$H NMR (300 MHz, CDCl₃) δ 7.30 (d, 2H), 7.00 (m, 3H), 6.85 (m, 2H), 4.41 (q, 2H), 2.42 (s, 3H), 2.23 (s, 3H), 2.06 (s, 3H), 1.41 (t, 3H).

Example 27

Preparation of 5-bromo-2-(2-chlorophenyl)-1-(4-chlorophenyl)-N-(1-piperidinyl)-1H-imidazole-4-carboxamide

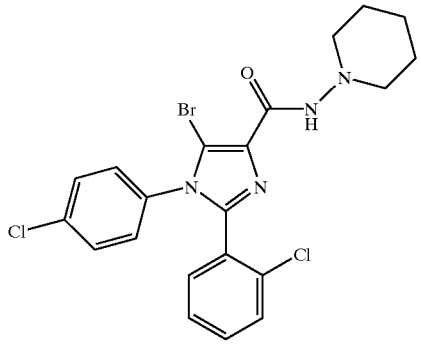

Step 1. A solution of 2-(2-chlorophenyl)-1-(4-chlorophenyl)-1H-imidazole-4-carboxylic acid (50 mg, 0.15 mmol) and N-bromosuccinimide (88 mg, 0.49 mmol) in dimethylformamide (5 mL) was stirred at 75° C. for 3 days. The solution was purified by preparative HPLC to give 5-bromo-2-(2-chlorophenyl)-1-(4-chlorophenyl)-1H-imidazole-4-carboxylic acid as a white solid (30.7 mg, 50%). LC-MS m/z 411.2 (MH⁺), retention time 2.70 min (method 2).

Step 2. As described previously for Example 14, 5-bromo-2-(2-chlorophenyl)-1-(4-chlorophenyl)-1H-imidazole-4-carboxylic acid was converted to 5-bromo-2-(2-chlorophenyl)-1-(4-chlorophenyl)-N-(1-piperidinyl)-1H-imidazole-4-carboxamide. LC-MS m/z 493.0 (MH⁺), retention time 2.63 min (method 2). $^1$H NMR (CD₂Cl₂, 400 MHz) δ 7.29 (m, 6H, Ph), 7.05 (m, 2H, Ph), 3.68 (m, 3H, piperidine), 3.36 (m, 2H, piperidine), 1.88 (m, 3H, piperidine), 1.57 (m, 2H, piperidine).

Example 28

Ethyl 5-chloro-2-(2-chlorophenyl)-1-(4-chlorophenyl)-1H-imidazole-4-carboxylate

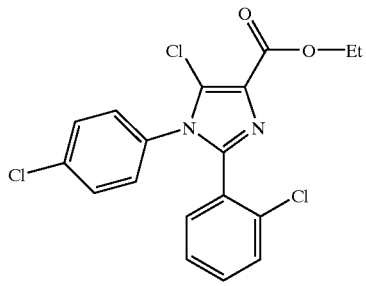

To a solution of ethyl 2-(2-chlorophenyl)-1-(4-chlorophenyl)-1H-imidazole-4-carboxylate (270 mg, 0.75 mmol) in $CH_2Cl_2$ (5 mL) was added $SO_2Cl_2$ (1.6 mL, 20 mmol). The mixture was heated at reflux overnight, and diluted with water. The organic layer was dried over $MgSO_4$, filtered, and concentrated. The residue was purified by flash chromatography over silica gel (33% EtOAc in hexane) to give ethyl 5-chloro-2-(2-chlorophenyl)-1-(4-chlorophenyl)-1H-imidazole-4-carboxylate (60 mg) in 20% yield as a white solid: LC-MS m/z 395.0 ($MH^+$), retention time 3.45 min (method 1). This intermediate, which is an example of Formula X in Scheme 2, was converted into 5-chloro-2-(2-chlorophenyl)-1-(4-chlorophenyl)-N-(1-piperidinyl)-1H-imidazole-4-carboxamide (Table entry 21).

Example 29

Preparation of 2-(2-chlorophenyl)-1-(4-chlorophenyl)-N-methoxy-N-methyl-1H-imidazole-4-carboxamide

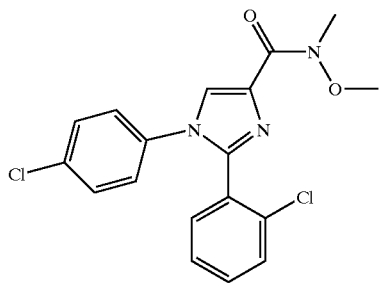

A solution of 2-(2-chlorophenyl)-1-(4-chlorophenyl)-1H-imidazole-4-carbonyl chloride (4.71 g, 13.4 mmol, prepared by the method described in Example 13, step 1) in 10 mL dichloromethane was added to a solution of N,O-dimethylhydroxyamine hydrochloride (1.44 g, 14.7 mmol) and triethylamine (5.6 mL, 40.2 mmol) in 60 mL dichloromethane in an ice water bath under argon with stirring. The bath was removed upon completion of addition. Stirring was continued for 1 h. Water was added and the mixture was extracted with ethyl acetate. The organic layer was dried over $Na_2SO_4$ and concentrated down under reduced pressure. The crude product was purified on silica gel, eluting with ethyl acetate to yield 2-(2-chlorophenyl)-1-(4-chlorophenyl)-N-methoxy-N-methyl-1H-imidazole-4-carboxamide as an off-white solid (4.20 g, 83%): $R_f$=0.22 (ethyl acetate).

Example 30

Preparation of [2-(2-chlorophenyl)-1-(4-chlorophenyl)-1H-imidazol-4-yl](4-fluorophenyl)-methanone

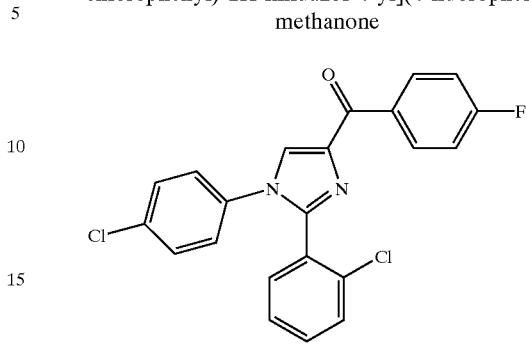

To a solution of 2-(2-chlorophenyl)-1-(4-chlorophenyl)-N-methoxy-N-methyl-1H-imidazole-4-carboxamide (50.0 mg, 0.133 mmol) in 1.5 mL THF was added a 1.0 M solution of 4-fluorophenylmagnesium bromide (0.27 mL, 0.27 mmol) under argon at rt with stirring. The resultant mixture was stirred for 30 minutes and a saturated aqueous solution of $NH_4Cl$ was added. The mixture was extracted with ethyl acetate. The organic layer was dried over $Na_2SO_4$ and concentrated down in vacuo. The crude product was purified on HPLC to give [2-(2-chlorophenyl)-1-(4-chlorophenyl)-1H-imidazol-4-yl](4-fluorophenyl)-methanone as a solid (38.0 mg, 69%): $R_f$=0.58 (1:1 ethyl acetate/hexanes).

Example 31

Preparation of [2-(2-chlorophenyl)-1-(4-chlorophenyl)-5-ethyl-1H-imidazol-4-yl](2-thienyl)-methanone

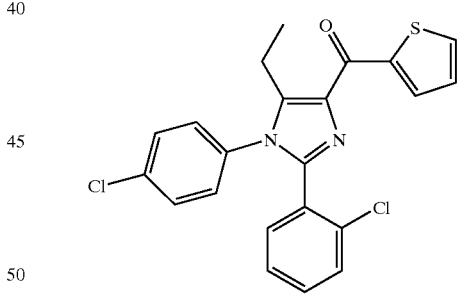

To a solution of 2-bromothiophene (0.22 g, 1.36 mmol) in 2 mL THF was added 0.84 mL of a 1.6 M solution of BuLi in hexane under argon at −78° C. with stirring. The stirring was continued for 1 h. To this was added a solution of 1-{[2-(2-chlorophenyl)-1-(4-chlorophenyl)-5-ethyl-1H-imidazol-4-yl]carbonyl}-4-piperidinone in 2 mL THF. The resultant mixture was stirred and gradually allowed to warm up to rt overnight. The reaction was quenched with saturated aqueous $NH_4Cl$ and the mixture was extracted with ethyl acetate. The organic layer was concentrated and the crude product was purified by HPLC to yield [2-(2-chlorophenyl)-1-(4-chlorophenyl)-5-ethyl-1H-imidazol-4-yl](2-thienyl)-methanone as a solid (60 mg, 31%): $R_f$=0.13 (1:5 ethyl acetate/hexanes).

Example 32

Preparation of 2-(2-chlorophenyl)-1-(4-chlorophenyl)-1H-imidazole-4-carboxaldehyde

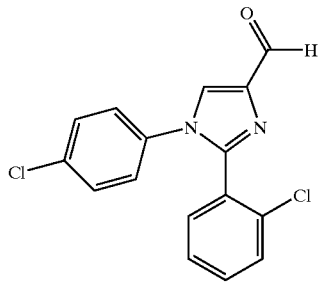

To a solution of ethyl 2-(2-chlorophenyl)-1-(4-chlorophenyl)-1H-imidazole-4-carboxylate (200 mg, 0.51 mmol) in toluene (10 mL) at −78° C. was added DIBAH (2.0 mL) in toluene dropwise. The resulting solution was stirred at rt, quenched with 1N HCl (0.5 mL). The organic layer was washed with 1N HCl (5 mL), dried over MgSO$_4$, filtered, and concentrated. The residue was purified by flash chromatography (50% EtOAc in hexane) to give the product (62 mg, 38% yield). LC-MS m/z 317.0 (MH$^+$), retention time: 2.75 min (method 1).

Example 33

Preparation of N-{[2-(2-chlorophenyl)-1-(4-chlorophenyl)-1H-imidazol-4-yl]methyl}-N-cyclohexylamine

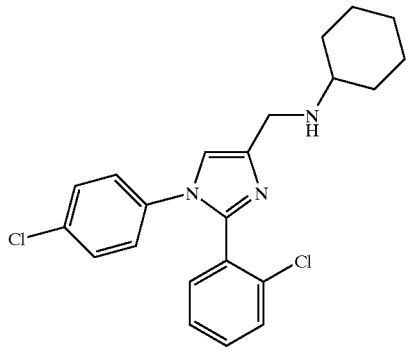

To a solution of 2-(2-chlorophenyl)-1-(4-chlorophenyl)-1H-imidazole-4-carboxaldehyde (62 mg, 0.20 mmol) in methanol (7 mL) was added cyclohexylamine (58 μL, 0.5 mmol). The mixture was stirred overnight, and cooled to 4° C. NaBH$_4$ (40 mg, 1.1 mmol) was added. The mixture was stirred at rt for 1 h, and concentrated. The residue was dissolved in CH$_2$Cl$_2$, washed with brine, dried over MgSO$_4$, filtered, and concentrated. The residue was purified by preparative TLC (50% EtOAc in hexane) to give N-{[2-(2-chlorophenyl)-1-(4-chlorophenyl)-1H-imidazol-4-yl]methyl}-N-cyclohexylamine (65 mg, 81% yield): LC-MS m/z (400.7 MH$^+$), retention time 2.32 min (method 1).

Example 34

Preparation of 1-{[1-(4-chlorophenyl)-2-(2,4-dichlorophenyl)-1H-imidazol-4-yl]methyl}-4-(4-methylphenyl)piperazine To a suspension of lithium aluminum hydride (21 mg, 0.54 mmol) in THF (2 mL), 1-(4-methylphenyl)piperazine hydrochloride (32 mg, 0.13 mmol) was added. After 10 minutes, a solution of ethyl 2-(2,4-dichlorophenyl)-1-(4-chlorophenyl)-1H-imidazole-4-carboxylate (39 mg, 0.1 mmol) in THF (2 mL) was added dropwise. The reaction mixture was stirred for 10 minutes, and diluted by water. The organic layer was dried over MgSO$_4$, filtered, and concentrated. The residue was purified by HPLC (YMC-packed Pro C18 20×150 mm column, 10–90% CH$_3$CN in H$_2$O/TFA, 25 mL/min) to give the product 1-{[1-(4-chlorophenyl)-2-(2,4-dichlorophenyl)-1H-imidazol-4-yl]methyl}-4-(4-methylphenyl)-piperazine (1.4 mg, 2% yield): LC-MS m/z 511.1 (MH$^+$), retention time 2.94 min (method 1). $^1$H NMR (300 MHz, CDCl$_3$) δ: 2.29 (3H, s), 3.42–3.49 (8H, br), 4.39 (2H, s), 6.85–7.41 (11H, m), 7.54 (1H, s).

Other Procedures

In certain cases, the products and intermediates prepared by the experimental methods described in Examples 1–34 were converted into additional products, by applying the appropriate additional chemical steps. These additional examples are described below.

Example 35

1-(4-chlorophenyl)-2-(2,4-dichlorophenyl)-N-[(1R,2R)-2-hydroxycyclohexyl]-1H-imidazole-4-carboxamide

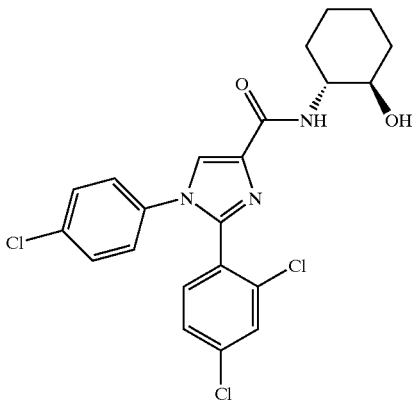

To a solution of N-[(1R, 2R)-2-(benzyloxy)cyclohexyl]-1-(4-chlorophenyl)-2-(2,4-dichlorophenyl)-1H-imidazole- 4-carboxamide (Table entry 278, prepared according to the procedures described in Examples 13 and 14) (100 mg, 0.18 mmol) in CH$_2$Cl$_2$ (2 mL), TMSI (iodotrimethylsilane) (60 µL, 0.42 mmol) was added. The mixture was stirred at rt overnight, and diluted with water. The organic layer was dried over MgSO$_4$, filtered, and concentrated. The residue was purified by preparative TLC (EtOAc) to afford 1-(4-chlorophenyl)-2-(2,4-dichlorophenyl)-N-[(1R,2R)-2-hydroxycyclohexyl]-1H-imidazole-4-carboxamide (56 mg, 67% yield) as a yellow solid: LC-MS m/z 464.3 (MH$^+$), retention time 3.19 min (method 1); R$_f$=0.67 (EtOAc); $^1$H NMR (300 MHz, CDCl$_3$) δ 1.16–1.30 (4H, m), 1.66–1.69 (2H, m), 1.98–2.02 (2H, m), 3.37–3.39 (1H, m), 3.70–3.80 (1H, m), 3.99–4.06 (1H, m), 6.96–7.37 (8H, m), 7.78 (1H, s).

Example 36

1-(4-chlorophenyl)-2-(2,4-dichlorophenyl)-N-[(1S, 2S)-2-hydroxycyclopentyl]-1H-imidazole-4-carboxamide

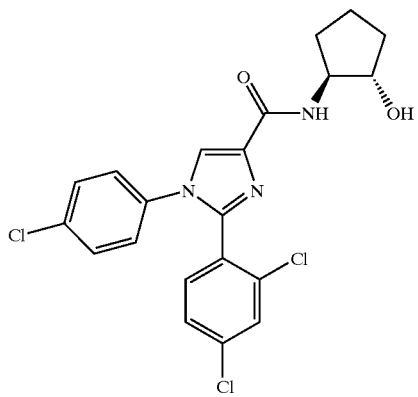

To a solution of N-[(1S, 2S)-2-(benzyloxy)cyclopentyl]-1-(4-chlorophenyl)-2-(2,4-dichlorophenyl)-1H-imidazole-4-carboxamide (Table entry 282, prepared according to the procedures described in Examples 13 and 14) (119 mg, 0.22 mmol) in CH$_2$Cl$_2$ (4 mL), TMSI (0.2 mL, 1.4 mmol) was added. The mixture was stirred at rt overnight, and diluted by water. The organic layer was dried over MgSO$_4$, filtered, and concentrated. The residue was purified by preparative TLC (EtOAc) to afford 1-(4-chlorophenyl)-2-(2,4-dichlorophenyl)-N-[(1S, 2S)-2-hydroxycyclopentyl]-1H-imidazole-4-carboxamide (80 mg, 82% yield) as a white foam: LC-MS m/z 450.0 (MH$^+$), retention time 3.24 min (method 1); Rf=0.45 (50% EtOAc in hexane); $^1$H NMR (300 MHz, CDCl$_3$) δ 1.22–2.24 (6H, m), 3.97–4.15 (2H, m), 7.03–7.42 (7H, m), 7.86 (1H, s).

Example 37

2-(2-chlorophenyl)-1-(4-chlorophenyl)-N-(4-piperidinyl)-1H-imidazole-4-carboxamide

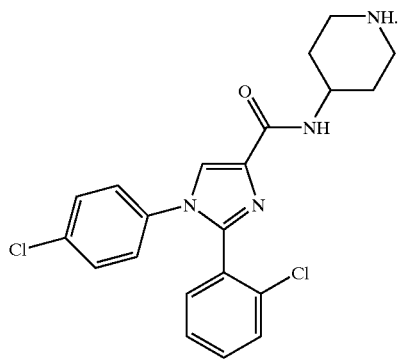

To a solution of ethyl 4-({[2-(2-chlorophenyl)-1-(4-chlorophenyl)-1H-imidazol-4-yl]carbonyl}amino)-1-piperidinecarboxylate (Table entry 221) (0.595 g, 1.221 mmol) in CH$_2$Cl$_2$ (10 mL) was added TMSI (0.176 mL, 2.7 mmol). The mixture was heated at reflux for 3 h, diluted by methanol, and concentrated. The residue was dissolved in methanol and NaOMe (0.62 mmol) was added. The mixture was concentrated and purified by flash chromatography (2M NH$_3$ in methanol:EtOAc=15:85) to afford the product 2-(2-chlorophenyl)-1-(4-chlorophenyl)-N-(4-piperidinyl)-1H-imidazole-4-carboxamide (180 mg, 36% yield): LC-MS m/z 415.3 (MH$^+$), retention time 2.22 min (method 1); Rf=0.25 (1:1 EtOAc/2M NH$_3$ in MeOH). $^1$H NMR (300 MHz, CDCl$_3$) δ 1.35–1.51 (2H, m), 1.91–2.15 (3H, br), 2.63–2.78 (2H, m), 3.03–3.09 (2H, m), 3.97–4.15 (1H, m), 6.96–7.52 (8H, m), 7.81 (1H, s).

Example 38

2-(2-Chlorophenyl)-1-(4-chlorophenyl)-N-[1-(2-pyridinyl)-4-piperidinyl]-1H-imidazole-4-carboxamide

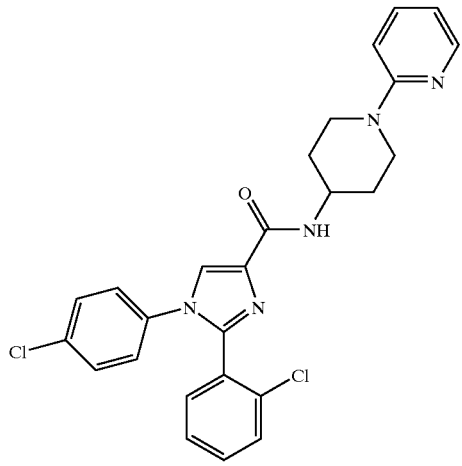

A flask was charged with 2-(2-chlorophenyl)-1-(4-chlorophenyl)-N-(4-piperidinyl)-1H-imidazole-4-carboxamide (Example 37) (100 mg, 0.24 mmol), 2-bromopyridine (0.55 mg, 0.22 mmol), Pd$_2$(dba)$_3$ (38 mg, 0.24 mmol), BINAP (1.18 mg, 0.0019 mmol), NaOtBu (33.6 mg, 0.35 mmol), and toluene (2 mL). The reaction mixture was heated at reflux overnight, cooled to rt, and diluted with CH$_2$Cl$_2$. The solid was filtered off. The solvent was evaporated. The residue was purified by flash chromatography (33% EtOAc in hexane) to give the product 2-(2-chlorophenyl)-1-(4-chlorophenyl)-N-[1-(2-pyridinyl)-4-piperidinyl]-1H-imidazole-4-carboxamide (55 mg, 47% yield): LC-MS m/z 492.1 (MH$^+$), retention time 2.47 min (method 1); Rf=0.33 (50% EtOAc in hexane).

Example 39

2-(2-chlorophenyl)-1-(4-chlorophenyl)-N-(1-methyl-4-piperidinyl)-1H-imidazole-4-carboxamide

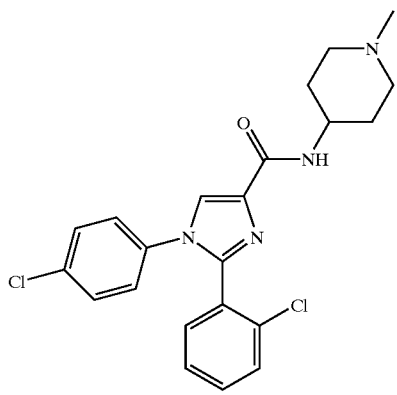

To a solution of 2-(2-chlorophenyl)-1-(4-chlorophenyl)-N-(4-piperidinyl)-1H-imidazole-4-carboxamide (Example 37) (80 mg, 0.2 mmol) in CH$_2$Cl$_2$ (6 mL) was added CH$_3$I (28.4 mg, 0.2 mmol) and Et$_3$N (0.031 mL, 0.22 mmol). The reaction mixture was heated at reflux for 5 h, cooled to rt, and washed with brine. The organic layer was dried over MgSO$_4$, filtered, and concentrated. The residue was purified by flash chromatography (2M NH$_3$ in methanol:EtOAc= 1:10) to afford the product 2-(2-chlorophenyl)-1-(4-chlorophenyl)-N-(1-methyl-4-piperidinyl)-1H-imidazole-4-carboxamide (24 mg, 28% yield): LC-MS m/z 429.1 (MH$^+$), retention time 2.27 min (method 1); Rf=0.31 (EtOAc: 2M NH$_3$ in MeOH=9:1).

Example 40

2-(2-chlorophenyl)-1-(4-chlorophenyl)-N-[trans-2-(2-hydroxyethoxy)cyclohexyl]-1H-imidazole-4-carboxamide

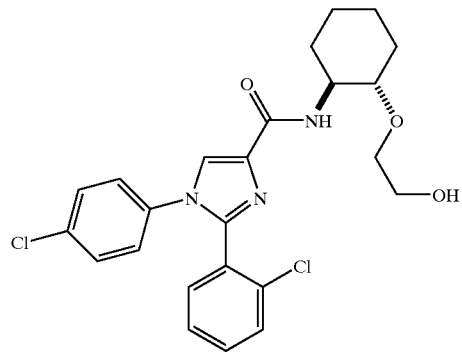

To a solution of 2-{[trans-2-({[2-(2-chlorophenyl)-1-(4-chlorophenyl)-1H-imidazol-4-yl]carbonyl}amino)cyclohexyl]oxy}-ethyl acetate (Table entry 286) (31 mg, 0.06 mmol) in THF (7 mL) and water (0.7 mL) was added NaBH$_4$ (5 mg, 0.13 mmol) portionwise over 1 h with the temperature kept below 20° C. The mixture was stirred at rt overnight, cooled to 5° C., treated with acetone (1 mL), and then concentrated. The residue was dissolved in CH$_2$Cl$_2$ and washed with brine. The organic layer was dried over MgSO$_4$, filtered, and concentrated. The residue was purified by flash chromatography (2.5% methanol in EtOAc) to give the product 2-(2-chlorophenyl)-1-(4-chlorophenyl)-N-[(1R,2S)-2-(2-hydroxyethoxy)cyclohexyl]-1H-imidazole-4-carboxamide (7.5 mg, 26% yield): LC-MS m/z (474.8 MH$^+$), retention time 2.91 min (method 1); Rf=0.17 (EtOAc).

Example 41

2-(2-chlorophenyl)-1-(4-chlorophenyl)-N-[trans-2-methoxycyclohexyl]-1H-imidazole-4-carboxamide

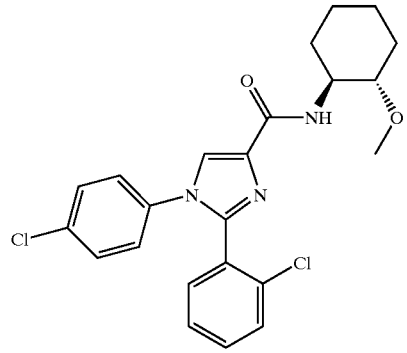

A flask was charged with 2-(2-chlorophenyl)-1-(4-chlorophenyl)-N-[trans-2-hydroxycyclohexyl]-1H-imidazole-4-carboxamide (Table entry 336) (35 mg, 0.1 mmol), benzene (3 mL), 50% aqueous NaOH (2.5 mL), and Bu$_4$NHSO$_4$ (17 mg). While the mixture was stirred vigorously at 10° C., CH$_3$I (19 μL, 0.3 mmol) was added dropwise rapidly. The mixture was stirred for another 30 minutes, and diluted with water (5 mL) and hexane (10 mL). The organic layer was dried over MgSO$_4$, filtered, and concentrated. The residue was purified by flash chromatography (75% EtOAc in hexane) to give the product 2-(2-chlorophenyl)-1-(4-chlorophenyl)-N-[(1R,2S)-2-methoxycyclohexyl]-1H-imidazole-4-carboxamide (23 mg, 63% yield): LC-MS m/z 444.2 (MH$^+$), retention time 3.24 min (method 1).

Example 42

4-{[2-(2-chlorophenyl)-1-(4-chlorophenyl)-1H-imidazol4-yl]carbonyl}thiomorpholine 1-oxide

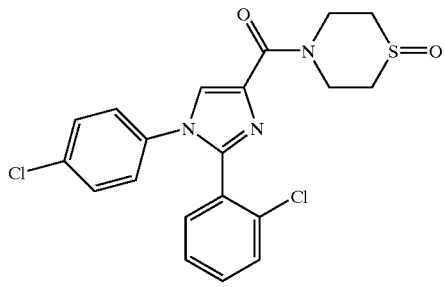

To a solution of 4-{[2-(2-chlorophenyl)-1-(4-chlorophenyl)-1H-imidazol-4-yl]carbonyl}thiomorpholine (Table entry 176) (30 mg, 0.072 mmol) in acetone (2 mL), was added 30% aqueous H$_2$O$_2$ (0.09 mmol). The resulting solution was stirred at rt for 36 h, diluted with water, neutralized with NaHCO$_3$, and extracted with CH$_2$Cl$_2$. The organic layer was dried over MgSO$_4$, filtered, and concentrated. The residue was purified by flash chromatography (20% MeOH in EtOAc) to give the product 4-{[2-(2-chlorophenyl)-1-(4-chlorophenyl)-1H-imidazol-4-yl]carbonyl}thiomorpholine 1-oxide (17 mg, 54% yield): LC-MS m/z 434.5 (MH$^+$), retention time 2.55 min (method 1); Rf=0.47 (17% EtOAc in hexane).

Example 43

N-[(1S,2S)-2-(benzyloxy)cyclohexyl]-5-bromo-2-(2-chlorophenyl)-1-(4-chlorophenyl)-1H-imidazole-4-carboxamide

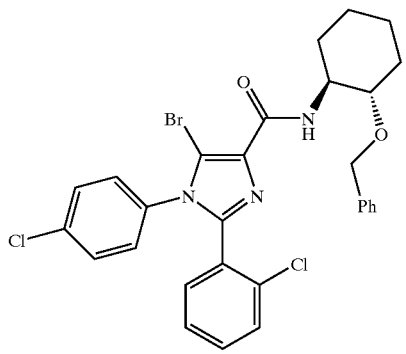

A solution of N-[(1S,2S)-2-(benzyloxy)cyclohexyl]-2-(2-chlorophenyl)-1-(4-chlorophenyl)-1H-imidazole-4-carboxamide (Table entry 276) (198 mg, 0.380 mmol) and N-bromosuccinimide (88 mg, 0.49 mmol) in dimethylformamide (5 mL) was stirred at 75° C. for 3 days. The solution was purified by preparative HPLC to give N-[(1S,2S)-2-(benzyloxy)cyclohexyl]-5-bromo-2-(2-chlorophenyl)-1-(4-chlorophenyl)-1H-imidazole-4-carboxamide as a white solid (196 mg, 86%). LC-MS m/z 598.1 (MH$^+$), retention time 3.72 min (method 2).

Example 44

5-Bromo-2-(2-chlorophenyl)-1-(4-chlorophenyl)-N-[(1S,2S)-2-hydroxycyclohexyl]-1H-imidazole-4-carboxamide

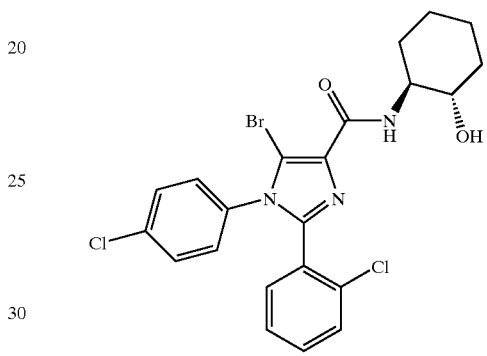

As described previously for Example 35, N-[(1S,2S)-2-(benzyloxy)cyclohexyl]-5-bromo-2-(2-chlorophenyl)-1-(4-chlorophenyl)-1H-imidazole-4-carboxamide (Example 43) was de-benzylated by treatment with iodotrimethylsilane to give 5-bromo-2-(2-chlorophenyl)-1-(4-chlorophenyl)-N-[(1S,2S)-2-hydroxycyclohexyl]-1H-imidazole-4-carboxamide. LC-MS m/z 508.1 (MH$^+$), retention time 2.96 min (method 2). $^1$H NMR (CD$_2$Cl$_2$, 400 MHz) δ 7.43 (d, 1H, Ph), 7.27 (m, 5H, Ph), 7.06 (m, 2H, Ph), 3.70 (m, 1H, CHOH), 3.44 (m, 1H, CHN), 1.95 (m, 2H, cyclohexane), 1.64 (m, 2H, cyclohexane), 1.24 (m, 4H, cyclohexane).

Example 45

1-(4-Aminophenyl)-2-(2-chlorophenyl)-5-methyl-N-(1-piperidinyl)-1H-imidazole-4-carboxamide

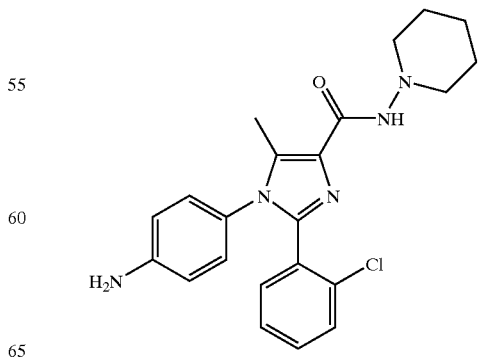

A sample of 2-(2-chlorophenyl)-5-methyl-1-(4-nitrophenyl)-N-(1-piperidinyl)-1H-imidazole-4-carboxamide (Table entry 41) (111 mg, 0.25 mmol) was added as a suspension in ethanol (5 mL) to Degussa-type palladium on carbon (10% by weight, 12 mg). The mixture was hydrogenated at atmospheric pressure and rt for 2 h. Filtration of the mixture through Celite and concentration of the filtrate gave 1-(4-aminophenyl)-2-(2-chlorophenyl)-5-methyl-N-(1-piperidinyl)-1H-imidazole-4-carboxamide as a yellow foam (104 mg, 100%). This material was used without purification for the preparation of compounds of the invention, such as Example 46.

Example 46

2-(2-chlorophenyl)-1-(4-{[(ethylamino)carbonyl]amino}phenyl)-5-methyl-N-(1-piperidinyl)-1H-imidazole-4-carboxamide trifluoroacetate

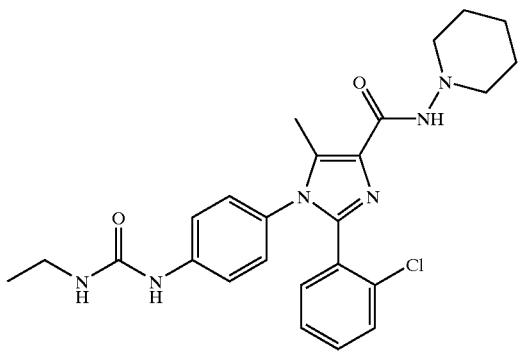

1-(4-Aminophenyl)-2-(2-chlorophenyl)-5-methyl-N-(1-piperidinyl)-1H-imidazole-4-carboxamide (Example 45) (52 mg, 0.13 mmol) was dissolved in dry dichloromethane (2 mL) and added to ethyl isocyanate (20 µL, 0.25 mmol). The solution was stirred at rt for 6 h before more ethyl isocyanate (30 µL, 0.38 mmol) was added. After stirring overnight, the mixture was heated at reflux for 1 h. The solvent was evaporated to give a yellow solid which was chromatographed over silica gel (3% MeOH in EtOAc) to afford semi-pure product (21 mg). This material was further purified by HPLC (YMC-packed Pro C18 15×200 mm column, 30–90% CH$_3$CN in H$_2$O/TFA, 20 mL/min.) to give 2-(2-chlorophenyl)-1-(4-{[(ethylamino)carbonyl]amino}phenyl)-5-methyl-N-(1-piperidinyl)-1H-imidazole-4-carboxamide trifluoroacetate as a white solid (12 mg, 13% yield): LC-MS m/z 481.4 (MH$^+$), retention time 2.35 min (method 1).

Example 47

1-[4-(acetylamino)phenyl]-2-(2-chlorophenyl)-5-methyl-N-(1-piperidinyl)-1H-imidazole-4-carboxamide

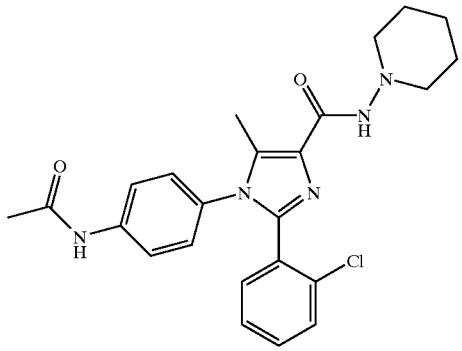

1-(4-Aminophenyl)-2-(2-chlorophenyl)-5-methyl-N-(1-piperidinyl)-1H-imidazole-4-carboxamide (Example 45) (51 mg, 0.12 mmol) was dissolved in dry dichloromethane (2 mL) and treated with acetic anhydride (14 µL, 0.15 mmol) dropwise. The solution was stirred at rt for 4 h, and then the solvent was evaporated to give an amber oil. It was purified by HPLC (YMC-packed Pro C18 15×200 mm column, 30–90% CH$_3$CN in H$_2$O/TFA, 20 mL/min.) to afford an off-white solid (13 mg, 15%): LC-MS m/z 452.3 (MH$^+$), retention time 2.31 min (method 1).

Example 48

2-(2-Chlorophenyl)-5-methyl-1-{4-[(methylsulfonyl)amino]phenyl}-N-(1-piperidinyl)-1H-imidazole-4-carboxamide trifluoroacetate

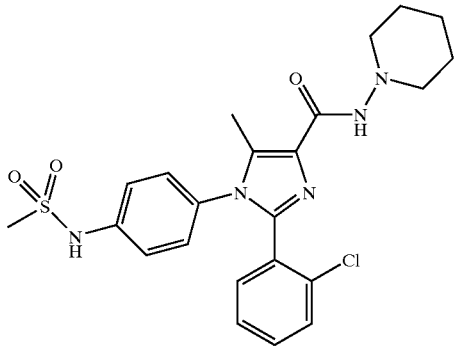

1-(4-Aminophenyl)-2-(2-chlorophenyl)-5-methyl-N-(1-piperidinyl)-1H-imidazole-4-carboxamide (Example 45) (52 mg, 0.13 mmol) was dissolved in dry dichloromethane (2 mL), cooled by an ice water bath, and the mixture was then treated with methanesulfonyl chloride (12 µL, 0.16 mmol) and triethylamine (21 µL, 0.15 mmoL). The solution was stirred at rt overnight, and then the solvent was evaporated. The residue was purified by HPLC (YMC-packed Pro C18 15×200 mm column, 30–90% CH$_3$CN in H$_2$O/TFA, 20 mL/min.) to afford a light tan solid (21 mg, 27%): LC-MS m/z 488.4 (MH$^+$), retention time 2.29 min (method 1).

Example 49

1-{[1-(4-Chlorophenyl)-2-(2-methylphenyl)-1H-imidazol-4-yl]carbonyl}-4-phenyl-1,2,3,6-tetrahydropyridine

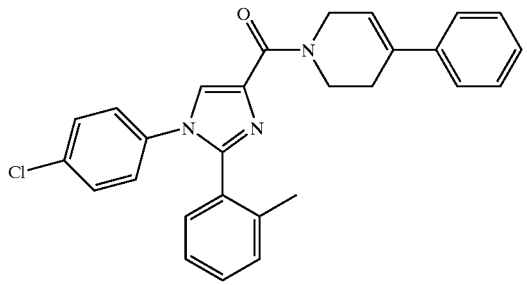

A 30-mg sample of 1-{[2-(2-methylphenyl)-1-(4-chlorophenyl)-1H-imidazol-4-yl]carbonyl}-4-phenyl-4-piperidinol (Table entry 414), was dissolved in 20 mL dichloromethane, and then 5 mL 2M HCl in ether was added to the solution. Evaporation of the solvent at high temperature (ca. 70° C., 16 hr) in a multiple sample evaporator (GeneVac) gave 1-{[1-(4-chlorophenyl)-2-(2-methylphenyl)-1H-imidazol-4-yl]carbonyl}-4-phenyl-1,2,3,6-tetrahydropyridine (yellow solid). $^1$H NMR (400 MHz, CD$_3$COCD$_3$) δ 8.31 (s, 1H), 7.05–7.35 (m, 13 H), 6.05 (s, 1 H), 4.2 (m, 2 H), 3.85 (m, 2H), 2.5 (m, 2H), 2.0 (s, 3H); LC-MS m/z 454 (MH$^+$), retention time 2.92 min (method 2).

Preparation of Intermediates

Experimental procedures for the preparation of chemical reagents that are not commercially available are described below.

Intermediate A
Ethyl 3-bromo-2-oxobutanoate

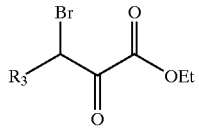

This bromo pyruvate was prepared by oxidative bromination of the corresponding hydroxyesters, by the procedure described by Plouvier et al., (Heterocycles 32:693–701, 1991). In a similar manner, ethyl 3-bromo-2-oxopentanoate and ethyl 3-bromo-2-oxohexanoate were prepared.

Intermediate B
Ethyl 3-bromo-3-cyclopropyl-2-oxopropanoate

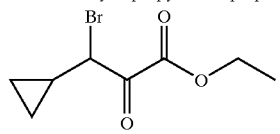

The procedure was similar to that reported in the literature (see, e.g., J. Org. Chem. 37, 505–506, 1972).

Step 1. To a solution of BF$_3$.Et$_2$O (57.5 mL, 0.454 mmol) in CHCl$_3$ (180 mL) heated at reflux was added dropwise, over a 1-h period, a solution of 1,3-propanedithiol (22.7 mL, 0.227 mmol), followed by ethyl diethoxyacetate (40 g, 0.227 mmol) in CHCl$_3$ (40 mL). The resulting mixture was heated for 30 minutes, and then cooled to rt. The cooled solution was washed 2 times with water, once with saturated aqueous NaHCO$_3$, and then re-washed with water. The combined organic phases were dried over MgSO$_4$, then evaporated to give 41 g (94%) of ethyl 1,3-dithiane-2-carboxylate as a yellow oil, which was used in the next step without purification. $^1$H NMR (CDCl$_3$): δ 4.24 (2H, q, J=7.2 Hz), 4.17 (1H, s), 3.46–3.39 (2H, m), 2.64–2.58 (2H, m), 2.18–2.01 (2H, m), 1.30 (3H, t, J=7.2 Hz).

Step 2. To a suspension of NaH (95%, 2.8 g, 111 mmol) in dry toluene (120 mL) stirring at 0° C. was dropwise added, over 10 minutes, a solution of bromomethylcyclopropane (15 g, 111 mmol), and ethyl 1,3-dithiane-2-carboxylate (17.77 g, 92.58 mmol) in dry DMF (40 mL). The ice bath was removed and the solution was stirred overnight at rt. Water was added to the solution and the phases were separated. The organic phase was dried over MgSO$_4$, then evaporated to give 19.6 g (50%) of ethyl 2-(cyclopropylmethyl)-1,3-dithiane-2-carboxylate, which was used in the next step without purification. $^1$H NMR (CDCl$_3$): δ 4.26 (2H, q, J=7.2 Hz), 3.30–3.23 (2H, m), 2.69–2.64 (2H, m), 2.16–2.11 (1H, m), 1.96 (2H, d, J=6.8 Hz), 1.91–1.81 (1H, m), 1.34 (3H, t, J=7.2 Hz), 0.93–0.86 (1H, m), 0.52–0.47 (2H, m), 0.20–0.16 (2H, m).

Step 3. A solution of ethyl 2-(cyclopropylmethyl)-1,3-dithiane-2-carboxylate (19.6 g, 79.67 mmol) in CH$_3$CN (20 mL) was slowly added, over 30 minutes, to a well-stirred suspension of NBS (N-bromosuccinimide) in CH$_3$CN (210 mL) and water (55 mL). After the mixture was stirred for 1 h, the resulting red solution was poured into an ice-cold CH$_2$Cl$_2$-Hexane solution (1:1 500 mL). The resulting mixture was washed with saturated aqueous NaHSO$_3$ and water. The colorless organic phase was carefully washed with saturated aqueous K$_2$CO$_3$ and water. The organic phase was dried over MgSO$_4$, then evaporated to give 6.88 g (55%) of ethyl 3-cyclopropyl-2-oxopropanoate as a yellow oil. $^1$H NMR (CDCl$_3$): δ 4.29 (2H, q, J=8 Hz), 2.71 (2H, d, J=9 Hz), 1.35 (3H, t, J=8 Hz), 1.05–0.98 (1H, m), 0.59–0.54 (2H, m), 0.17–0.14 (2H, m).

Step 4. To a solution of ethyl 3-cyclopropyl-2-oxopropanoate (4.75 g, 30.44 mmol) in CCl$_4$ (60 mL) at rt was added NBS (5.96 g 33.49 mmol). The resulting mixture was heated at reflux overnight, then cooled, filtered, and evaporated to provide ethyl 3-bromo-3-cyclopropyl-2-oxopropanoate; $^1$H NMR (CDCl$_3$): δ 4.46–4.32 (3H, m), 1.41 (3H, t, J=8 Hz), 0.96–0.86 (1H, m), 0.55–0.50 (2H, m), 0.07–0.03 (2H, m). This compound was used without purification for the preparation of compounds of the invention such as 1-(4-chlorophenyl)-2-(2-chlorophenyl)-N-(1-piperidinyl)-5-cyclopropyl-1H-imidazole-4-carboxamide hydrochloride (Table entry 22). In a similar manner, ethyl 3-bromo-3-cyclobutyl-2-oxopropanoate and ethyl 3-bromo-3-isobutyl-2-oxopropanoate were prepared.

Intermediate C
Ethyl 3-bromo-2-oxoheptanoate

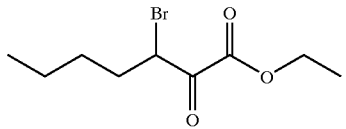

Step 1. To a suspension of LiI (23.61 g, 176.44 mmol) in THF (200 mL) at rt was slowly added Cu$_2$Br$_2$ (25.30 g, 88.22 mmol). A vigorous exothermic reaction occurred, and the mixture was then cooled to −78° C. Pentylmagnesium bromide (2M, 36.76 mL, 88.22 mmol) was slowly added at −78° C., and followed soon after by ethyl chloro(oxo)acetate (10 g, 73.52 mmol). The resulting solution was stirred 10 minutes at −78° C., then quenched by dropwise addition of water. The mixture was allowed to warm to rt, and then the organic phase was separated, dried (MgSO4), and evaporated. Purification by flash chromatography using 9:1 hexane/EtOAc as eluant gave ethyl 2-oxoheptanoate as a colorless oil (3.0 g, 23%). $^1$NMR (400 MHz, CDCl$_3$) δ 4.33–4.21 (m, 2 H), 2.82 (m, 2 H), 1.63–1.59 (m, 2 H), 1.63–11.19 (m, p H), 0.9–0.83 (m, 3 H), LC-MS m/z 279.21 (MH$^+$), retention time 2.42 min (method 2).

Step 2. To a cold solution of ethyl 2-oxoheptanoate (2 g, 11.62 mmol) in AcOH (20 mL), was added Br$_2$ (596 μL, 11.62 mmol). The mixture was stirred 20 minutes at 0° C., then the mixture was allowed to warm to rt. After the mixture was stirred for 3 h, water and CH$_2$Cl$_2$ were added. The organic phase was separated, dried (MgSO$_4$), and evaporated to give crude ethyl 3-bromo-2-oxoheptanoate as a dark oil; $^1$H NMR (400 MHz, CDCl$_3$) δ 5.05–5.01 (m, 1 H), 4.45–4.20 (m, 2 H), 2.18–1.94 (m, 2 H), 1.74–1.57 (m, 2 H), 1.48–1.17 (m, 5 H), 0.95–0.82 (m, 3 H). This compound was used without purification for the preparation of compounds of the invention such as 1-(4-chlorophenyl)-2-(2-chlorophenyl)-N-(1-piperidinyl)-5-butyl-1H-imidazole-4-carboxamide hydrochloride (Table entry 20).

Intermediate D
4-Piperidinone trifluoroacetate

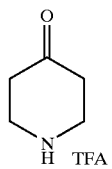

A suspension of t-butyl 4-oxo-1-piperidine carboxylate (10 g, 0.05 mol) in trifluoroacetic acid (10 mL) was stirred rt overnight and concentrated to give a pale yellow solid (11.26 g, crude). MS (Electron spray) 100 (MH$^+$), free amine; $^1$H NMR (300 MHz, CD$_3$OD) δ 3.27–3.12 (m, 4H), 2.01–1.86 (m, 4H).

Intermediate E
trans-1-Amino-2-hydroxyindan

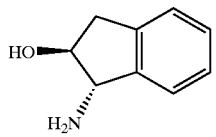

This compound was prepared as described by Thompson et al., (J. Med. Chem. 35:1685–1701, 1992). To 1 liter of 12 N NH$_4$OH cooled to 0° C. was added 50 g (0.235 mol) of 2-bromo-1-indanol. After stirring for 30 minutes, the mixture was allowed to warm, and then stirred for 24 hours. The mixture was concentrated under reduced pressure to remove excess ammonia and then allowed to stand open at rt overnight. The mixture was made basic (pH>10) by addition of 20% KOH, cooled in an ice bath, and filtered. After the residue was dried in a vacuum oven at 60° C. overnight, the desired product was obtained as a tan solid (24 g, 69%).

Intermediate F
cis-1-Hydroxy-2-aminoindan

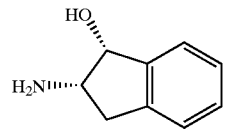

Following the procedure described in Tetrahedron: Asymmetry 7:1559–1562, 1996, trans-2-bromo-1-indanol (500 mg, 2.35 mmol) was dissolved in DMF (5 mL) and sodium azide (305 mg, 4.69 mmol) was added dropwise. The mixture was stirred at rt for 1 h, and then heated to 70° C. and stirred for an additional 18 h. The mixture was cooled, water was added, and extracted with ether. The ether was removed and the crude (412 mg) was dissolved in THF (15 mL). This solution was added to Pd/C (41 mg) and stirred under hydrogen at rt for 3 days. The reaction mixture was filtered and the filtrate was concentrated down to provide the desired product, which was used without purification.

Intermediate G
trans-1-Amino-2-hydroxy-1,2,3,4-tetrahydronaphthalene

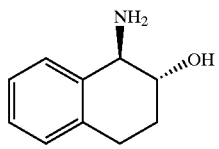

This compound was prepared from dihydronaphthalene according to the procedures described by Bellucci et al., (Tetrahedron: Asymmetry 8:895–902, 1997).

Intermediate H
trans-(2R,3R)-3-[(2,4-Dimethoxybenzyl)amino]-1,2,3,4-tetrahydro-2-naphthalenol

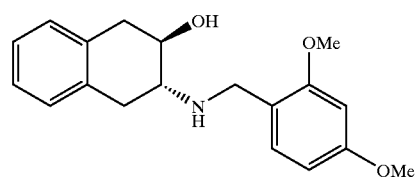

This compound was prepared by following the procedure described by Efange et al., (J. Med. Chem. 40:3905–3914, 1997).

Intermediate I
(1S,2R,3R)-3-Amino-1,7,7-trimethylbicyclo[2.2.1]heptan-2-ol

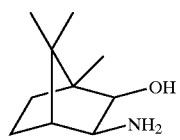

This compound, and its enantiomer, were obtained by LiAlH$_4$ reduction of the respective camphorquinone 3-oximes, by the procedure described by Gawley and Zhang, (J. Org. Chem. 61:8103–8112, 1996).

Intermediate J
Ethyl [(trans-2-aminocyclohexyl)oxy]acetate

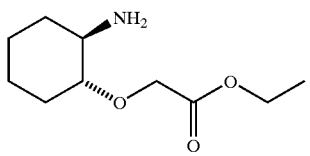

To a solution of trans-2-amino-cyclohexanol hydrochloride (455 mg, 3.0 mmol) in THF (7 mL) was added sodium hydride (78 mg, 3.25 mmol) under argon. The mixture was stirred at rt for 12 h before ethyl bromoacetate (500 mg, 3.0 mmol) was added, and the solution was stirred at rt for another 12 h. After filtration, the solution was concentrated and the residue taken up in $CH_2Cl_2$ and washed with brine. The organic layer was separated and concentrated. The residue was purified by flash chromatography over silica gel (ethyl acetate) to afford the desired product (51 mg, 8.5% yield): LC-MS m/z 202.2 (MH+), retention time 0.73 min (method 1); Rf=0.23 (ethyl acetate).

Intermediate K
[(2S)-1-Amino-2-piperidinyl]methanol

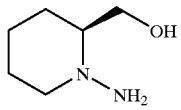

[(2S)-1-Amino-2-piperidinyl]methanol was prepared according to the method described by Rosling et al., (Heterocycles 95–106, 1997). In a similar manner were prepared [(2R)-1-amino-2-piperidinyl]-methanol, [(2S)-1-amino-2-pyrrolidinyl]methanol, and [(2R)-1-amino-2-pyrrolidinyl]methanol.

Intermediate L
3-Methylisonicotinonitrile

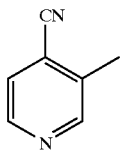

This nitrile was synthesized the procedure described by van den Haak et al., (J. Heterocycl. Chem. 18:1349–1352, 1981.

Summary of Examples

Using appropriate starting materials and the experimental procedures described above for Examples 1–49 and Intermediates A–L, the following compounds in Tables 1–18 were prepared. It will be understood by those skilled in the art that some minor modifications to the referenced procedures may have been made, but such modifications do not significantly affect the results of the preparation.

LC-MS characterization of compounds, as listed in the tables, was carried out by using the instrumentation and methods set forth above.

TABLE 1

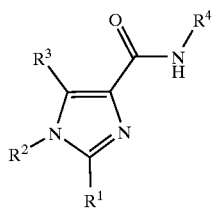

| Entry No. | $R^1$ | $R^2$ | $R^3$ | $R^4$ | IUPAC name | MS m/z [MH+] | TLC Rf (solvent) | HPLC RT (min) | HPLC method | Synthesis Method of Ex. No. |
|---|---|---|---|---|---|---|---|---|---|---|
| 1 | 2,3-Cl$_2$—Ph | 4-Cl—Ph | H | 1-piperidinyl | 1-(4-chlorophenyl)-2-(2,3-dichlorophenyl)-N-(1-piperidinyl)-1H-imidazole-4-carboxamide | 449.1 | | 3.05 | 1 | 8 |
| 2 | 2,4-Cl$_2$—Ph | 4-Cl—Ph | H | 1-piperidinyl | 1-(4-chlorophenyl)-2-(2,4-dichlorophenyl)-N-(1-piperidinyl)-1H-imidazole-4-carboxamide hydrochloride | 449.3 | 0.47 (EtOAc) | 3.14 | 1 | 13,14 |
| 3 | 2,4-Cl$_2$—Ph | 4-F—Ph | H | 1-piperidinyl | 1-(4-fluorophenyl)-2-(2,4-dichlorophenyl)-N-(1-piperidinyl)-1H-imidazole-4-carboxamide hydrochloride | 433.3 | 0.20 (33% EtOAc in Hexane) | 2.89 | 1 | 15 |
| 4 | 2,4-Cl$_2$—Ph | 4-I—Ph | H | 1-piperidinyl | 1-(4-iodophenyl)-2-(2,4-dichlorophenyl)-N-(1-piperidinyl)-1H-imidazole-4-carboxamide | 541.0 | | 3.24 | 1 | 13,14 |
| 5 | 2,4-Cl$_2$—Ph | 4-MeO—Ph | H | 1-piperinyl | 1-(4-methoxyphenyl)-2-(2,4-dichlorophenyl)-N-(1-piperidinyl)-1H-imidazole-4-carboxamide hydrochloride | 445.3 | 0.53 | 2.92 | 1 | 10 |

TABLE 1-continued

| Entry No. | R¹ | R² | R³ | R⁴ | IUPAC name | MS m/z [MH+] | TLC Rf (solvent) | HPLC RT (min) | HPLC method | Synthesis Method of Ex. No. |
|---|---|---|---|---|---|---|---|---|---|---|
| 6 | 2,4-Cl₂—Ph | 4-Me—Ph | H | 1-piperidinyl | 1-(4-methylphenyl)-2-(2,4-dichlorophenyl)-N-(1-piperidinyl)-1H-imidazole-4-carboxamide hydrochloride | 429.3 | 0.25 (75% EtOAc in Hexane) | 2.96 | 1 | 15 |
| 7 | 2,4-F₂—Ph | 4-Cl—Ph | H | 1-piperidinyl | 1-(4-chlorophenyl)-2-(2,4-difluorophenyl)-N-(1-piperidinyl)-1H-imidazole-4-carboxamide | 417.2 | 0.35 (EtOAc) | 2.80 | 1 | 8 |
| 8 | 2,4-Me₂—Ph | 4-Cl—Ph | H | 1-piperidinyl | 1-(4-chlorophenyl)-2-(2,4-dimethylphenyl)-N-(1-piperidinyl)-1H-imidazole-4-carboxamide hydrochloride | 409.3 | 0.62 (EtOAc) | 2.77 | 1 | 10 |
| 9 | 2,4-Me₂—Ph | 4-Cl—Ph | Me | 1-piperidinyl | 1-(4-chlorophenyl)-2-(2,4-dimethylphenyl)-5-methyl-N-(1-piperidinyl)-1H-imidazole-4-carboxamide hydrochloride | 423.2 | | 2.89 | 1 | 8 |
| 10 | 2,5-Cl₂—Ph | 4-Cl—Ph | H | 1-piperidinyl | 1-(4-chlorophenyl)-2-(2,5-dichlorophenyl)-N-(1-piperidinyl)-1H-imidazole-4-carboxamide | 449.1 | 0.34 (75% EtOAc in Hexane) | 3.11 | 1 | 9 |
| 11 | 2-CF₃—Ph | 4-Cl—Ph | H | 1-piperidinyl | 1-(4-chlorophenyl)-N-(1-piperidinyl)-2-[2-(trifluoromethyl)phenyl]-1H-imidazole-4-carboxamide hydrochloride | 449.3 | 0.25 (90% in Hexane) | 2.95 | 1 | 13,14 |
| 12 | 2-Cl-4-F—Ph | 4-F—Ph | H | 1-piperidinyl | 1-(4-fluorophenyl)-2-(2-chloro-4-fluorophenyl)-N-(1-piperidinyl)-1H-imidazole-4-carboxamide hydrochloride | 417.3 | 0.33 (EtOAc) | 2.69 | 1 | 10 |
| 13 | 2-Cl—Ph | 2,4F₂—Ph | H | 1-piperidinyl | 1-(2,4-difluorophenyl)-2-(2-chlorophenyl)-N-(1-piperidinyl)-1H-imidazole-4-carboxamide | 417.2 | 0.18 1:1 EtOAc/Hexane) | 2.64 | 1 | 13,14 |
| 14 | 2-Cl—Ph | 2-Cl—Ph | H | 1-piperidinyl | 1-(2-chloro-4-fluorophenyl)2-(2-chlorophenyl)-N-(1-piperidinyl)-1H-imidazole-4-carboxamide | 432.2 | 0.20 (1:1 EtOAc/Hexane) | 2.74 | 1 | 13,14 |
| 15 | 2-Cl—Ph | 3-Cl—Ph | H | 1-piperidinyl | 1-(3-chlorophenyl)-2-(2-chlorophenyl)-N-(1-piperidinyl)-1H-imidazole-4-carboxamide | 415.8 | 0.15 (50% EtOAc in Hexane) | 2.90 | 1 | 13,14 |
| 16 | 2-Cl—Ph | 3-Cl—Ph | Pr | 1-piperidinyl | 1-(3-chlorophenyl)-2-(2-chlorophenyl)-N-(1-piperidinyl)-5-propyl-1H-imidazole-4-carboxamide | 457.2 | 0.37 (1:1 EtOAc/Hexane) | 2.98 | 1 | 13,14 |
| 17 | 2-Cl—Ph | 4-Br—Ph | Et | 1-piperidinyl | 1-(4-bromophenyl)-2-(2-chlorophenyl)-N-(1-piperidinyl)-5-ethyl-1H-imidazole-4-carboxamide | 487.2 | 0.48 (EtOAc) | 3.05 | 1 | 13,14 |
| 18 | 2-Cl—Ph | 4-Br—Ph | Pr | 1-piperidinyl | 1-(4-bromophenyl)-2-(2-chlorophenyl)-N-(1-piperidinyl)-5-propyl-1H-imidazole-4-carboxamide | 503.1 | 0.28 (1:1 EtOAc/Hexane) | 3.06 | 1 | 13,14 |
| 19 | 2-Cl—Ph | 4-Cl—Ph | Br | 1-piperidinyl | 1-(4-chlorophenyl)-2-(2-chlorophenyl)-N-(1-piperidinyl)-5-bromo-1H-imidazole-4-carboxamide hydrochloride | 493.0 | | 2.64 | 2 | 13,14 |
| 20 | 2-Cl—Ph | 4-Cl—Ph | Bu | 1-piperidinyl | 1-(4-chlorophenyl)-2-(2-chlorophenyl)-N-(1-piperidinyl)-5-butyl-1H-imidazole-4-carboxamide hydrochloride | 471.3 | | 2.98 | 2 | 13,14 |
| 21 | 2-Cl—Ph | 4-Cl—Ph | Cl | 1-piperidinyl | 1-(4-chlorophenyl)-2-(2-chlorophenyl)-N-(1-piperidinyl)-5-chloro-1H-imidazole-4-carboxamide | 451.2 | 0.16 (50% EtOAc in Hexane) | 3.07 | 1 | 10 |
| 22 | 2-Cl—Ph | 4-Cl—Ph | cyclopropyl | 1-piperidinyl | 1-(4-chlorophenyl)-2-(2-chlorophenyl)-N-(1-piperidinyl)-5-cyclopropyl-1H-imidazole-4-carboxamide hydrochloride | 455.2 | | 2.94 | 2 | 13,14 |
| 23 | 2-Cl—Ph | 4-Cl—Ph | Et | 1-piperidinyl | 1-(4-chlorophenyl)-2-(2-chlorophenyl)-N-(1-piperidinyl)-5-ethyl-1H-imidazole-4-carboxamide | 443.6 | 0.21 (60% EtOAc in Hexane) | 2.91 | 1 | 8 |

TABLE 1-continued

| Entry No. | R¹ | R² | R³ | R⁴ | 1-piperidinyl | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 24 | 2-Cl—Ph | 4-Cl—Ph | H | 1-piperidinyl | | 1-(4-chlorophemnyl)-2-(2-chlorophenyl)-N-(1-piperidinyl)-1H-imidazole-4-carboxamide hydrochloride | 415.1 | 0.25 (75% EtOAc in Hexane) | 2.88 | 1 | 13,14 |
| 25 | 2-Cl—Ph | 4-Cl—Ph | H | 2,6-di-methyl-1-piperidinyl | | 2-(2-chlorophenyl)-1-(4-chlorophenyl)-N-(2,6-dimethyl-1-piperidinyl)-1H-imidazole-4-carboxamide | 443.3 | 0.20 (50% EtOAc in Hexane) | 2.94 | 1 | 13,14 |
| 26 | 2-Cl—Ph | 4-Cl—Ph | H | (2S)-2-(hydroxy-methyl) 1-piperidinyl | | 2-(2-chlorophenyl)-1-(4-chlorophenyl)-N-[(2S)-2-(hydroxymethyl)-1-piperidinyl]-1H-imidazole-4-carboxamide | 445.1 | 0.37 (EtOAc) | 2.93 | 1 | 8 |
| 27 | 2-Cl—Ph | 4-Cl—Ph | H | (2R)-2-(hydroxy-methyl)-1-piperidinyl | | 2-(2-chlorophenyl)-1-(4-chlorophenyl)-N-[(2R)-2-(hydroxymethyl)-1-piperidinyl]-1H-imidazole-4-carboxamide | 445.6 | 0.40 (0.2% MeOH in EtOAc) | 2.94 | 1 | 13,14 |
| 28 | 2-Cl—Ph | 4-Cl—Ph | iPr | 1-piperidinyl | | 1-4(4-chlorophenyl)-2-(2-chlorophenyl)-N-(1-piperidinyl)-5-isopropyl-1H-imidazole-4-carboxamide hydrochloride | 457.2 | | 3.23 | 2 | 13,14 |
| 29 | 2-Cl—Ph | 4-Cl—Ph | Me | 1-piperidinyl | | 1-(4-chlorophenyl)-2-(2-chlorophenyl)-N-(1-piperidinyl)-5-methyl-1H-imidazole-4-carboxamide | 429.2 | 0.33 (EtOAc) | 2.97 | 1 | 6 |
| 30 | 2-Cl—Ph | 4-Cl—Ph | Pr | 1-piperidinyl | | 1-(4-chlorophenyl)-2-(2-chlorophenyl)-N-(1-piperidinyl)-5-propyl-1H-imidazole-4-carboxamide | 457.7 | 0.2 (40% EtOAc in Hexane) | 3.04 | 1 | 8 |
| 31 | 2-Cl—Ph | 4-EtNHCONH—Ph | Me | 1-piperidinyl | | 2-(2-chlorophenyl)-1-(4-{[(ethylamino)carbonyl]amino}phenyl) 5-methyl-N-(1-piperidinyl)-1H-imidazole-4-carboxamide trifluroacetate | 481.4 | | 2.35 | 1 | 46 |
| 32 | 2-Cl—Ph | 4-F—Ph | H | 1-piperidinyl | | 1-(4-fluorophenyl)-2-(2-chlorophenyl)-N-(1-piperidinyl)-1H-imidazole-4-carboxamide | 399.3 | 0.15 (50% EtOAc in Hexane) | 2.61 | 1 | 13,14 |
| 33 | 2-Cl—Ph | 4-F—Ph | Pr | 1-piperidinyl | | 1-(4-fluorophenyl)-2-(2-chlorophenyl)-N-(1-piperidinyl)-5-propyl-1H-imidazole-4-carboxamide | 441.2 | 0.23 (1:1 EtOAc/Hexane) | 2.84 | 1 | 13,14 |
| 34 | 2-Cl—Ph | 4-iPr—Ph | Et | 1-piperidinyl | | 1-(4-isopropylphenyl)-2-(2-chlorophenyl)-N-(1-piperidinyl)-5-ethyl-1H-imidazole-4-carboxamide | 451.2 | 0.4 (2.1 EtOAc/Hexane) | 3.06 | 1 | 13,14 |
| 35 | 2-Cl—Ph | 4-MeCONH—Ph | Me | 1-piperidinyl | | 1-[4-(acetylamino)phenyl]-2-(2-chlorophenyl)-5-methyl-N-(1-piperidinyl)-1H-imidazole-4-carboxamide trifluoroacetate | 452.3 | | 2.31 | 1 | 47 |
| 36 | 2-Cl—Ph | 4-MeO—Ph | H | 1-piperidinyl | | 1-(4-methoxyphenyl)-2-(2-chlorophenyl)-N-(1-piperidinyl)-1H-imidazole-4-carboxamide hydrochloride | 411.3 | 0.29 (EtOAc) | 2.62 | 1 | 13,14 |
| 37 | 2-Cl—Ph | 4-MeO—Ph | Pr | 1-piperidinyl | | 1-(4-methoxyphenyl)-2-(2-chlorophenyl)-N-(1-piperidinyl)-5-propyl-1H-imidazole-4-carboxamide | 453.1 | 0.19 (1:1 EtOAc/Hexane) | 2.84 | 1 | 13,14 |
| 38 | 2-Cl—Ph | 4-Me—Ph | H | 1-piperidinyl | | 1-(4-methylphenyl)-2-(2-chlorophenyl)-N-(1-piperidinyl)-1H-imidazole-4-carboxamide | 395.3 | 0.43 (EtOAc) | 2.77 | 1 | 10 |

TABLE 1-continued

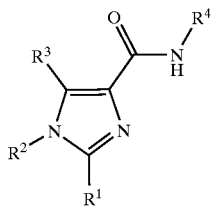

| Entry No. | R¹ | R² | R³ | R⁴ | IUPAC name | MS m/z [MH+] | TLC Rf (solvent) | HPLC RT (min) | HPLC method | Synthesis Method of Ex. No. |
|---|---|---|---|---|---|---|---|---|---|---|
| 39 | 2-Cl—Ph | 4-MeSO₂NH—Ph | Me | 1-piperidinyl | 2-(2-chlorophenyl)-5-methyl-1-{4-[(methylsulfonyl)amino]phenyl}-N-(1-piperidinyl)-1H-imidazole carboxamide trifluoroacetate | 488.4 | | 2.29 | 1 | 48 |
| 40 | 2-Cl—Ph | 4-MeSO₂—Ph | Me | 1-piperidinyl | 2-(2-chlorophenyl)-5-methyl-1-[4-(methylsulfonyl)phenyl]-N-(1-piperidinyl)-1H-imidazole-4-carboxamide | 473.6 | 0.25 (EtOAc) | 2.45 | 1 | 13,14 |
| 41 | 2-Cl—Ph | 4-NO₂—Ph | Me | 1-piperidinyl | 2-(2-chlorophenyl)-5-methyl-1-(4-nitrophenyl)-N-(1-piperidinyl)-1H-imidazole-4-carboxamide | 440.3 | 0.47 (EtOAc) | 2.68 | 1 | 8 |
| 42 | 2-Cl—Ph | Ph | H | 1-piperidinyl | 2-(2-chlorophenyl)-1-phenyl-N-(1-piperidinyl)-1H-imidazole-4-carboxamide | 381.4 | 0.19 (75% EtOAc in Hexane) | 2.64 | 1 | 13,14 |
| 43 | 2-Et—Ph | 4-Cl—Ph | H | 1-piperidinyl | 1-(4-chlorophenyl)-2-(2-ethylphenyl)-N-(1-piperidinyl)-1H-imidazole-4-carboxamide | 409.2 | 0.2 (50% EtOAc in Hexane) | 2.95 | 1 | 8 |
| 44 | 2-MeO—Ph | 4-Cl—Ph | H | 1-piperidinyl | 1-(4-chlorophenyl)-2-(2-methoxyphenyl)-N-(1-piperidinyl)-1H-imidazole-4-carboxamide | 411.3 | 0.38 (75% EtOAc in Hexane) | 2.73 | 1 | 8 |
| 45 | 2-Me—Ph | 2-Me—Ph | H | 1-piperidinyl | 1-(2-methylphenyl)-2-(2-methylphenyl)-N-(1-piperidinyl)-1H-imidazole-4-carboxamide hydrochloride | 375.4 | 0.28 (75% EtOAc in Hexane) | 2.68 | 1 | 13,14 |
| 46 | 2-Me—Ph | 4-Cl—Ph | H | 1-piperidinyl | 1-(4-chlorophenyl)-2-(2-methylphenyl)-N-(1-piperidinyl)-1H-imidazole-4-carboxamide hydrochloride | 395.3 | 0.56 (EtOAc) | 2.83 | 1 | 8 |
| 47 | 2-Me-Ph | 4-Me—Ph | H | 1-piperidinyl | 1-(4-methylphenyl)-2-(2-methylphenyl)-N-(1-piperidinyl)-1H-imidazole-4-carboxamide | 375.4 | 0.17 (50% EtOAc in Hexane) | 2.66 | 1 | 13,14 |
| 48 | 2-NO₂—Ph | 4-Cl—Ph | H | 1-piperidinyl | 1-(4-chlorophenyl)-2-(2-nitrophenyl)-N-(1-piperidine)-1H-imidazole-4-carboxamide | 426.4 | 0.20 (80% EtOAc in Hexane) | 2.60 | 1 | 13,14 |
| 49 | 4-Br—Ph | 2,4-Cl₂—Ph | H | 1-piperidinyl | 2-(4-bromophenyl)-1-(2,4-dichlorophenyl)-N-(1-piperidinyl)-1H-imidazole-4-carboxamide | 495.0 | | 3.23 | 1 | 13,14 |
| 50 | 4-Cl—Ph | 2,4-Cl₂—Ph | H | 1-piperidinyl | 2-(4-chlorophenyl)-1-(2,4-dichlorophenyl)-N-(1-piperidinyl)-1H-imidazole-4-carboxamide hydrochloride | 451.1 | | 3.19 | 1 | 13,14 |
| 51 | 4-I—Ph | 2,4-Cl₂—Ph | H | 1-piperidinyl | 2-(4-iodophenyl)-1-(2,4-dichlorophenyl)-N-(1-piperidinyl)-1H-imidazole-4-carboxamide | 541.0 | | 3.30 | 1 | 13,14 |
| 52 | Ph | 4-Cl—Ph | H | 1-piperidinyl | 1-(4-chlorophenyl)-2-phenyl-N-(1-piperidinyl)-1H-imidazole-4-carboxamide | 381.3 | | 2.65 | 1 | 8 |
| 53 | Ph | Ph | H | 1-piperidinyl | 1,2-diphenyl)-N-(1-piperidinyl)-1H-imidazole-4-carboxamide | 347.2 | | 3.50 | 1 | 13,14 |

TABLE 2

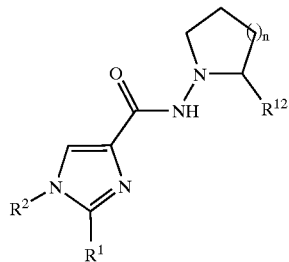

| Entry No. | R¹ | R² | n | R¹² | IUPAC name | MS m/z [MH+] | TLC Rf (solvent) | HPLC RT (min.) | HPLC method | Synthesis Method of Ex. No. |
|---|---|---|---|---|---|---|---|---|---|---|
| 54 | 2-MeO—Ph | 4-Cl—Ph | 1 | H | 1-(4-chlorophenyl)-2-(2-methoxy-phenyl)-N-(1-pyrrolidinyl)-1H-imidazole-4-carboxamide | 397.3 | 0.2 (75% EtOAc in hexane) | 2.46 | 1 | 13,14 |
| 55 | 2-Cl—Ph | 4-Cl—Ph | 1 | H | 2-(2-chlorophenyl)-1-(4-chloro-phenyl)-N-(1-pyrrolidinyl)-1H-imidazole-4-carboxamide trifluoroacetate | 401.2 | 0.4 (5% MeOH in EtOAc) | 2.55 | 1 | 8 |
| 56 | 2-Cl—Ph | 4-Cl—Ph | 1 | (R)—CH₂OMe | 2-(2-chlorophenyl)-1-(4-chlorophenyl)-N-[(2R)-2-(methoxymethyl)-1-pyrrolidinyl]-1H-imidazole-4-carboxamide trifluoroacetate | 445.2 | 0.4 (35% EtOAc in hexane) | 2.84 | 1 | 8 |
| 57 | 2-Cl—Ph | 4-Cl—Ph | 1 | (S)—CH₂OMe | 2-(2-chlorophenyl)-1-(4-chlorophenyl)-N-[(2S)-2-(methoxymethyl)-1-pyrrolidinyl]-1H-imidazole-4-carboxamide trifluoroacetate | 445.2 | 0.4 (5% MeOH in EtOAC) | 2.89 | 1 | 8 |
| 58 | 2-MeO—Ph | 4-Cl—Ph | 1 | (R)—CH₂OMe | 1-(4-chlorophenyl)-N-[(2R)-2-(methoxymethyl)-1-pyrrolidinyl]-2-(2-methoxyphenyl)-1H-imidazole-4-carboxamide | 441.3 | 0.25 (EtOAc) | 2.72 | 1 | 13,14 |
| 59 | 2-MeO—Ph | 4-Cl—Ph | 1 | (S)—CH₂OMe | 1-(4-chlorophenyl)-N-[(2S)-2-(methoxymethyl)-1-pyrrolidinyl]-2-(2-methoxyphenyl)-1H-imidazole-4-carboxamide | 441.3 | 0.25 (EtOAc) | 2.73 | 1 | 13,14 |
| 60 | 2-MeO—Ph | 4-Cl—Ph | 3 | H | N-(1-azepanyl)-1-(4-chlorophenyl)-2-(2-(methoxymethyl)-1H-imidazole-4-carboxamide | 425.3 | 0.5 (50% EtOAc in hexane) | 2.72 | 1 | 13,14 |
| 61 | 2,4-Cl₂—Ph | 4-Cl—Ph | 1 | H | 1-(4-chlorophenyl)-2-(2,4-dichlorophenyl)-N-(1-pyrrolidinyl)-1H-imidazole-4-carboxamide trifluoroacetate | 435.1 | 0.36 (EtOAc) | 2.78 | 1 | 13,14 |
| 62 | 2,4-Cl₂—Ph | 4-Cl—Ph | 1 | (R)—CH₂OMe | 1-(4-chlorophenyl)-2-(2,4-dichlorophenyl)-N-[(2R)-2-(methoxymethyl)-1-pyrrolidinyl]-1H-imidazole-4-carboxamide trifluoroacetate | 479.2 | 0.36 (EtOAc) | 3.13 | 1 | 13,14 |
| 63 | 2-Me—Ph | 4-Cl—Ph | 1 | H | 1-(4-chlorophenyl)-2-(2-methylphenyl)-N-(1-pyrrolidinyl)-1H-imidazole-4-carboxamide | 381.3 | 0.2 (EtOAc) | 2.48 | 1 | 13,14 |
| 64 | 2-Me—Ph | 4-Cl—Ph | 1 | (R)—CH₂OMe | 1-(4-chlorophenyl)-N-[(2R)-2-(methoxymethyl)-1-pyrrolidinyl]-2-(2-methylphenyl)-1H-imidazole-4-carboxamide | 425.3 | 0.33 (EtOAc) | 2.78 | 1 | 13,14 |
| 65 | 2-Me—Ph | 4-Cl—Ph | 1 | (S)—CH₂OMe | 1-(4-chlorophenyl)-N-[(2S)-2-(methoxymethyl)-1-pyrrolidinyl]-2-(2-methylphenyl)-1H-imidazole-4-carboxamide | 425.3 | 0.33 (EtOAc) | 2.79 | 1 | 13,14 |
| 66 | 2-Me—Ph | 4-Cl—Ph | 3 | H | N-(1-azepanyl)-1-(4-chlorophenyl)-2-(2-methylphenyl)-1H-imidazole-4-carboxamide | 409.3 | 0.57 (EtOAc) | 2.61 | 1 | 13,14 |
| 67 | 2,4-Me₂—Ph | 4-Cl—Ph | 1 | H | 1-(4-chlorophenyl)-2-(2,4-dimethylphenyl)-N-(1-pyridinyl)-1H-imidazole-4-carboxamide | 395.3 | 0.25 (EtOAc) | 2.61 | 1 | 13,14 |
| 68 | 2,4-Me₂—Ph | 4-Cl—Ph | 1 | (R)—CH₂OMe | 1-(4-chlorophenyl)-2-(2,4-dimethylphenyl)-N-[(2R)-2-(methoxymethyl)-1-pyrrolidinyl]-1H-imidazole-4-carboxamide | 439.3 | 0.32 (EtOAc) | 2.90 | 1 | 13,14 |
| 69 | 2,4-Me₂—Ph | 4-Cl—Ph | 1 | (S)—CH₂OMe | 1-(4-chlorophenyl)-2-(2,4-dimethylphenyl)-N-[(2S)-2-(methoxymethyl)-1-pyrrolidinyl]-1H-imidazole-4-carboxamide | 439.3 | 0.32 (EtOAc) | 2.91 | 1 | 13,14 |
| 70 | 2,4-Me₂—Ph | 4-Cl—Ph | 3 | H | N-(1-azepanyl)-1-(4-chlorophenyl)-2-(2,4-dimethyl-1H-imidazole-4-carboxamide | 423.3 | 0.6 (EtOAc) | 2.93 | 1 | 13,14 |

TABLE 2-continued

| Entry No. | R¹ | R² | n | R¹² | IUPAC name | MS m/z [MH+] | TLC Rf (solvent) | HPLC RT (min.) | HPLC method | Synthesis Method of Ex. No. |
|---|---|---|---|---|---|---|---|---|---|---|
| 71 | 2,4-Cl₂—Ph | 4-Me—Ph | 3 | H | N-(1-azepanyl)-2-(2,4-dichlorophenyl)-1-(4-methylphenyl)-1H-imidazole-4-carboxamide trifluoroacetate | 443.3 | 0.4 (75% EtOAc in hexane) | 3.03 | 1 | 15 |
| 72 | 2,4-Cl₂—Ph | 4-F—Ph | 3 | H | N-(1-azepanyl)-2-(2,4-dichlorophenyl)-1-(4-fluorophenyl)-1H-imidazole-4-carboxamide trifluoroacetate | 447.3 | 0.4 (75% EtOAc in hexane) | 2.96 | 1 | 15 |
| 73 | 2-Cl—Ph | 4-Cl—Ph | 1 | (S)—CH₂OMe | 2-(2-chlorophenyl)-1-(4-chlorophenyl)-N-[(2S)-2-(hydroxymethyl)-1-pyrrolidinyl]-1H-imidazole-4-carboxamide | 431.1 | 0.24 (EtOAc) | 2.81 | 1 | 8 |
| 74 | 2-Cl—Ph | 4-Cl—Ph | 1 | (R)—CH₂OMe | 2-(2-chlorophenyl)-1-(4-chlorophenyl)-N-[(2R)-2-(hydroxymethyl-1-pyrrolidinyl]-1H-imidazole-4-carboxamide | 431.2 | 0.35 (EtOAc) | 2.71 | 1 | 13,14 |

TABLE 3

| Entry No. | R¹ | R² | Z | IUPAC name | MS m/z [MH+] | TLC Rf (solvent) | HPLC RT (min.) | HPLC method | Synthesis Method of Ex. No. |
|---|---|---|---|---|---|---|---|---|---|
| 75 | 2-Cl—Ph | 4-Cl—Ph | O | 2-(2-chlorophenyl)-1-(4-chlorophenyl)-N-(4-morpholinyl)-1H-imidazole-4-carboxamide | 417.0 | 0.45 (7% MeOH in CH2Cl2) | 3.32 | 1 | 8 |
| 76 | 2-MeO—Ph | 4-Cl—Ph | O | 1-(4-chlorophenyl)-2-(2-methoxyphenyl)-N-(4-morpholinyl)-1H-imidazole-4-carboxamide | 413.2 | 0.22 (75% EtOAc in hexane) | 2.55 | 1 | 13,14 |
| 77 | 2,4-Cl₂—Ph | 4-Cl—Ph | O | 1-(4-chlorophenyl)-2-(2,4-dichlorophenyl)-N-(4-morpholinyl)-1H-imidazole-4-carboxamide | 453.2 | 0.57 (50% EtOAc in hexane) | 3.03 | 1 | 13,14 |
| 78 | 2,4-F—Ph | 4-Cl—Ph | O | 1-(4-chlorophenyl)-2-(2,4-difluorophenyl)-N-(4-morpholinyl)-1H-imidazole-4-carboxamide | 419.2 | 0.28 (5% MeOH in EtOAc) | 2.73 | 1 | 8 |
| 79 | 2-Me—Ph | 4-Cl—Ph | O | 1-(4-chlorophenyl)-2-(2-methylphenyl)-N-(4-morpholinyl)-1H-imidazole-4-carboxamide | 397.3 | 0.18 (EtOAc) | 2.63 | 1 | 13,14 |
| 80 | 2,4-Me—Ph | 4-Cl—Ph | O | 1-(4-chlorophenyl)-2-(2,4-dimethylphenyl)-N-(4-morpholinyl)-1H-imidazole-4-carboxamide | 411.3 | 0.19 (EtOAc) | 2.77 | 1 | 13,14 |
| 81 | 2,4-Me—Ph | 4-Cl—Ph | NMe | 1-(4-chlorophenyl)-2-(2,4-dimethylphenyl)-N-(4-methyl-1-piperazinyl)-1H-imidazole-4-carboxamide bis(trifluoroacetate) | 421.2 | 0.6 (20% 2M NH3/MeOH in EtOAc) | 2.82 | 1 | 13,14 |

TABLE 3-continued

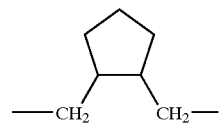

| Entry No. | R¹ | R² | Z | IUPAC name | MS m/z [MH+] | TLC Rf (solvent) | HPLC RT (min.) | HPLC method | Synthesis Method of Ex. No. |
|---|---|---|---|---|---|---|---|---|---|
| 82 | 2,4-Cl₂—Ph | 4-Me—Ph | NMe | 2-(2,4-dichlorophenyl)-1-(4-methylphenyl)-N-(4-methyl-1-piperazinyl)-1H-imidazole-4-carboxamide bis(trifluoroacetate) | 444.3 | | 2.29 | 1 | 15 |
| 83 | 2,4-Cl₂—Ph | 4-F—Ph | NMe | 2-(2,4-dichlorophenyl)-1-(4-fluorophenyl)-N-(4-methyl-1-piperazinyl)-1H-imidazole-4-carboxamide bis(trifluoroacetate) | 448.2 | | 2.21 | 1 | 15 |
| 84 | 2-Et—Ph | 4-Cl—Ph | NMe | 1-(4-chlorophenyl)-2-(2-ethylphenyl)-N-(4-methyl-1-piperazinyl)-1H-imidazole-4-carboxamide | 424.3 | 0.62 (25% 2M NH3/MeOH in EtOAc) | 2.28 | 1 | 13,14 |

TABLE 4

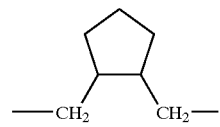

| Entry No. | R¹ | R² | R⁶ | R⁷ | IUPAC name | MS m/z [MH+] | HPLC Retention time (min.) | HPLC method | Synthesis Method of Ex. No. |
|---|---|---|---|---|---|---|---|---|---|
| 85 | 2,4-Cl₂—Ph | 4-Cl—Ph | Me | Me | 2-(4-chlorophenyl)-1-(2,4-dichlorophenyl)-N',N'-dimethyl-1H-imidazole-4-carbohydrazide | 409.0 | 2.9 | 1 | 8 |
| 86 | 2,4-Cl₂—Ph | 4-MeO—Ph | —CH₂— | —CH₂— | 2-(2,4-dichlorophenyl)-N-hexahydrocyclopenta[c]pyrrol-2(1H)-yl-1-(4-methoxyphenyl)-1H-imidazole-4-carboxamide hydrochloride | 471 | 2.98 | 2 | 10,11,12 |
| 87 | 2-Me—Ph | 4-Cl—Ph | —CH₂— | —CH₂— | 1-(4-chlorophenyl)-N-hexahydrocyclopenta[c]pyrrol-2(1H)-yl-2-(2-methylphenyl)-1H-imidazole-4-carboxamide hydrochloride | 421 | 2.82 | 2 | 10,11,12 |

TABLE 4-continued

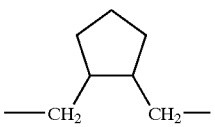

| Entry No. | R¹ | R² | R⁶ | R⁷ | IUPAC name | MS m/z [MH+] | HPLC Retention time (min.) | HPLC method | Synthesis Method of Ex. No. |
|---|---|---|---|---|---|---|---|---|---|
| 88 | 2,4-Cl₂—Ph | 4-F—Ph | | (cyclopentane-CH₂-CH₂-) | 2-(2,4-dichlorophenyl)-1-(4-fluorophenyl)-N-hexahydrocyclopenta[c]pyrrol-2(1H)-yl-1H-imidazole-4-carboxamide hydrochloride | 459 | 3.38 | 2 | 10,11,12 |
| 89 | 2,4-Cl₂—Ph | 4-Cl—Ph | | (cyclopentane-CH₂-CH₂-) | 1-(4-chlorophenyl)-2-(2,4-dichlorophenyl)-N-hexahydrocyclopenta[c]pyrrol-2(1H)-yl-1H-imidazole-4-carboxamide hydrochloride | 475 | 3.16 | 2 | 10,11,12 |
| 90 | 2-Cl—Ph | 4-Cl—Ph | | (cyclopentane-CH₂-CH₂-) | 2-(2-chlorophenyl)-1-(4-chlorophenyl)-N-hexahydrocyclopenta[c]pyrrol-2(1H)-yl-1H-imidazole-4-carboxamide hydrochloride | 441 | 3.23 | 2 | 10,11,12 |

TABLE 5

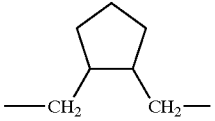

| Entry No. | R¹ | R² | R³ | R⁶ | R⁷ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 91 | 2,4-Cl₂—Ph | 4-Cl—Ph | H | 2-CF₃—Ph | H | 1-(4-chlorophenyl)-2-(2,4-dichlorophenyl)-N'-[2-(trifluoromethyl)phenyl]-1H-imidazole-4-carbohydrazide | 525 | 0.4 (20% EtOAc/Hexane) | 4.25 | 2 | 10,11,12 |
| 92 | 2,4-Cl₂—Ph | 4-Cl—Ph | H | Ph | Me | 2-(2,4-dichlorophenyl)-1-(4-chlorophenyl)-N'-methyl-N'-phenyl-1H-imidazole-4-carbohydrazide | 473 | 0.6 (50% EtOAC in Hexane) | 3.70 | 1 | 8 |
| 93 | 2,4-Cl₂—Ph | 4-Cl—Ph | H | 3-Cl-4-F—Ph | H | N'-(3-chloro-4-fluorophenyl)-2-(2,4-dichlorophenyl)-1-(4-chlorophenyl)-1H-imidazole-4-carbohydrazide hydrochloride | 509 | | 4.13 | 2 | 10,11,12 |
| 94 | 2,4-Cl₂—Ph | 4-F—Ph | H | 2-Cl—Ph | H | N'-(2-chlorophenyl)-2-(2,4-dichlorophenyl)-1-(4-fluorophenyl)-1H-imidazole-4-carbohydrazide hydrochloride | 475 | | 3.40 | 2 | 10,11,12 |

TABLE 5-continued

[Structure: imidazole with R¹ at 2-position, R² on N1, R³ at 5-position, 4-carbohydrazide with N'(R⁶)(R⁷), NH]

| Entry No. | R¹ | R² | R³ | R⁶ | R⁷ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 95 | 2,4-Cl₂—Ph | 4-F—Ph | H | 3-Cl-4-F—Ph | H | N'-(3-chloro-4-fluorophenyl)-2-(2,4-dichlorophenyl)-1-(4-fluorophenyl)-1H-imidazole-4-carbohydrazide hydrochloride | 493 | | 3.39 | 2 | 10,11,12 |
| 96 | 2,4-Cl₂—Ph | 4-F—Ph | H | 2-Cl-4-CF₃—Ph | H | N'-[2-chloro-4-(trifluoromethyl)phenyl]-2-(2,4-dichlorophenyl)-1-(4-fluorophenyl)-1H-imidazole-4-carbohydrazide hydrochloride | 543 | | 3.66 | 2 | 10,11,12 |
| 97 | 2,4-Cl₂—Ph | 4-MeO—Ph | H | 3-Cl-4-F—Ph | H | N'-(3-chloro-4-fluorophenyl)-2-(2,4-dichlorophenyl)-1-(4-methoxyphenyl)-1H-imidazole-4-carbohydrazide hydrochloride | 505 | | 3.36 | 2 | 10,11,12 |
| 98 | 2,4-F₂—Ph | 4-Cl—Ph | H | Ph | Me | 1-(4-chlorophenyl)-2-(2,4-difluorophenyl)-N'-methyl-N'-phenyl-1H-imidazole-4-carbohydrazide | 439 | 0.27 (50% EtOAc in Hexane) | 3.39 | 1 | 8 |
| 99 | 2,4-Me₂—Ph | 4-Cl—Ph | H | Ph | Me | 1-(4-chlorophenyl)-2-(2,4-dimethylphenyl)-N'-methyl-N'-phenyl)-1H-imidazole-4-carbohydrazide | 431 | 0.64 (50% EtOAc in | 3.48 | 1 | 8 |
| 100 | 2,5-Cl₂—Ph | 4-Cl—Ph | H | 2-CF₃—Ph | H | 1-(4-chlorophenyl)-2-(2,5-dichlorophenyl)-N'-[2-(trifluoromethyl)phenyl]-1H imidazole-4-carbohydrazide | 525 | 0.41 (25% EtOAc in Hexane) | 3.76 | 1 | 8 |
| 101 | 2,5-Cl₂—Ph | 4-Cl—Ph | H | 3-CF₃—Ph | H | 1-(4-chlorophenyl)-2-(2,5-dichlorophenyl)-N'-[3-(trifluoromethyl)phenyl]-1H imidazole-4-carbohydrazide | 526 | 0.2 (33% EtOAc in Hexane) | 3.69 | 1 | 8 |
| 102 | 2,5-Cl₂—Ph | 4-Cl—Ph | H | 4-CF₃—Ph | H | 1-(4-chlorophenyl)-2-(2,5-dichlorophenyl)-N'-[4-(trifluoromethyl)phenyl]-1H-imidazole-4-carbohydrazide | 526 | 0.2 (33% EtOAc in Hexane) | 3.70 | 1 | 8 |
| 103 | 2-CF₃—Ph | 4-Cl—Ph | H | 4-CF₃—Ph | H | 1-(4-chlorophenyl)-2-[2-(trifluoromethyl)phenyl]-N'-[4-(trifluoromethyl)phenyl]-1H-imidazole-4-carbohydrazide trifluoroacetate | 525 | | 3.38 | 2 | 10,11,12 |
| 104 | 2-CF₃—Ph | 4-Cl—Ph | H | 2-CF₃—Ph | H | 1-(4-chlorophenyl)-N',2-bis[2-(trifluoromethyl)phenyl]-1H-imidazole-4-carbohydrazide hydrochloride | 525 | | 3.97 | 2 | 10,11,12 |
| 105 | 2-Cl—Ph | 4-Br—Ph | Et | 2-CF₃—Ph | H | 1-(4-bromophenyl)-2-(2-chlorophenyl)-5-ethyl-N'-[2-(trifluoromethyl)phenyl]-1H imidazole-4-carbohydrazide | 563 | 0.24 (20% EtOAc in Hexane) | 3.88 | 1 | 8 |
| 106 | 2-Cl—Ph | 4-Br—Ph | Et | 4-CF₃—Ph | H | 1-(4-bromophenyl)-2-(2-chlorophenyl)-5-ethyl-N'-[4-(trifluoromethyl)phenyl]-1H-imidazole-4-carbohydrazide | 563 | 0.27 (33% EtOAc in Hexane) | | 1 | 8 |
| 107 | 2-Cl—Ph | 4-Br—Ph | Et | 2-Cl-4-CF₃—Ph | H | 1-(4-bromophenyl)-2-(2-chlorophenyl)-N'-[2-chloro-4-(trifluoromethyl)phenyl]-5-ethyl-1H-imidazole-4-carbohydrazide | 597 | 0.18 (20% EtOAc in Hexane) | 3.98 | 1 | 6 |

TABLE 5-continued

| Entry No. | R¹ | R² | R³ | R⁶ | R⁷ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 108 | 2-Cl—Ph | 4-Cl—Ph | Cyclopropyl | 2-CF₃—Ph | H | 2-(2-chlorophenyl)-1-(4-chlorophenyl)-5-cyclopropyl-N'-[2-(trifluoromethyl)phenyl]-1H-imidazole-4-carbohydrazide hydrochloride | 531 | | 3.61 | 2 | 13,14 |
| 109 | 2-Cl—Ph | 4-Cl—Ph | Cyclopropyl | 4-CF₃—Ph | H | 2-(2-chlorophenyl)-1-(4-chlorophenyl)-5-cyclopropyl-N'-[4-(trifluoromethyl)phenyl]-1H-imidazole-4-carbohydrazide hydrochloride | 531 | | 3.62 | 2 | 13,14 |
| 110 | 2-Cl—Ph | 4-Cl—Ph | Et | 2,4-Cl₂—Ph | H | 2-(2-chlorophenyl)-1-(4-chlorophenyl)-N'-(2,4-dichlorophenyl)-5-ethyl-1H-imidazole-4-carbohydrazide | 519 | 0.6 (3% EtOAc in Hexane) | 4.02 | 1 | 6 |
| 111 | 2-Cl—Ph | 4-Cl—Ph | Et | 2,4(CF₃)₂—Ph | H | N'-[2,4-bis(trifluoromethyl)phenyl]-2-(2-chlorophenyl)-1-(4-chlorophenyl)-5-ethyl-1H-imidazole-4-carbohydrazide | 587 | 0.47 (30% EtOAc in Hexane) | 3.75 | 1 | 8 |
| 112 | 2-Cl—Ph | 4-Cl—Ph | H | 2-CF₃—Ph | H | 2-(2-chlorophenyl)-1-(4-chlorophenyl)-N'-[2-(trifluoromethyl)phenyl]-1H-imidazole-4-carbohydrazide hydrochloride | 491 | | 4.02 | 2 | 10,11,12 |
| 113 | 2-Cl—Ph | 4-Cl—Ph | H | 3-CF₃—Ph | H | 2-(2-chlorophenyl)-1-(4-chlorophenyl)-N'-[3-(trifluoromethyl)phenyl]-1H-imidazole-4-carbohydrazide hydrochloride | 491 | | 3.99 | 2 | 10,11,12 |
| 114 | 2-Cl—Ph | 4-Cl—Ph | H | 4-CF₃—Ph | H | 2-(2-chlorophenyl)-1-(4-chlorophenyl)-N'-[4-(trifluoromethyl)phenyl]-1H-imidazole-4-carbohydrazide hydrochloride | 491 | | 3.99 | 2 | 10,11,12 |
| 115 | 2-Cl—Ph | 4-Cl—Ph | H | 2-CF₃—4-Cl—Ph | H | 2-(2-chlorophenyl)-1-(4-chlorophenyl)-N'-[4-chloro-2-(trifluoromethyl)phenyl]-1H-imidazole-4-carbohydrazide hydrochloride | 525 | | 3.55 | 2 | 10,11,12 |
| 116 | 2-Cl—Ph | 4-Cl—Ph | H | Ph | Me | 2-(2-chlorophenyl)-1-(4-chlorophenyl)-N'-methyl-N'-phenyl-1H-imidazole-4-carbohydrazide | 437 | 0.5 (60% EtOAc in Hexane) | 3.85 | 1 | 8 |
| 117 | 2-Cl—Ph | 4-Cl—Ph | H | Ph | H | 2-(2-chlorophenyl)-1-(4-chlorophenyl)-N'-phenyl-1H-imidazole-4-carbohydrazide hydrochloride | 423 | | 3.07 | 2 | 10,11,12 |
| 118 | 2-Cl—Ph | 4-Cl—Ph | H | 2,4-Cl₂—Ph | H | N'-(2,4-dichlorophenyl)-2-(2-chlorophenyl)-1-(4-chlorophenyl)-1H-imidazole-4-carbohydrazide hydrochloride | 492 | | 3.55 | 2 | 10,11,12 |
| 119 | 2-Cl—Ph | 4-Cl—Ph | H | 2,4-F₂—Ph | H | N'-(2,4-difluorophenyl)-2-(2-chlorophenyl)-1-(4-chlorophenyl)-1H-imidazole-4-carbohydrazide hydrochloride | 460 | | 3.07 | 2 | 10,11,12 |
| 120 | 2-Cl—Ph | 4-Cl—Ph | H | 2-Cl-4-CN—Ph | H | N'-(2-chloro-4-cyanophenyl)-2-(2-chlorophenyl)-1-(4-chlorophenyl)-1H-imidazole-4-carbohydrazide hydrochloride | 482 12 | | 3.03 | 2 | 10,11, |

TABLE 5-continued

| Entry No. | R¹ | R² | R³ | R⁶ | R⁷ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 121 | 2-Cl—Ph | 4-Cl—Ph | H | 2-Cl—Ph | H | N'-(2-chlorophenyl)-2-(2-chlorophenyl)-1-(4-chlorophenyl)-1H-imidazole-4-carbohydrazide hydrochloride | 457 | | 3.18 | 2 | 10,11,12 |
| 122 | 2-Cl—Ph | 4-Cl—Ph | H | 3-Cl-4-F—Ph | H | N'-(3-chloro-4-fluorophenyl)-2-(2-chlorophenyl)-1-(4-chlorophenyl)-1H-imidazole-4-carbohydrazide hydrochloride | 475 | | 3.28 | 2 | 10,11,12 |
| 123 | 2-Cl—Ph | 4-Cl—Ph | H | 2-Me-4-Cl—Ph | H | N'-(4-chloro-2-methylphenyl)-2-(2-chlorophenyl)-1-(4-chlorophenyl)-1H-imidazole-4-carbohydrazide hydrochloride | 471 | | 3.36 | 2 | 10,11,12 |
| 124 | 2-Cl—Ph | 4-Cl—Ph | H | 2,4-(CF₃)₂—Ph | H | N'-[2,4-bis(trifluoromethyl)phenyl]-2-(2-chlorophenyl)-1-(4-chlorophenyl)-1H-imidazole-4-carbohydrazide hydrochloride | 559 | | 3.62 | 2 | 10,11,12 |
| 125 | 2-Cl—Ph | 4-Cl—Ph | H | 2-Cl-4-CF₃—Ph | H | N'-[2-chloro-4-(trifluoromethyl)phenyl]-2-(2-chlorophenyl)-1-(4-chlorophenyl)-1H-imidazole-4-carbohydrazide | 525 | | 3.55 | 2 | 10,11,12 |
| 126 | 2-Cl—Ph | 4-Cl—Ph | Me | 2,4-Cl₂—Ph | H | 2-(2-chlorophenyl)-1-(4-chlorophenyl)-N'-(2,4-dichlorophenyl)-5-methyl-1H-imidazole-4-carbohydrazide | 505 | 0.71 (50% EtOAc in Hexane) | 3.88 | 1 | 6 |
| 127 | 2-Cl—Ph | 4-Cl—Ph | Pr | 2,4-Cl₂—Ph | H | 2-(2-chlorophenyl)-1-(4-chlorophenyl)-N'-(2,4-dichlorophenyl)-5-propyl-1H-imidazole-4-carbohydrazide | 533 | | 3.87 | 2 | 10,11,12 |
| 128 | 2-Cl—Ph | 4-Cl—Ph | Pr | 2,4-Cl₂—Ph | H | 2-(2-chlorophenyl)-1-(4-chlorophenyl)-N'-(2,4-dichlorophenyl)-5-propyl-1H-imidazole-4-carbohydrazide hydrochloride | 533 | | 3.87 | 2 | 10,11,12 |
| 129 | 2-Cl—Ph | 4-Cl—Ph | Pr | 2,4-(CF₃)₂—Ph | H | N'-[2,4-bis(trifluoromethyl)phenyl]-2-(2-chlorophenyl)-1-(4-chlorophenyl)-5-propyl-1H-imidazole-4-carbohydrazide hydrochloride | 601 | 4.00 | | | 10,11,12 |
| 130 | 2-Cl—Ph | 4-F—Ph | H | 2-CF₃—Ph | H | 2-(2-chlorophenyl)-1-(4-fluorophenyl)-N'-[2-(trifluoromethyl)phenyl]-1H-imidazole-4-carbohydrazide hydrochloride | 475 | | 3.68 | 2 | 10,11,12 |
| 131 | 2-Cl—Ph | 4-F—Ph | H | 4-CF₃—Ph | H | 2-(2-chlorophenyl)-1-(4-fluorophenyl)-N'-[4-(trifluoromethyl)phenyl]-1H-imidazole-4-carbohydrazide hydrochloride | 475 | | 3.27 | 2 | 10,11,12 |
| 132 | 2-Cl—Ph | 4-Me—Ph | H | 2-CF₃—Ph | H | 2-(2-chlorophenyl)-1-(4-methylphenyl)-N'-[2-(trifluoromethyl)phenyl]-1H-imidazole-4-carbohydrazide trifluoroacetate | 471 | | 4.02 | 2 | 10,11,12 |
| 133 | 2-Cl—Ph | 4-Me—Ph | H | 3-CF₃—Ph | H | 2-(2-chlorophenyl)-1-(4-methylphenyl)-N'-[3-(trifluoromethyl)phenyl]-1H-imidazole-4-carbohydrazide trifluoroacetate | 471 | | 3.88 | 2 | 10,11,12 |

TABLE 5-continued

| Entry No. | R¹ | R² | R³ | R⁶ | R⁷ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 134 | 2-Cl—Ph | 4-Me—Ph | H | 4-CF₃—Ph | H | 2-(2-chlorophenyl)-1-(4-methylphenyl)-N'-[4-(trifluoromethyl)phenyl]-1H-imidazole-4-carbohydrazide hydrochloride | 471 | | 3.28 | 2 | 10,11,12 |
| 135 | 2-Cl—Ph | 4-NO₂—Ph | Me | 2-CF₃—Ph | H | 2-(2-chlorophenyl)-5-methyl-1-(4-nitrophenyl)-N'[2-(trifluoromethyl)phenyl]-1H-imidazole-4-carbohydrazide | 516 | 0.4 (33% EtOAc in Hexane) | 3.56 | 1 | 8 |
| 136 | 2-Et—Ph | 4-Cl—Ph | H | Ph | Me | 1-(4-chlorophenyl)-2-(2-ethylphenyl)-N'-methyl-N'-phenyl-1H-imidazole-4-carbohydrazide | 431 | 0.68 (50% EtOAC in Hexane) | 3.52 | 1 | 8 |
| 137 | 2-MeO—Ph | 4-Cl—Ph | H | Ph | Me | 2-(2-methoxyphenyl)-1-(4-chlorophenyl)-N'-methyl-N'-phenyl-1H-imidazole-4-carbohydrazide | 433 | 0.45 (50% EtOAc in Hexane) | 3.26 | 1 | 8 |
| 138 | 2-Me—Ph | 4-Cl—Ph | H | 2-CF₃—Ph | H | 1-(4-chlorophenyl)-2-(2-methylphenyl)-N'-[2-(trifluoromethyl)phenyl]-1H-imidazole-4-carbohydrazide | 471 | 0.4 (20% EtOAc/Hexane) | 3.89 | 2 | 10,11,12 |
| 139 | 2-Me-Ph | 4-Cl—Ph | H | Ph | Me | 1-(4-chlorophenyl)-2-(2-methylphenyl)-N'-methyl-N'-phenyl-1H-imidazole-4-carbohydrazide | 417 | 0.54 (50% EtOAc in Hexane) | 3.34 | 1 | 8 |
| 140 | 2-Me—Ph | 4-Cl—Ph | H | 3-Cl-4-F—Ph | H | N'-(3-chloro-4-fluorophenyl)-2-(2-methylphenyl)-1-(4-chlorophenyl)-1H-imidazole-4-carbohydrazide hydrochloride | 455 | | 3.78 | 2 | 10,11,12 |

TABLE 6

| Entry No. | R¹ | R² | R³ | R⁴ | IUPAC name | MS m/z [MH⁺] | TLC Rf (solvent) | HPLC RT (min) | HPLC method | Synthesis Method of Ex. No. |
|---|---|---|---|---|---|---|---|---|---|---|
| 141 | 4-Br—Ph | 2,4-Cl₂—Ph | H | H | 2-(4-bromophenyl)-N-cyclohexyl-1-(2,4-dichlorophenyl)-1H-imidazole-4-carboxamide | 494.0 | | 3.96 | 1 | 8 |
| 142 | 4-Cl—Ph | 2,4-Cl₂—Ph | H | H | 2-(4-chlorophenyl)-N-cyclohexyl-1-(2,4-dichlorophenyl)-1H-imidazole-4-carboxamide | | | | | 13, 14 |

TABLE 6-continued

| Entry No. | R¹ | R² | R³ | R⁴ | IUPAC name | MS m/z [MH⁺] | TLC Rf (solvent) | HPLC RT (min) | HPLC method | Synthesis Method of Ex. No. |
|---|---|---|---|---|---|---|---|---|---|---|
| 143 | Ph | Ph | H | H | N-cyclohexyl-1,2-diphenyl-1H-imidazole-4-carboxamide | 346.2 | | 3.22 | 1 | 8 |
| 144 | 4-I—Ph | 2,4-Cl₂—Ph | H | H | N-cyclohexyl-1-(2,4-dichlorophenyl)-2-(4-iodophenyl)-1H-imidazole-4-carboxamide | 540.0 | | 4.03 | 1 | 8 |
| 145 | 2,4-Cl₂—Ph | 4-Cl—Ph | H | H | 1-(4-chlorophenyl)-N-cyclohexyl-2-(2,4-dichlorophenyl)-1H-imidazole-4-carboxamide | 448.2 | 0.57 (50% EtOAc in hexane) | 3.84 | 1 | 13, 14 |
| 146 | 2-Cl—Ph | 4-Cl—Ph | H | H | 2-(2-chlorophenyl)-1-(4-chlorophenyl)-N-cyclohexyl-1H-imidazole-4-carboxamide | 414.2 | 0.21 (35% EtOAc in hexane) | 3.48 | 1 | 8 |
| 147 | 2-MeO—Ph | 4-Cl—Ph | H | H | 1-(4-chlorophenyl)-N-cyclohexyl-2-(2-methoxyphenyl)-1H-imidazole-4-carboxamide | 410.2 | 0.5 (50% EtOAc in hexane) | 3.25 | 1 | 13, 14 |
| 148 | 2-Me—Ph | 4-Cl—Ph | H | H | 1-(4-chlorophenyl)-N-cyclohexyl-2-(2-methylphenyl)-1H-imidazole-4-carboxamide | 394.2 | 0.64 (50% EtOAc in hexane) | 3.44 | 1 | 13, 14 |
| 149 | 2,4-Me₂—Ph | 4-Cl—Ph | H | H | 1-(4-chlorophenyl)-N-cyclohexyl-2-(2,4-dimethylphenyl)-1H-imidazole-4-carboxamide | 408.3 | 0.68 (50% EtOAc in hexane) | 3.56 | 1 | 13, 14 |
| 150 | 2,4-Cl₂—Ph | 4-MeO—Ph | H | H | N-cyclohexyl-2-(2,4-dichlorophenyl)-1-(4-methoxyphenyl)-1H-imidazole-4-carboxamide | 444.2 | | 3.55 | 1 | 8 |
| 151 | 2-F—Ph | 2-NO₂—Ph | Me | H | N-cyclohexyl-2-(2-fluorophenyl)-5-methyl-1-(2-nitrophenyl)-1H-imidazole-4-carboxamide | 423.2 | 0.11 (33% EtOAc in hexane) | 3.22 | 1 | 8 |
| 152 | 2,4-Cl₂—Ph | 4-Me—Ph | H | H | N-cyclohexyl-2-(2,4-dichlorophenyl)-1-(4-methylphenyl)-1H-imidazole-4-carboxamide | 426.2 | 0.6 (30% EtOAc in hexane) | 3.76 | 1 | 15 |
| 153 | 2,4-Cl₂—Ph | 4-F—Ph | H | H | N-cyclohexyl-2-(2,4-dichlorophenyl)-1-(4-fluorophenyl)-1H-imidazole-4-carboxamide | 432.2 | 0.17 (30% EtOAc in hexane) | 3.62 | 1 | 15 |
| 154 | 2,4-F₂—Ph | 4-Cl—Ph | H | H | 1-(4-chlorophenyl)-N-cyclohexyl-2-(2,4-difluorophenyl)-1H-imidazole-4-carboxamide | 416.3 | 0.22 (30% EtOAc in hexane) | 3.47 | 1 | 15 |
| 155 | 2-Cl—Ph | 4-NO₂—Ph | Me | H | 2-(2-chlorophenyl)-N-cyclohexyl-5-methyl-1-(4-nitrophenyl)-1H-imidazole-4-carboxamide | 439.2 | | 3.41 | 1 | 8 |
| 156 | 2-Et—Ph | 4-Cl—Ph | H | H | 1-(4-chlorophenyl)-N-cyclohexyl-2-(2-ethylphenyl)-1H-imidazole-4-carboxamide | 408.3 | 0.72 (50% EtOAc in hexane) | 3.62 | 1 | 13, 14 |
| 157 | 2-Cl—Ph | 4-Cl—Ph | H | Me | 2-(2-chlorophenyl)-1-(4-chlorophenyl)-N-cyclohexyl-N-methyl-1H-imidazole-4-carboxamide | 428.2 | 0.19 (50% EtOAc in hexane) | 3.47 | 1 | 8 |
| 158 | 2-Cl—Ph | 4-F—Ph | H | H | 2-(2-chlorophenyl)-N-cyclohexyl-1-(4-fluorophenyl)-1H-imidazole-4-carboxamide | 398.3 | 0.52 (50% EtOAc in hexane) | 3.22 | 1 | 10, 11, 12 |
| 159 | 2-Cl—Ph | 4-MeO—Ph | H | H | 2-(2-chlorophenyl)-N-cyclohexyl-1-1-(4-methoxyphenyl)-1H-imidazole-4-carboxamide | 410.3 | 0.47 (50% EtOAc in hexane) | 3.16 | 1 | 10, 11, 12 |
| 160 | 2-Cl—Ph | 4-Me—Ph | H | H | 2-(2-chlorophenyl)-N-cyclohexyl-1-(4-methylphenyl)-1H-imidazole-4-carboxamide | 394.3 | 0.6 (50% EtOAc in hexane) | 3.31 | 1 | 10, 11, 12 |
| 161 | Ph | 4-Cl—Ph | H | H | 1-(4-chlorophenyl)-N-cyclohexyl-2-phenyl-1H-imidazole-4-carboxamide | 380.3 | | 3.35 | 1 | 8 |
| 162 | 2,5-Cl₂—Ph | 4-Cl—Ph | H | H | 1-(4-chlorophenyl)-N-cyclohexyl-2-(2,5-dichlorophenyl)-1H-imidazole-4-carboxamide | 448.6 | 0.15 (25% EtOAc in hexane) | 3.83 | 1 | 8 |

TABLE 7

| Entry No. | R¹ | R² | R³ | R⁴ | R⁵ | IUPAC name | MS m/z [MH+] | TLC RT (solvent) | HPLC RT (min) | HPLC method | Synthesis Method of Ex. No. |
|---|---|---|---|---|---|---|---|---|---|---|---|
| 163 | 4-Cl—Ph | 2,4-Cl₂—Ph | H | —(CH₂)₅— | | 1-{[2-(4-chlorophenyl)-1-(2,4-dichlorophenyl)-1H-imidazol-4-yl]carbonyl}-piperidine | 436.1 | | 3.59 | 1 | 13, 14 |
| 164 | 4-Cl—Ph | 2,4-Cl₂—Ph | H | Me | Me | 2-(4-dichlorophenyl)-1-(2,4-dichlorophenyl)-N,N-dimethyl-1H-imidazole-4-carboxamide | | | | | 13, 14 |
| 165 | 2,4-Cl₂—Ph | 4-Me—Ph | H | —(CH₂)₅— | | 1-{[2-(2,4-dichlorophenyl)-1-(4-methylphenyl)-1H-imidazol-4-yl]carbonyl}-piperidine | 414.3 | 0.2 (50% EtOAc in hexane) | 3.34 | 1 | 9 |
| 166 | 2,4-Cl₂—Ph | 4-MeO—Ph | H | —CH₂CH=CH(Ph)CH₂CH₂— | | 1-{[2-(2,4-dichlorophenyl)-1-(4-methoxyphenyl)-1H-imidazol-4-yl]carbonyl}-4-phenyl-1,2,3,6-tetrahydropyridine | 522 | | 3.53 | 2 | 10, 11, 12 |
| 167 | 2,4-Cl₂—Ph | 4-Cl—Ph | H | —CH₂CH=CH(Ph)CH₂CH₂— | | 1-{[1-(4-chlorophenyl)-2-(2,4-dichlorophenyl)-1H-imidazol-4-yl]carbonyl}-4-phenyl-1,2,3,6-tetrahydropyridine | 526 | | 3.33 | 2 | 10, 11, 12 |
| 168 | 2-Me—Ph | 4-Cl—Ph | H | —CH₂CH=CH(Ph)CH₂CH₂— | | 1-{[1-(4-chlorophenyl)-2-(2-methylphenyl)-1H-imidazol-4-yl]carbonyl}-4-phenyl-1,2,3,6-tetrahydropyridine | 472 | | 2.9 | 2 | 10, 11, 12 |
| 169 | 2,4-Cl₂—Ph | 4-F—Ph | H | —CH₂CH=CH(Ph)CH₂CH₂— | | 1-{[2-(2,4-dichlorophenyl)-1-(4-fluorophenyl)-1H-imidazol-4-yl]carbonyl}-4-phenyl-1,2,3,6-tetrahydropyridine | 510 | | 3.05 | 2 | 10, 11, 12 |

TABLE 7-continued

| Entry No. | R¹ | R² | R³ | R⁴ | R⁵ | IUPAC name | MS m/z [MH+] | TLC RT (solvent) | HPLC RT (min) | HPLC method | Synthesis Method of Ex. No. |
|---|---|---|---|---|---|---|---|---|---|---|---|
| 170 | 2-Cl—Ph | 4-Cl—Ph | H | | —CH₂CH=CH(Ph)CH₂CH₂— | 1-{[2-(2-chlorophenyl)-1-(4-chlorophenyl)-1H-imidazol-4-yl]carbonyl}-4-phenyl-1,2,3,6-tetrahydropyridine | 492 | | 3.47 | 2 | 10, 11, 12 |
| 171 | 2-Cl—Ph | 4-Cl—Ph | H | | —(CH₂)₃CH(CH₂OH)CH₂— | (1-{[2-(2-chlorophenyl)-1-(4-chlorophenyl)-1H-imidazol-4-yl]carbonyl}-3-piperidinyl)-methanol | 430 | | 2.52 | 2 | 10, 11, 12 |
| 172 | 2-Cl—Ph | 4-Cl—Ph | H | Me | (1-methyl-3-pyrrolidinyl) | 2-(2-chlorophenyl)-1-(4-chlorophenyl)-N-methyl-N-(1-methyl-3-pyrrolidinyl)-1H-imidazole-4-carboxamide hydrochloride | 429 | | 2.15 | 2 | 10, 11, 12 |
| 173 | 2-Cl—Ph | 4-Cl—Ph | H | | —(CH₂)₂CH[N(Et)₂]CH₂— | N-(1-{[2-(2-chlorophenyl)-1-(4-chlorophenyl)-1H-imidazol-4-yl]carbonyl}-3-pyrrolidinyl)-N,N-diethylamine hydrochloride | 457 | | 2.08 | 2 | 10, 11, 12 |
| 174 | 2,4-Cl₂—Ph | 4-Cl—Ph | H | Me | (1R,2R)-2-(methylamino)cyclohexyl | 1-(4-chlorophenyl)-2-(2,4-dichlorophenyl)-N-methyl-N-[(1R,2R)-2-(methylamino)cyclohexyl]-1H-imidazole-4-carboxamide hydrochloride | 491.2 | | 2.41 | 2 | 10, 11, 12 |
| 175 | 2,4-Cl₂—Ph | 4-Cl—Ph | H | Me | (1S,2S)-2-(methylamino)cyclohexyl | 1-(4-chlorophenyl)-2-(2,4-dichlorophenyl)-N-methyl-N-[(1S,2S)-2-(methylamino)cyclohexyl]-1H-imidazole-4-carboxamide hydrochloride | 491.2 | | 2.34 | 2 | 10, 11, 12 |

TABLE 7-continued

| Entry No. | R¹ | R² | R³ | R⁴ | R⁵ | IUPAC name | MS m/z [MH+] | TLC RT (solvent) | HPLC RT (min) | HPLC method | Synthesis Method of Ex. No. |
|---|---|---|---|---|---|---|---|---|---|---|---|
| 176 | 2-Cl—Ph | 4-Cl—Ph | H | | —(CH$_2$)$_2$S(CH$_2$)$_2$— | 4-{[2-(2-chlorophenyl)-1-(4-chlorophenyl)-1H-imidazolyl-4-yl]-carbonyl}-thiomorpholine | 418.6 | 0.3 (50% EtOAc in hexane) | 3.15 | 1 | 13, 14 |
| 177 | 2-Cl—Ph | 4-Cl—Ph | H | | —(CH$_2$)$_2$C(=O)(CH$_2$)$_2$— | 1-{[2-(2-chlorophenyl)-1-(4-chlorophenyl)-1H-imidazol-4-yl]carbonyl}-4-piperidine | 414.1 | 0.29 (50% EtOAc in hexane) | 2.75 | 1 | 13, 14 |
| 178 | 2-Cl—Ph | 4-Cl—Ph | H | | —(CH$_2$)$_2$S(CH$_2$)$_2$— (S=O) | 4-{[2-(2-chlorophenyl)-1-(4-chlorophenyl)-1H-imidazol-4-yl]carbonyl}-thiomorpholine 1-oxide | 434.5 | 0.47 (1:5 EtOAc/Hexane) | 2.55 | 1 | 13, 14 |
| 179 | 2-Cl—Ph | 4-Cl—Ph | Et | | —(CH$_2$)$_2$C(=O)(CH$_2$)$_2$— | 1-{[2-(2-chlorophenyl)-1-(4-chlorophenyl)-5-ethyl-1H-imidazol-4-yl]-carbonyl}-4-piperidinone | 442.1 | 0.06 (1:1 EtOAc/Hexanes) | 2.99 | 1 | 13, 14 |
| 180 | 2-Cl—Ph | 4-Cl—Ph | n-Pr | | —(CH$_2$)$_2$C(=O)(CH$_2$)$_2$— | 1-{[2-(2-chlorophenyl)-1-(4-chlorophenyl)-5-propyl-1H-imidazol-4-yl]carbonyl}-4-piperidinone | 456.1 | 0.06 (1:1 EtOAc/Hexanes) | 3.13 | 1 | 13, 14 |
| 181 | 2-Cl—Ph | 4-Cl—Ph | H | Me | OMe | 2-(2-chlorophenyl)-1-(4-chlorophenyl)-N-methoxy-N-methyl-1H-imidazole-4-carboxamide | 376.1 | 0.22 (EtOAc) | 2.77 | 1 | 13, 14 |
| 182 | 2-Cl—Ph | 2,4-F$_2$—Ph | H | | —(CH$_2$)$_5$— | 1-{[2-(2-chlorophenyl)-1-(2,4-difluorophenyl)-1H-imidazol-4-yl]carbonyl}-piperidine | 402.2 | 0.36 (2:1 EtOAc/Hexanes) | 2.97 | 1 | 13, 14 |
| 183 | 2-Cl—Ph | 4-iPr—Ph | Et | | —(CH$_2$)$_5$— | 1-{[2-(2-chlorophenyl)-5-(ethyl-1-(4-isopropyl-phenyl)-1H-imidazol-4-yl]-carbonyl}piperidine | 436.1 | 0.06 (1:1 EtOAc/Hexanes) | 3.36 | 1 | 13, 14 |

TABLE 8

| Entry No. | R¹ | R² | R⁴ | IUPAC name | MS m/z [MH+] | TLC Rf (solvent) | HPLC RT (min) | HPLC method | Synthesis Method of Ex. No. |
|---|---|---|---|---|---|---|---|---|---|
| 184 | 2-MeO—Ph | 4-Cl—Ph | Ph | 1-(4-chlorophenyl)-2-(2-methoxyphenyl)-N-phenyl-1H-imidazole-4-carboxamide | 404.1 | 0.83 (50% EtOAc in hexane) | 3.42 | 1 | 13, 14 |
| 185 | 2,4-Cl₂—Ph | 4-Cl—Ph | Ph | 1-(4-chlorophenyl)-2-(2,4-dichlorophenyl)-N-phenyl-1H-imidazole-4-carboxamide | 444.1 | 0.89 (50% EtOAc in hexane) | 3.87 | 1 | 13, 14 |
| 186 | 2-Cl—Ph | 4-Cl—Ph | 4H-1,2,4-triazol-4-yl | 2-(2-chlorophenyl)-1-(4-chlorophenyl)-N-(4H-1,2,4-triazol-4-yl)-1H-imidazole-4-carboxamide | 399.1 | <0.1 (15% MeOH in EtOAc) | 2.71 | 1 | 8 |
| 187 | 2-Cl—Ph | 4-Cl—Ph | Ph | 2-(2-chlorophenyl)-1-(4-chlorophenyl)-N-phenyl-1H-imidazole-4-carboxamide | 408.1 | 0.4 (35% EtOAc in hexane) | 3.54 | 1 | 8 |
| 188 | 2,4-F₂—Ph | 4-Cl—Ph | Ph | 1-(4-chlorophenyl)-2-(2,4-difluorophenyl)-N-phenyl-1H-imidazole-4-carboxamide | 410.1 | 0.5 (35% EtOAc in hexane) | 3.52 | 1 | 8 |
| 189 | 2-Me—Ph | 4-Cl—Ph | Ph | 1-(4-chlorophenyl)-2-(2-methylphenyl)-N-phenyl-1H-imidazole-4-carboxamide | 388.1 | 0.86 (50% EtOAc in hexane) | 3.52 | 1 | 13, 14 |
| 190 | 2,4-Me₂—Ph | 4-Cl—Ph | Ph | 1-(4-chlorophenyl)-2-(2,4-dimethylphenyl)-N-phenyl-1H-imidazole-4-carboxamide | 402.2 | 0.92 (50% EtOAc in hexane) | 3.67 | 1 | 13, 14 |
| 191 | 2,4-Me₂—Ph | 4-Cl—Ph | 4H-1,2,4-triazol-4-yl | 1-(4-chlorophenyl)-2-(2,4-dimethylphenyl)-N-(4H-1,2,4-triazol-4-yl)-1H-imidazole-4-carboxamide | 393.1 | 0.19 (20% 2M NH3/MeOH in EtOAc) | 2.87 | 1 | 13, 14 |
| 192 | 2,4-Me₂—Ph | 4-Cl—Ph | 3,5-dimethyl-4H-1,2,4- | 1-(4-chlorophenyl)-2-(2,4-dimethylphenyl)-N-(3,5-dimethyl-4H-1,2,4-triazol-4-yl)-1H-imidazole-4-triazol-4-yl carboxamide | 424.2 | 0.26 (20% 2M NH3/MeOH in EtOAc) | 2.37 | 1 | 13, 14 |
| 193 | 2,4-Cl₂—Ph | 4-F—Ph | Ph | 2-(2,4-dichlorophenyl)-1-(4-fluorophenyl)-N-phenyl-1H-imidazole-4-carboxamide | 426.1 | 0.46 (30% EtOAc in hexane) | 3.61 | 1 | 15 |
| 194 | 2-Cl—Ph | 4-Cl—Ph | 3-pyridinyl | 2-(2-chlorophenyl)-1-(4-chlorophenyl)-N-(3-pyridinyl)-1H-imidazole-4-carboxamide | 409.3 | 0.25 (5% MeOH in EtOAc) | 2.44 | 1 | 15 |
| 195 | 2-Cl—Ph | 4-Cl—Ph | 2-pyridinyl | 2-(2-chlorophenyl)-1-(4-chlorophenyl)-N-(2-pyridinyl)-1H-imidazole-4-carboxamide | 409.1 | 0.25 (5% MeOH in CH2Cl2) | 2.99 | 1 | 15 |
| 196 | 2-Cl—Ph | 4-Cl—Ph | 4-Cl—Ph | 2-(2-chlorophenyl)-N,1-bis(4-chlorophenyl)-1H-imidazole-4-carboxamide | 442.1 | 0.65 (30% EtOAc in hexane) | 3.79 | 1 | 15 |
| 197 | 2-Et—Ph | 4-Cl—Ph | Ph | 1-(4-chlorophenyl)-2-(2-ethylphenyl)-N-phenyl-1H-imidazole-4-carboxamide | 402.1 | 0.4 (50% EtOAc in hexane) | 3.71 | 1 | 13, 14 |
| 198 | 2-Cl—Ph | 4-Cl—Ph | 4-pyridinyl | 2-(2-chlorophenyl)-1-(4-chlorophenyl)-N-(pyridinyl)-1H-imidazole-4-carboxamide | 409.5 | 0.37 (EtOAc) | 2.45 | 1 | 10, 11, 12 |

TABLE 8-continued

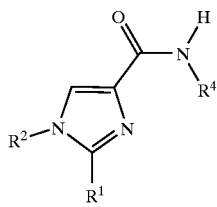

| Entry No. | R¹ | R² | R⁴ | IUPAC name | MS m/z [MH+] | TLC Rf (solvent) | HPLC RT (min) | HPLC method | Synthesis Method of Ex. No. |
|---|---|---|---|---|---|---|---|---|---|
| 199 | 2-Cl—Ph | 4-Cl—Ph | 4-CF₃-3-pyridinyl | 2-(2-chlorophenyl)-1-(4-chlorphenyl)-N-[4-(trifluoromethyl)-3-pyridinyl]-1H-imidazole-4-carboxamide | 477.3 | 0.44 (50% EtOAc in hexane) | 3.39 | 1 | 13, 14 |
| 200 | 2-Cl—Ph | 4-Cl—Ph | 4-Me-3-pyridinyl | 2-(2-chlorophenyl)-1-(4-chlorophenyl)-N-(4-methyl-3-pyridinyl)-1H-imidazole-4-carboxamide | 423.3 | 0.31 (EtOAc) | 2.41 | 1 | 8 |
| 201 | 2-Cl—Ph | 4-Cl—Ph | 4-pyrimidinyl | 2-(2-chlorophenyl)-1-(4-chlorophenyl)-N-(4-pyrimidinyl)-1H-imidazole-4-carboxamide hydrochloride | 410.4 | 0.27 (50% EtOAc in hexane) | 3.04 | 1 | 13, 14 |
| 202 | 2-Cl—Ph | 4-Cl—Ph | 2-pyrimidinyl | 2-(2-chlorophenyl)-1-(4-chlorophenyl)-N-(2-pyrimidinyl)-1H-imidazole-4-carboxamide | 410.6 | 0.32 (50% EtOAc in hexane) | 2.85 | 1 | 6 |
| 203 | 2-Cl—Ph | 4-Cl—Ph | 2-pyrazinyl | 2-(2-chlorophenyl)-1-(4-chlorophenyl)-N-(2-pyrazinyl)-1H-imidazole-4-carboxamide | 410.6 | 0.47 (75% EtOAc in hexane) | 3.18 | 1 | 6 |
| 204 | 2-Cl—Ph | 4-Cl—Ph | 5-CF₃-2-pyridinyl | 2-(2-chlorophenyl)-1-(4-chlorophenyl)-N-[5-(trifluoromethyl)-2-pyridinyl]-1H-imidazole-4-carboxamide | 477.2 | 0.4 (25% EtOAc in hexane) | 3.77 | 1 | 6 |

TABLE 9

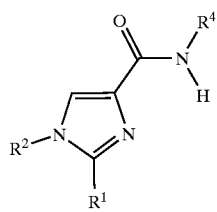

| Entry No. | R¹ | R² | R⁴ | IUPAC name | MS m/z [MH⁺] | TLC Rf (solvent) | HPLC RT (min.) | HPLC method | Synthesis method of Ex. No. |
|---|---|---|---|---|---|---|---|---|---|
| 205 | 4-Cl—Ph | 2,4-Cl₂—Ph | 2-(1-piperidinyl)ethyl | 2-(4-chlorophenyl)-1-(2,4-dichlorophenyl)-N-[2-(1-piperidinyl)ethyl]-1H-imidazole-4-carboxamide | 477 | | | | 13, 14 |
| 206 | 4-Cl—Ph | 2,4-Cl₂—Ph | 2-(Et₂N)ethyl | 2-(4-chlorophenyl)-1-(2,4-dichlorophenyl)-N-[2-(diethylamino)ethyl]-1H-imidazole-4-carboxamide | 465 | | 2.54 | 1 | 13, 14 |
| 207 | 4-Cl—Ph | 2,4-Cl₂—Ph | 2-(Me₂N)ethyl | 2-(4-chlorophenyl)-1-(2,4-dichlorophenyl)-N-[2-(dimethylamino)ethyl]-1H-imidazole-4-carboxamide | 437 | | 2.46 | 1 | 8 |
| 208 | 4-Cl—Ph | 2,4-Cl₂—Ph | 3-(Me₂N)-1-propyl | 2-(4-chlorophenyl)-1-(2,4-dichlorophenyl)-N-[3-(dimethylamino)propyl]-1H-imidazole-4-carboxamide | 451 | | 2.48 | 1 | 13, 14 |

TABLE 9-continued

| Entry No. | R¹ | R² | R⁴ | IUPAC name | MS m/z [MH⁺] | TLC Rf (solvent) | HPLC RT (min.) | HPLC method | Synthesis method of Ex. No. |
|---|---|---|---|---|---|---|---|---|---|
| 209 | 2-Cl—Ph | 4-Cl—Ph | endo-2-norbornyl | N-endo-bicyclo[2.2.1]hept-2-yl-2-(2-chlorophenyl)-1-(4-chlorophenyl)-1H-imidazole-4-carboxamide | 426 | 0.21 (40% EtOAc in hexane) | 3.50 | 1 | 15 |
| 210 | 2-Cl—Ph | 4-Cl—Ph | exo-2-norbornyl | N-exo-bicyclo[2.2.1]hept-2-yl-2-(2-chlorophenyl)-1-(4-chlorophenyl)-1H-imidazole-4-carboxamide | 426 | 0.19 (30% EtOAc in hexane) | 3.49 | 1 | 15 |
| 211 | 2-Cl—Ph | 4-Cl—Ph | 1-propyl | 2-(2-chlorophenyl)-1-(4-chlorophenyl)-N-propyl-1H-imidazole-4-carboxamide | 374 | 0.5 (30% EtOAc in hexane) | 3.10 | 1 | 15 |
| 212 | 2-Cl—Ph | 4-Cl—Ph | 3-pentyl | 2-(2-chlorophenyl)-1-(4-chlorophenyl)-N-(1-ethylpropyl)-1H-imidazole-4-carboxamide | 402 | 0.21 (30% EtOAc in hexane) | 3.33 | 1 | 13, 14 |
| 213 | 2-Cl—Ph | 4-Cl—Ph | 1,7,7-trimethylbicyclo[2.2.1]hept-2-yl | 2-(2-chlorphenyl)-1-(4-chlorophenyl)-N-(1,7,7-trimethyl-bicyclo[2.2.1]-hept-2-yl)-1H-imidazole-4-carboxamide | 468 | 0.29 (30% EtOAc in hexane) | 3.97 | 1 | 8 |
| 214 | 2-Cl—Ph | 4-Cl—Ph | trans-2-(HOCH₂)-cyclohexyl | trans-2-(2-chlorophenyl)-1-(4-chlorophenyl)-N-[2-(hydroxymethyl)cyclohexyl]-1H-imidazole-4-carboxamide | 444 | 30% EtOAc/Hexane | 3.51 | 2 | 10, 11, 12 |
| 215 | 2-Cl—Ph | 4-Cl—Ph | 2,3-dihydro-1,4-benzodioxin-2-yl-CH₂ | 2-(2-chlorophenyl)-1-(4-chlorophenyl)-N-(2,3-dihydro-1,4-benzodioxin-2-ylmethyl)-1H-imidazole-4-carboxamide | 480 | | 3.88 | 2 | 10, 11, 12 |
| 216 | 2-Cl—Ph | 4-Cl—Ph | 2,4-Cl₂-benzyl | 2-(2-chlorophenyl)-1-(4-chlorophenyl)-N-(2,4-dichlorobenzyl)-1H-imidazole-4-carboxamide | 490 | | 4.21 | 2 | 10, 11, 12 |
| 217 | 2-Cl—Ph | 4-Cl—Ph | 3-(1-pyrrolidinyl)-1-propyl | 2-(2-chlorophenyl)-1-(4-chlorophenyl)-N-[3-(1-pyrrolidinyl)propyl]-1H-imidazole-carboxamide hydrochloride | 443 | | 2.48 | 2 | 10, 11, 12 |
| 218 | 2,4-Cl₂—Ph | 4-Cl—Ph | 3-(1-pyrrolidinyl)-1-propyl | 1-(4-chlorophenyl)-2-(2,4-dichlorophenyl)-N-[3-(1-pyrrolidinyl)propyl]-1H-imidazole-4-carboxamide | 477 | 0.67 (40% 2M NH3/MeOH in EtOAc) | 2.45 | 1 | 13, 14 |
| 219 | 2-CF₃—Ph | 4-Cl—Ph | 3-(1-pyrrolidinyl)-1-propyl | 1-(4-chlorophenyl)-N-[3-(1-pyrrolidinyl)propyl]-2-[2-(trifluoromethyl)phenyl]-1H-imidazole-4-carboxamide | 477 | | 2.55 | 2 | 10, 11, 12 |
| 220 | 2-Cl—Ph | 4-Cl—Ph | 1-benzyl-4-piperidinyl | N-(1-benzyl-4-piperidinyl)-2-(2-chlorophenyl)-1-(4-chlorophenyl)-1H-imidazole-4-carboxamide | 505 | | 2.66 | 2 | 10, 11, 12 |
| 221 | 2-Cl—Ph | 4-Cl—Ph | 1-CO₂Et-4-piperidinyl | ethyl-4-({[2-(2-chlorophenyl)-1-(4-chlorophenyl)-1H-imidazol-4-yl]carbonyl}-amino-1-piperidine carboxylate) | 487 | 0.25 (83% EtOAc in hexane) | 3.01 | 1 | 13, 14 |
| 222 | 2,4-Cl₂—Ph | 4-MeO—Ph | trans-2-(HOCH₂)-cyclohexyl | trans-2-(2,4-dichlorophenyl)-N-[2-(hydroxymethyl)-cyclohexyl]-1-(4-methoxyphenyl)-1H-imidazole-4-carboxamide | 474 | | 3.58 | 2 | 10, 11, 12 |

TABLE 9-continued

| Entry No. | R¹ | R² | R⁴ | IUPAC name | MS m/z [MH⁺] | TLC Rf (solvent) | HPLC RT (min.) | HPLC method | Synthesis method of Ex. No. |
|---|---|---|---|---|---|---|---|---|---|
| 223 | 2,4-Cl₂—Ph | 4-MeO—Ph | 1-benzyl-4-piperidinyl | N-(1-benzyl-4-piperidinyl)-2-(2,4-dichlorophenyl)-1-(4-methoxyphenyl)-1H-imidazole-4-carboxamide | 535 | | 2.74 | 2 | 10, 11, 12 |
| 224 | 2-Cl—Ph | 4-Cl—Ph | 4-piperidinyl | 2-(2-chlorophenyl)-1-(4-chlorophenyl)-N-(4-piperidinyl)-1H-imidazole-4-carboxamide | 415 | 0.25 (50% 2M NH3/MeOH in EtOAc) | 2.22 | 1 | 37 |
| 225 | 2,4-Cl₂—Ph | 4-MeO—Ph | cis-2-(HOCH₂)-cyclohexyl | cis-2-(2,4-dichlorophenyl)-N-[2-(hydroxymethyl)-cyclohexyl]-1-(4-methoxyphenyl)-1H-imidazole-4-carboxamide | 474 | | 3.69 | 2 | 10, 11, 12 |
| 226 | 2,4-Cl₂—Ph | 4-MeO—Ph | cis-2-OH-cycloheptyl-CH₂ | cis-2-(2,4-dichlorophenyl)-N-{2-hydroxycycloheptyl]-methyl}-1-(4-methoxyphenyl)-1H-imidazole-4-carboxamide | 488 | | 3.66 | 2 | 10, 11, 12 |
| 227 | 2,4-Cl₂—Ph | 4-MeO—Ph | trans-2-OH-cyclohexyl-CH₂ | trans-2-(2,4-dichlorophenyl)-N-{[2-hydroxycyclohexyl]methyl}-1-(4-methoxyphenyl)-1H-imidazole-4-carboxamide | 474 | | 3.47 | 2 | 10, 11, 12 |
| 228 | 2,4-Cl₂—Ph | 4-MeO—Ph | 2-exo-HOCH₂-2-exo-norbornyl | exo,exo-2-(2,4-dichlorophenyl)-N-[3-(hydroxymethyl)-bicyclo[2.2.1]-hept-2-yl]-1-(4-methoxyphenyl)-1H-imidazole-4-carboxamide | 486 | | 3.44 | 2 | 10, 11, 12 |
| 229 | 2-Cl—Ph | 4-Cl—Ph | 1-Me-4-piperidinyl | 2-(2-chlorophenyl)-1-(4-chlorophenyl)-N-(1-methyl-4-piperidinyl)-1H-imidazole-4-carboxamide | 429 | 0.31 (90% MeOH in 2M NH3 in MeOH | 2.27 | 1 | 13, 14 |
| 230 | 2-Cl—Ph | 4-Cl—Ph | 1-(2-pyridinyl)-4-piperidinyl | 2-(2-chlorophenyl)-1-(4-chlorophenyl)-N-[1-(2-pyridinyl)-4-piperidinyl]-1H-imidazole-4-carboxamide | 492 | 0.33 (33% EtOAc in hexane) | 2.47 | 1 | 13, 14 |
| 231 | 2-Cl—Ph | 4-Cl—Ph | trans-2-(acetyloxy)-cyclohexyl | trans-2-({[2-(2-chlorophenyl)-1-(4-chlorophenyl)-1H-imidazol-4-yl]carbonyl}-amino)cyclohexyl acetate | 472 | 0.33 (50% EtOAc in hexane) | 3.25 | 1 | 13, 14 |
| 232 | 2-Cl—Ph | 4-Cl—Ph | 1-benzyl-3-pyrrolidinyl | N-(1-benzyl-3-pyrrolidinyl)-2-(2-chlorophenyl)-1-(4-chlorophenyl)-1H-imidazole-4-carboxamide hydrochloride | 491 | | 2.34 | 2 | 10, 11, 12 |
| 233 | 2-Cl—Ph | 4-Cl—Ph | 1-Et-2-pyrrolidinyl-CH₂ | 2-(2-chlorophenyl)-1-(4-chlorophenyl)-N-[(1-ethyl-2-pyrrolidinyl)methyl]-1H-imidazole-4-carboxamide hydrochloride | 443 | | 2.26 | 2 | 10, 11, 12 |
| 234 | 2,4-Cl₂— | 4-Cl—Ph | (R,R)-2-amino-cyclohexyl | N-[(1R,2R)-2-aminocyclohexyl]-1-(4-chlorophenyl)-2-(2,4-dichlorophenyl)-1H-imidazole-4-carboxamide hydrochloride | 463 | | 2.37 | 2 | 10, 11, 12 |

TABLE 9-continued

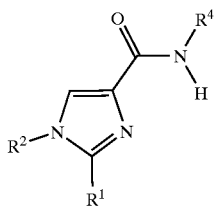

| Entry No. | R[1] | R[2] | R[4] | IUPAC name | MS m/z [MH+] | TLC Rf (solvent) | HPLC RT (min.) | HPLC method | Synthesis method of Ex. No. |
|---|---|---|---|---|---|---|---|---|---|
| 235 | 2,4-Cl$_2$—Ph | 4-Cl—Ph | (S,S)-2-amino-cyclohexyl | N-[(1S,2S)-2-aminocyclohexyl]-1-(4-chlorophenyl)-2-(2,4-dichlorophenyl)-1H-imidazole-4-carboxamide hydrochloride | 463 | | 2.34 | 2 | 10, 11, 12 |

TABLE 10

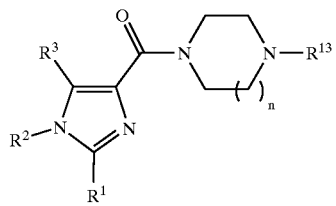

| Entry No. | R[1] | R[2] | R[3] | n | R[13] | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 236 | 2,4-Cl$_2$—Ph | 4-Cl—Ph | H | 1 | 2,3-Me$_2$—Ph | 1-{[1-(4-chlorophenyl)-2-(2,4-dichlorophenyl)-1H-imidazol-4-yl]carbonyl}-4-(2,3-dimethylphenyl)-piperazine | 539 | 0.55 (50% EtOAc in hexane) | 4.17 | 1 | 13, 14 |
| 237 | 2,4-Cl$_2$—Ph | 4-Cl—Ph | H | 1 | 2,4-F$_2$—Ph | 1-{[1-(4-chlorophenyl)-2-(2,4-dichlorophenyl)-1H-imidazol-4-yl]carbonyl}-4-(2,4-difluorophenyl)-piperazine | 549 | 0.27 (60% EtOAc in hexane) | 3.71 | 1 | 13, 14 |
| 238 | 2,4-Cl$_2$—Ph | 4-Cl—Ph | H | 1 | 2-CN—Ph | 2-(4-{[1-(4-chlorophenyl)-2-(2,4-dichlorophenyl)-1H-imidazol-4-yl]carbonyl}-1-piperazinyl)-benzonitrile | 536 | 0.73 (EtOAc) | 3.69 | 1 | 13, 14 |
| 239 | 2,4-Cl$_2$—Ph | 4-Cl—Ph | H | 1 | 2-phenyl-ethyl | 1-{[1-(4-chlorophenyl)-2-(2,4-dichlorophenyl)-1H-imidazol-4-yl]carbonyl}-4-(2-phenylethyl)-piperazine | 539 | 0.30 (2% MeOH in EtOAc) | 2.79 | 1 | 13, 14 |
| 240 | 2,4-Cl$_2$—Ph | 4-Cl—Ph | H | 1 | 2-pyridinyl | 1-{[1-(4-chlorophenyl)-2-(2,4-dichlorophenyl)-1H-imidazol-4-yl]carbonyl}-4-(2-pyridinyl)-piperazine | 512 | 0.6 (EtOAc) | 2.48 | 1 | 10, 11, 12 |

TABLE 10-continued

| Entry No. | R[1] | R[2] | R[3] | n | R[13] | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 241 | 2,4-Cl$_2$—Ph | 4-Cl—Ph | H | 1 | 3-CF$_3$—Ph | 1-{[1-(4-chlorophenyl)-2-(2,4-dichlorophenyl)-1H-imidazol-4-yl]carbonyl}-4-[3-(trifluoro-methyl)phenyl]-piperazine | 579 | 0.44 (50% EtOAc in hexane) | 4.11 | 1 | 13, 14 |
| 242 | 2,4-Cl$_2$—Ph | 4-Cl—Ph | H | 1 | 3-MeO—Ph | 1-{[1-(4-chlorophenyl)-2-(2,4-dichlorophenyl)-1H-imidazol-4-yl]carbonyl}-4-(3-methoxyphenyl)-piperazine | 541 | 0.31 (60% EtOAc in hexane) | 3.62 | 1 | 13, 14 |
| 243 | 2,4-Cl$_2$—Ph | 4-Cl—Ph | H | 1 | 4-Cl—Ph | 1-(4-chlorophenyl)-4-{[1-(4-chlorophenyl)-2-(2,4-dichlorophenyl)-1H-imidazol-4-yl]carbonyl}-piperazine | 545 | 0.72 (EtOAc) | 4.13 | 1 | 13, 14 |
| 244 | 2,4-Cl$_2$—Ph | 4-Cl—Ph | H | 1 | 4-CN—Ph | 4-(4-{[1-(4-chlorophenyl)-2-(2,4-dichlorophenyl)-1H-imidazol-4-yl]-carbonyl}-1-piperazinyl)benzonitrile | 536 | 0.3 (66% EtOAc in hexane) | 3.61 | 1 | 13, 14 |
| 245 | 2,4-Cl$_2$—Ph | 4-Cl—Ph | H | 1 | benzyl | 1-benzyl-4-{[1-(4-chloro-phenyl)-2-(2,4-dichloro-phenyl)-1H-imidazol-4-yl]carbonyl}piperazine | 525 | 0.30 (EtOAc) | 2.62 | 1 | 13, 14 |
| 246 | 2,4-Cl$_2$—Ph | 4-Cl—Ph | H | 1 | cyclohexyl | 1-{[1-(4-chlorophenyl)-2-(2,4-dichlorophenyl)-1H-imidazol-4-yl]carbonyl}-4-cyclohexylpiperazine hydrochloride | 519 | 0.07 (EtOAc) | 2.61 | 1 | 13, 14 |
| 247 | 2,4-Cl$_2$—Ph | 4-F—Ph | H | 1 | 4-CF$_3$—Ph | 1-{[2-(2,4-dichlorophenyl)-1-(4-fluorophenyl)-1H-imidazol-4-yl]carbonyl}-4-[4-(trifluoromethyl)-phenyl]-piperazine trifluoroacetate | 563 | | 3.73 | 2 | 10, 11, 12 |
| 248 | 2,4-Cl$_2$—Ph | 4-MeO—Ph | H | 1 | 2-HO—Ph | 2-(4-{[2-(2,4-dichloro-phenyl)-1-(4-methoxy-phenyl)-1H-imidazol-4-yl]carbonyl}-1-piper-azinyl)phenol hydro-chloride | 523 | | 2.81 | 2 | 10, 11, 12 |
| 249 | 2,4-Cl$_2$—Ph | 4-MeO—Ph | H | 1 | 2-pyrazinyl | 2-(4-{[2-(2,4-dichloro-phenyl)-1-(4-methoxy-phenyl)-1H-imidazol-4-yl]carbonyl}-1-piper azine bis(trifluoro-acetate) | 509 | | 2.59 | 2 | 10, 11, 12 |

TABLE 10-continued

| Entry No. | R¹ | R² | R³ | n | R¹³ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 250 | 2,4-Cl₂—Ph | 4-MeO—Ph | H | 1 | 3-CF₃—Ph | 1-{[2-(2,4-dichloro-phenyl)-1-(4-methoxy-phenyl)-1H-imidazol-4-yl]carbonyl}-4-[3-(trifluoromethyl)-phenyl]piperazine hydrochloride | 575 | | 4.24 | 2 | 10, 11, 12 |
| 251 | 2,4-Cl₂—Ph | 4-MeO—Ph | H | 1 | 6-Me-2-pyridinyl | 1-{[2-(2,4-dichloro-phenyl)-1-(4-methoxy-phenyl)-1H-imidazol-4-yl]carbonyl}-4-(6-methyl-2-pyridin-yl)piperazine hydrochloride | 522 | | 2.19 | 2 | 10, 11, 12 |
| 252 | 2,4-Cl₂—Ph | 4-MeO—Ph | H | 1 | 4-CF₃Ph | 1-{[2-(2,4-dichloro-phenyl)-1-(4-methoxy-phenyl)-1H-imidazol-4-yl]carbonyl}-4-[4-(trifluoromethyl)-phenyl]piperazine | 574 | | 4.34 | 2 | 10, 11, 12 |
| 253 | 2,4-Cl₂—Ph | 4-MeO—Ph | H | 1 | 4-CF₃—Ph | 1-{[2-(2,4-dichloro-phenyl)-1-(4-methoxy-phenyl)-1H-imidazol-4-yl]carbonyl}-4-[4-(trifluoromethyl)-phenyl]piperazine hydrochloride | 574 | | 4.34 | 2 | 10, 11, 12 |
| 254 | 2,4-Cl₂—Ph | 4-MeO—Ph | H | 1 | 4-HO—Ph | 4-(4-{[2-(2,4-dichloro-phenyl)-1-(4-methoxy-phenyl)-1H-imidazol-4-yl]carbonyl}-1-piperazinyl)phenol hydrochloride | 523 | | 2.52 | 2 | 10, 11, 12 |
| 255 | 2,4-Cl₂—Ph | 4-MeO—Ph | H | 1 | 4-pyridinyl | 1-{[2-(2,4-dichloro-phenyl)-1-(4-methoxy-phenyl)-1H-imidazol-4-yl]carbonyl}-4-(4-pyridinyl)piperazine hydrochloride | 508 | | 2.56 | 2 | 10, 11, 12 |
| 256 | 2,4-Cl₂—Ph | 4-MeO—Ph | H | 1 | 4-pyridinyl methyl | 1-{[2-(2,4-dichloro-phenyl)-1-(4-methoxy-phenyl)-1H-imidazol-4-yl]carbonyl}-4-(4-pyridinylmethyl)-piperazine dihydro-chloride | 522 | | 2.04 | 2 | 10, 11, 12 |
| 257 | 2,5-Cl₂—Ph | 4-Cl—Ph | H | 1 | 4-CN—Ph | 4-(4-{[1-(4-chloro-phenyl)-2-(2,5-dichloro-phenyl)-1H-imidazol-4-yl]-carbonyl}-1-piper-zinyl)benzonitrile | 536 | | 3.69 | 1 | 8 |

TABLE 10-continued

| Entry No. | R¹ | R² | R³ | n | R¹³ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 258 | 2-CF₃—Ph | 4-Cl—Ph | H | 1 | 3-CF₃—Ph | 1-({1-(4-chlorophenyl)-2-[2-(trifluoromethyl)phenyl]-1H-imidazol-4-yl}-carbonyl)-4-[3-(trifluoromethyl)phenyl]-piperazine hydrochloride | 579 | | 4.25 | 2 | 10, 11, 12 |
| 259 | 2-Cl—Ph | 4-Cl—Ph | H | 1 | 2,4-F₂—Ph | 1-{[2-(2-chlorophenyl)-1-(4-chlorophenyl)-1H-imidazol-4-yl]carbonyl}-4-(2,4-difluorophenyl)-piperazine hydrochloride | 513 | | 3.4 | 2 | 10, 11, 12 |
| 260 | 2-Cl—Ph | 4-Cl—Ph | H | 1 | 2-CN—Ph | 2-(4-{[2-(2-chlorophenyl)-1-(4-chlorophenyl)-1H-imidazol-4-yl]carbonyl}-1-piperazinyl)benzonitrile hydrochloride | 502 | | 3.25 | 2 | 10, 11, 12 |
| 261 | 2-Cl—Ph | 4-Cl—Ph | H | 1 | 2-HO—Ph | 2-(4-{[2-(2-chlorophenyl)-1-(4-chlorophenyl)-1H-imidazol-4-yl]carbonyl}-1-piperazinyl)phenol hydrochloride | 493 | | 2.78 | 2 | 10, 11, 12 |
| 262 | 2-Cl—Ph | 4-Cl—Ph | H | 1 | 2-hydroxyethyl | 2-(4-{[2-(2-chlorophenyl)-1-(4-chlorophenyl)-1H-imidazol-4-yl]carbonyl}-1-piperazinyl)ethanol hydrochloride | 445 | | 2.42 | 2 | 10, 11, 12 |
| 263 | 2-Cl—Ph | 4-Cl—Ph | H | 1 | 2-pyridinyl | 1-{[2-(2-chlorophenyl)-1-(4-chlorophenyl)-1H-imidazol-4-yl]carbonyl}-4-(2-pyridinyl)piperazine dihydrochloride | 478 | | 2.63 | 2 | 10, 11, 12 |
| 264 | 2-Cl—Ph | 4-Cl—Ph | H | 1 | 3-CF₃—Ph | 1-{[2-(2-chlorophenyl)-1-(4-chlorophenyl)-1H-imidazol-4-yl]carbonyl}-4-[3-(trifluoromethyl)phenyl]piperazine hydrochloride | 545 | | 4.24 | 2 | 10, 11, 12 |
| 265 | 2-Cl—Ph | 4-Cl—Ph | H | 1 | 3-Cl—Ph | 1-(3-chlorophenyl)-4-{[2-(2-chlorophenyl)-1-(4-chlorophenyl)-1H-imidazol-4-yl]carbonyl}piperzine hydrochloride | 511 | | 4.13 | 2 | 10, 11, 12 |
| 266 | 2-Cl—Ph | 4-Cl—Ph | cyclo-Pr | 1 | 4-CF₃—Ph | 1-{[2-(2-chlorophenyl)-1-(4-chlorophenyl)-5-cyclopropyl-1H-imidazol-4-yl]carbonyl}-4-[4-(trifluoromethyl)phenyl]piperazine hydrochloride | 585 | | 3.7 | 2 | 13, 14 |

TABLE 10-continued

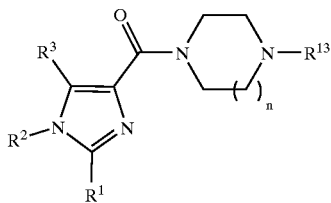

| Entry No. | R¹ | R² | R³ | n | R¹³ | IUPAC name | MS m/z [MH+] | TLC Rf (solvent) | HPLC RT (min) | HPLC method | Synthesis Method of Ex. No. |
|---|---|---|---|---|---|---|---|---|---|---|---|
| 267 | 2-Cl—Ph | 4-Cl—Ph | H | 1 | 4-CF₃—Ph | 1-{[2-(2-chloro-phenyl)-1-(4-chloro-phenyl)-1H-imidazol-4-yl]carbonyl}-4-[4-(trifluoro-methyl)phenyl]piperazine hydrochloride | 545 | | 4.21 | 2 | 10, 11, 12 |
| 268 | 2-Cl—Ph | 4-Cl—Ph | cyclo-Pr | 1 | 4-CN—Ph | 4-(4-{[2-(2-chloro-phenyl)-1-(4-chloro-phenyl)-5-cyclopropyl-1H-imidazol-4-yl]carbonyl}-1-piperazinyl)benzonitrile hydrochloride | 542 | | 3.29 | 2 | 13, 14 |
| 269 | 2-Cl—Ph | 4-Cl—Ph | H | 1 | 4-CN—Ph | 4-(4-{[2-(2-chloro-phenyl)-1-(4-chloro-phenyl)-1H-imidazol-4-yl]carbonyl}-1-piperazinyl)benzonitrile | 502 | | 3.18 | 2 | 10, 11, 12 |
| 270 | 2-Cl—Ph | 4-Cl—Ph | H | 2 | 4-F-benzyl | 1-{[2-(2-chloro-phenyl)-1-(4-chloro-phenyl)-1H-imidazol-4-yl]carbonyl}-4-(4-fluorobenzyl)-1,4-diazepane hydrochloride | 523 | | 2.68 | 2 | 10, 11, 12 |
| 271 | 2-Cl—Ph | 4-Cl—Ph | H | 1 | 4-F-benzyl | 1-{[2-(2-chloro-phenyl)-1-(4-chloro-phenyl)-1H-imidazol-4-yl]carbonyl}-4-(4-fluorobenzyl)piperazine hydrochloride | 509 | | 2.67 | 2 | 10, 11, 12 |
| 272 | 2-Cl—Ph | 4-Cl—Ph | H | 1 | 4-HO—Ph | 4-(4-{[2-(2-chloro-phenyl)-1-(4-chloro-phenyl)-1H-imidazol-4-yl]carbonyl}-1-piperazinyl)phenol hydrochloride | 493 | | 2.44 | 2 | 10, 11, 12 |
| 273 | 2-Cl—Ph | 4-Cl—Ph | H | 1 | cyclohexyl | 1-{[2-(2-chloro-phenyl)-1-(4-chloro-phenyl)-1H-imidazol-4-yl]carbonyl}-4-cyclohexylpiperazine hydrochloride | 483 | | 2.63 | 2 | 10, 11, 12 |
| 274 | 2-Cl—Ph | 4-Me—Ph | H | 1 | 2-hydroxyethyl | 2-(4-{[2-(2-chloro-phenyl)-1-(4-methyl-phenyl)-1H-imidazol-4-yl]carbonyl}-1-piperazinyl)ethanol hydrochloride | 425 | | 2.34 | 2 | 10, 11, 12 |
| 275 | 2-Cl—Ph | 4-NO₂—Ph | Me | 1 | 3-CF₃—Ph | 1-{[2-(2-chloro-phenyl)-5-methyl-1-(4-nitrophenyl)-1H-imidazol-4-yl]carbonyl}-4-[3-(trifluoromethyl)phenyl]piperazine | 570 | 0.35 (67% EtOAc in hexane) | 3.64 | 1 | 8 |

TABLE 11

[Structure: imidazole-4-carboxamide with substituents R1, R2, R3, R4 where R4 is on amide N-H]

| Entry No. | R1 | R2 | R3 | R4 | IUPAC name | MS m/z [MH+] | TLC (solvent) | HPLC ret. time (min) | HPLC method | Synthesis Method of Ex. No. |
|---|---|---|---|---|---|---|---|---|---|---|
| 276 | 2-Cl-Ph | 4-Cl-Ph | H | (1S,2S)-2-(benzyloxy)cyclohexyl | N-[(1S,2S)-2-(benzyloxy)cyclohexyl]-2-(2-chlorophenyl)-1-(4-chlorophenyl)-1H-imidazole-4-carboxamide | 520.3 | 0.35 (60% EtOAc in Hexane) | 3.69 | 1 | 13, 14 |
| 277 | 2-Cl-Ph | 4-Cl-Ph | H | (1R,2R)-2-(benzyloxy)cyclopentyl | N-[(1R,2R)-2-(benzyloxy)cyclopentyl]-2-(2-chlorophenyl)-1-(4-chlorophenyl)-1H-imidazole-4-carboxamide | 506.3 | 0.56 (50% EtOAc in Hexane) | 3.51 | 1 | 13, 14 |
| 278 | 2,4-Cl2-Ph | 4-Cl-Ph | H | (1R,2R)-2-(benzyloxy)cyclohexyl | N-[(1R,2R)-2-(benzyloxy)cyclohexyl]-1-(4-chlorophenyl)-2-(2,4-dichlorophenyl)-1H-imidazole-4-carboxamide | 554.4 | 0.46 (50% EtOAc in Hexane) | 3.99 | 1 | 13, 14 |
| 279 | 2,4-Cl2-Ph | 4-Cl-Ph | H | (1S,2S)-2-(benzyloxy)cyclohexyl | N-[(1S,2S)-2-(benzyloxy)cyclohexyl]-1-(4-chlorophenyl)-2-(2,4-dichlorophenyl)-1H-imidazole-4-carboxamide | 554.4 | 0.46 (50% EtOAc in Hexane) | 4.00 | 1 | 13, 14 |
| 280 | 2-Cl-Ph | 4-Cl-Ph | H | (1R,2R)-2-(benzyloxy)cyclohexyl | N-[(1R,2R)-2-(benzyloxy)cyclohexyl]-2-(2-chlorophenyl)-1-(4-chlorophenyl)-1H-imidazole-4-carboxamide | 520.3 | 0.33 (66% EtOAc in Hexane) | 3.67 | 1 | 13, 14 |
| 281 | 2,4-Cl2-Ph | 4-Cl-Ph | H | (1R,2R)-2-(benzyloxy)cyclopentyl | N-[(1R,2R)-2-(benzyloxy)cyclopentyl]-1-(4-chlorophenyl)-2-(2,4-dichlorophenyl)-1H-imidazole-4-carboxamide | 540.0 | 0.41 (40% EtOAc in Hexane) | 4.07 | 1 | 13, 14 |
| 282 | 2,4-Cl2-Ph | 4-Cl-Ph | H | (1S,2S)-2-(benzyloxy)cyclopentyl | N-[(1S,2S)-2-(benzyloxy)cyclopentyl]-1-(4-chlorophenyl)-2-(2,4-dichlorophenyl)-1H-imidazole-4-carboxamide | 540.0 | 0.41 (40% EtOAc in Hexane) | 4.07 | 1 | 13, 14 |
| 283 | 2-Cl-Ph | 4-Cl-Ph | H | (1S,2S)-2-(benzyloxy)cyclopentyl | N-[(1S,2S)-2-(benzyloxy)cyclopentyl]-2-(2-chlorophenyl)-1-(4-chlorophenyl)-1H-imidazole-4-carboxamide | 506.1 | 0.32 (40% EtOAc in Hexane) | 3.78 | 1 | 13, 14 |
| 284 | 2-Cl-Ph | 4-Cl-Ph | Et | (1S,2S)-2-(benzyloxy)cyclohexyl | N-[(1S,2S)-2-(benzyloxy)cyclohexyl]-2-(2-chlorophenyl)-1-(4-chlorophenyl)-5-ethyl-1H-imidazole-4-carboxamide | 548.6 | 0.33 (33% EtOAc in Hexane) | 3.81 | 1 | 13, 14 |
| 285 | 2-Cl-Ph | 4-Cl-Ph | Pr | (1S,2S)-2-(benzyloxy)cyclohexyl | N-[(1S,2S)-2-(benzyloxy)cyclohexyl]-2-(2-chlorophenyl)-1-(4-chlorophenyl)-5-propyl-1H-imidazole-4-carboxamide | 562.2 | 0.20 (25% EtOAc in Hexane) | 4.18 | 1 | 13, 14 |
| 286 | 2-Cl-Ph | 4-Cl-Ph | H | trans-2-(ethoxycarbonylmethoxy)cyclohexyl | ethyl {[trans-2-({[2-(2-chlorophenyl)-1-(4-chlorophenyl)-1H-imidazol-4-yl]carbonyl}amino)cyclohexyl]oxy}acetate | 516.2 | 0.37 (67% EtOAc in Hexane) | 3.37 | 1 | 13, 14 |
| 287 | 2-Cl-Ph | 4-Cl-Ph | H | trans-2-(2'-hydroxyethoxy)cyclohexyl | N-[trans-2-(2-hydroxyethoxy)cyclohexyl]-2-(2-chlorophenyl)-1-(4-chlorophenyl)-1H-imidazole-4-carboxamide | 474.8 | 0.17 (EtOAC) | 2.91 | 1 | 13, 14 |

TABLE 11-continued

| Entry No. | R¹ | R² | R³ | R⁴ | IUPAC name | MS m/z [MH+] | TLC (solvent) | HPLC ret. time (min) | HPLC method | Synthesis Method of Ex. No. |
|---|---|---|---|---|---|---|---|---|---|---|
| 288 | 2-Cl-Ph | 4-Br-Ph | Et | (1S,2S)-2-(benzyloxy) cyclohexyl | N-[(1S,2S)-2-(benzyloxy)cyclohexyl]-1-(4-bromophenyl)-2-(2-chlorophenyl)-5-ethyl-1H-imidazole-4-carboxamide | 592.9 | 0.29 (33% EtOAc in Hexane) | 4.31 | 1 | 13, 14 |
| 289 | 2-Cl-Ph | 4-iPr-Ph | Et | (1S,2S)-2-(benzyloxy) cyclohexyl | N-[(1S,2S)-2-(benzyloxy)cyclohexyl]-1-(4-isopropylphenyl)-2-(2-chlorophenyl)-5-ethyl-1H-imidazole-4-carboxamide | 556.3 | 0.79 (2:1 EtOAc/Hexane) | 4.09 | 1 | 13, 14 |
| 290 | 2-Cl-Ph | 4-Cl-Ph | Br | (1S,2S)-2-(benzyloxy) cyclohexyl | N-[(1S,2S)-2-(benzyloxy)cyclohexyl]-5-bromo-2-(2-chlorophenyl)-1-(4-chlorophenyl)-1H-imidazole-4-carboxamide | 598 | | 3.80 | 2 | 13, 14 |
| 291 | 2-Cl-Ph | 4-MeO-Ph | Pr | (1S,2S)-2-(benzyloxy) cyclohexyl | N-[(1S,2S)-2-(benzyloxy)cyclohexyl]-2-(2-chlorophenyl)-1-(4-methoxyphenyl)-5-propyl-1H-imidazole-4-carboxamide | 583.3 | 0.60 (1:1 EtOAc/Hexane) | 3.86 | 1 | 13, 14 |
| 292 | 2-Cl-Ph | 4-F-Ph | Pr | (1S,2S)-2-(benzyloxy) cyclohexyl | N-[(1S,2S)-2-(benzyloxy)cyclohexyl]-2-(2-chlorophenyl)-1-(4-fluorophenyl)-5-propyl-1H-imidazole-4-carboxamide | 546.3 | 0.19 (1:1 EOAc/Hexane) | 3.90 | 1 | 13, 14 |
| 293 | 2-Cl-Ph | 3-Cl-Ph | Pr | (1S,2S)-2-(benzyloxy) cyclohexyl | N-[(1S,2S)-2-(benzyloxy)cyclohexyl]-2-(2-chlorophenyl)-1-(3-chlorophenyl)-5-propyl-1H-imidazole-4-carboxamide | 562.3 | 0.73 (1:1 EtOAc/Hexane) | 4.07 | 1 | 13, 14 |
| 294 | 2-Cl-Ph | 2-Cl-4-F-Ph | H | (1S,2S)-2-(benzyloxy) cyclohexyl | N-[(1S,2S)-2-(benzyloxy)cyclohexyl]-2-(2-chlorophenyl)-1-(2-chloro-4-fluorophenyl)-1H-imidazole-4-carboxamide | 538.2 | 0.44 (1:1 EtOAc/Hexane) | 3.64 | 1 | 13, 14 |
| 295 | 2-Cl-Ph | 2,4-F₂-Ph | H | (1S,2S)-2-(benzyloxy) cyclohexyl | N-[(1S,2S)-2-(benzyloxy)cyclohexyl]-2-(2-chlorophenyl)-1-(2,4-difluorophenyl)-1H-imidazole-4-carboxamide | 522.2 | 0.29 (1:1 EtOAc/Hexane) | 3.56 | 1 | 13, 14 |
| 296 | 2-Cl-Ph | 4-CF₃O-Ph | Pr | (1S,2S)-2-(benzyloxy) cyclohexyl | N-[(1S,2S)-2-(benzyloxy)cyclohexyl]-2-(2-chlorophenyl)-1-(4-trifluoromethoxyphenyl)-5-propyl-1H-imidazole-4-carboxamide | 612.3 | 0.41(1:1 EtOAc/Hexane) | 4.17 | 1 | 13, 14 |
| 297 | 2-Cl-Ph | 4-Cl-Ph | i-Pr | (1S,2S)-2-(benzyloxy) cyclohexyl | N-[(1S,2S)-2-(benzyloxy)cyclohexyl]-2-(2-chlorophenyl)-1-(4-chlorophenyl)-5-isopropyl-1H-imidazole-4-carboxamide | 562 | | 3.98 | 2 | 13, 14 |
| 298 | 2-Cl-Ph | 4-Cl-Ph | cyclo-Pr | (1S,2S)-2-(benzyloxy) cyclohexyl | N-[(1S,2S)-2-(benzyloxy)cyclohexyl]-2-(2-chlorophenyl)-1-(4-chlorophenyl)-5-cyclopropyl-1H-imidazole-4-carboxamide | 560.3 | | 3.72 | 2 | 13, 14 |

TABLE 12

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 299 | 2-Cl-Ph | 4-i-Pr-Ph | Et | H | (1S,2S)-2-hydroxycyclohexyl | 2-(2-chlorophenyl)-5-ethyl-N-[(1S,2S)-2-hydroxycyclohexyl]-1-(4-isopropylphenyl)-1H-imidazole-4-carboxamide | 466 | 0.49 (2:1 EtOAc/Hexane) | 3.38 | 1 | 13, 14 |
| 300 | 2-Cl-Ph | 4-MeO-Ph | n-Pr | H | (1S,2S)-2-hydroxycyclohexyl | 2-(2-chlorophenyl)-5-propyl-N-[(1S,2S)-2-hydroxycyclohexyl]-1-(4-methoxyphenyl)-1H-imidazole-4-carboxamide | 468 | 0.66 (EtOAc) | 3.09 | 1 | 13, 14 |
| 301 | 2-Cl-Ph | 4-F-Ph | n-Pr | H | (1S,2S)-2-hydroxycyclohexyl | 2-(2-chlorophenyl)-5-propyl-N-[(1S,2S)-2-hydroxycyclohexyl]-1-(4-fluorophenyl)-1H-imidazole-4-carboxamide | 456 | 0.35 (2:1 EtOAc/Hexane) | 3.16 | 1 | 13, 14 |
| 302 | 2-Cl-Ph | 3-Cl-Ph | n-Pr | H | (1S,2S)-2-hydroxycyclohexyl | 2-(2-chlorophenyl)-5-propyl-N-[(1S,2S)-2-hydroxycyclohexyl]-1-(3-chlorophenyl)-1H-imidazole-4-carboxamide | 472 | 0.45 (2:1 EtOAc/Hexane) | 3.29 | 1 | 13, 14 |
| 303 | 2-Cl-Ph | 2-Cl-4-F-Ph | H | H | (1S,2S)-2-hydroxycyclohexyl | 1-(2-chloro-4-fluorophenyl)-2-(2-chlorophenyl)-N-[(1S,2S)-2-hydroxycyclohexyl]-1H-imidazole-4-carboxamide | 448 | 0.5 (EtOAc) | 2.90 | 1 | 13, 14 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 304 | 2-Cl-Ph | 2,4-F₂-Ph | H | H | (2-methyl-2-hydroxycyclohexyl) | 2-(2-chlorophenyl)-1-(2,4-difluorophenyl)-N-[(1S,2S)-2-hydroxycyclohexyl]-1H-imidazole-4-carboxamide | 432 | 0.5 (EtOAc) | 2.82 | 1 | 13, 14 |
| 305 | 2-Cl-Ph | 4-Cl-Ph | H | H | (1-hydroxy-2-methyl-indanyl) | 2-(2-chlorophenyl)-1-(4-chlorophenyl)-N-[Cis-1-hydroxy-2,3-dihydro-1H-inden-2-yl]-1H-imidazole-4-carboxamide | 464 | | 3.16 | 1 | 13, 14 |
| 306 | 2-Cl-Ph | 4-Cl-Ph | H | H | (1-hydroxy-2-methyl-indanyl) | 2-(2-chlorophenyl)-1-(4-chlorophenyl)-N-[trans-1-hydroxy-2,3-dihydro-1H-inden-2-yl]-1H-imidazole-4-carboxamide | 464 | | 3.15 | 1 | 13, 14 |
| 307 | 2-Cl-Ph | 4-Cl-Ph | H | 2,4-(MeO)₂-Ph-CH₂— | (3-hydroxy-2-methyl-tetrahydronaphthalenyl) | 2-(2-chlorophenyl)-1-(4-chlorophenyl)-N-(2,4-dimethoxybenzyl)-N-[trans-3-hydroxy-1,2,3,4-tetrahydro-2-naphthalenyl]-1H-imidazole-4-carboxamide | 526 | 0.15 (1:1 EtOAc/Hexane) | 3.72 | 1 | 13, 14 |
| 308 | 2-Cl-Ph | 4-Cl-Ph | Br | H | (2-methyl-2-hydroxycyclohexyl) | 5-bromo-2-(2-chlorophenyl)-1-(4-chlorophenyl)-N-[(1S,2S)-2-hydroxycyclohexyl]-1H-imidazole-4-carboxamide | 508 | | 2.99 | 2 | 13, 14 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 309 | 2-Cl-Ph | 4-Cl-Ph | i-Pr | H | (2-hydroxycyclohexyl, 1S,2S) | 2-(2-chlorophenyl)-1-(4-chlorophenyl)-N-[(1S,2S)-2-hydroxycyclohexyl]-5-isopropyl-1H-imidazole-4-carboxamide | 472 | | 3.22 | 2 | 13, 14 |
| 310 | 2-Cl-Ph | 4-Cl-Ph | H | H | (trans-2-hydroxy-2,3-dihydro-1H-inden-1-yl) | 2-(2-chlorophenyl)-N-[trans-2-hydroxy-2,3-dihydro-1H-inden-1-yl]-1H-imidazole-4-carboxamide | 464 | | 3.05 | 2 | 10, 11, 12 |
| 311 | 2-Cl-Ph | 4-Cl-Ph | H | H | (3S-tetrahydroisoquinolinyl-methanol) | ((3S)-2-{[2-(2-chlorophenyl)-1H-imidazol-4-yl]carbonyl}-1,2,3,4-tetrahydro-3-isoquinolinyl)methanol | 478 | | 3.00 | 2 | 10, 11, 12 |
| 312 | 2-Cl-Ph | 4-Cl-Ph | H | H | (3-piperidinol) | 1-{[2-(2-chlorophenyl)-1H-imidazol-4-yl]carbonyl}-3-piperidinol | 416 | | 2.56 | 2 | 10, 11, 12 |
| 313 | 2-Cl-Ph | 4-Cl-Ph | H | H | ((2S)-2-pyrrolidinyl-methanol) | ((2S)-1-{[2-(2-chlorophenyl)-1H-imidazol-4-yl]carbonyl}-2-pyrrolidinyl)methanol | 416 | | 2.59 | 2 | 10, 11, 12 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 314 | 2,4-Cl₂-Ph | 4-MeO-Ph | H | H | 2-methylcyclohexyl with OH | 2-(2,4-dichlorophenyl)-N-[cis-2-hydroxycyclohexyl]-1-(4-methoxyphenyl)-1H-imidazole-4-carboxamide | 460 | | 3.69 | 2 | 10, 11, 12 |
| 315 | 2,4-Cl₂-Ph | 4-MeO-Ph | H | H | 2-methylcyclohexyl with OH | 2-(2,4-dichlorophenyl)-N-[trans-2-hydroxycyclohexyl]-1-(4-methoxyphenyl)-1H-imidazole-4-carboxamide | 460 | | 3.40 | 2 | 10, 11, 12 |
| 316 | 2-Me-Ph | 4-Cl-Ph | H | H | 2-methylcyclohexyl with OH | 1-(4-chlorophenyl)-N-[trans-2-hydroxycyclohexyl]-2-(2-methylphenyl)-1H-imidazole-4-carboxamide | 411 | | 2.74 | 2 | 10, 11, 12 |
| 317 | 2,4-Cl₂-Ph | 4-F-Ph | H | H | 2-methylcyclohexyl with OH | 1-(4-fluorophenyl)-N-[trans-2-hydroxycyclohexyl]-2-(2,4-dichlorophenyl)-1H-imidazole-4-carboxamide | 449 | | 2.85 | 2 | 10, 11, 12 |
| 318 | 2,4-Cl₂-Ph | 4-Cl-Ph | H | H | hydroxy-dimethyl indanyl | 1-(4-chlorophenyl)-2-(2,4-dichlorophenyl)-N-[(1S,2R)-2-hydroxy-2,3-dihydro-1H-inden-1-yl]-1H-imidazole-4-carboxamide | 498 | | 3.29 | 2 | 10, 11, 12 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 319 | 2,4-Cl₂-Ph | 4-Cl-Ph | H | H | (2-hydroxyindanyl) | 1-(4-chlorophenyl)-2-(2,4-dichlorophenyl)-N-[(1R,2S)-2-hydroxy-2,3-dihydro-1H-inden-1-yl]-1H-imidazole-4-carboxamide | 498 | | 3.29 | 2 | 10, 11, 12 |
| 320 | 2-Cl-Ph | 4-Cl-Ph | H | H | (2-hydroxyindanyl) | 1-(4-chlorophenyl)-2-(2-chlorophenyl)-N-[(1S,2R)-2-hydroxy-2,3-dihydro-1H-inden-1-yl]-1H-imidazole-4-carboxamide | 464 | | 3.11 | 2 | 10, 11, 12 |
| 321 | 2-Cl-Ph | 4-Cl-Ph | H | H | (2-hydroxyindanyl) | 1-(4-chlorophenyl)-2-(2-chlorophenyl)-N-[(1R,2S)-2-hydroxy-2,3-dihydro-1H-inden-1-yl]-1H-imidazole-4-carboxamide | 464 | | 3.11 | 2 | 10, 11, 12 |
| 322 | 2,4-Cl₂-Ph | 4-MeO-Ph | H | H | (2-hydroxy-1-phenylethyl) | 2-(2,4-dichlorophenyl)-N-[(1R)-2-hydroxy-1-phenylethyl]-1-(4-methoxyphenyl)-1H-imidazole-4-carboxamide | 483 | | 2.99 | 2 | 10, 11, 12 |
| 323 | 2,4-Cl₂-Ph | 4-MeO-Ph | H | H | (2-hydroxy-1-phenylethyl) | 2-(2,4-dichlorophenyl)-N-[(1S)-2-hydroxy-1-phenylethyl]-1-(4-methoxyphenyl)-1H-imidazole-4-carboxamide | 483 | | 2.96 | 2 | 10, 11, 12 |
| 324 | 2-Cl-Ph | 4-Cl-Ph | H | H | (2-hydroxy-1-phenylethyl) | 2-(2-chlorophenyl)-N-[(1R)-2-hydroxy-1-phenylethyl]-1-(4-chlorophenyl)-1H-imidazole-4-carboxamide | 452 | | 2.88 | 2 | 10, 11, 12 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 325 | 2-Cl-Ph | 4-Cl-Ph | H | H | | 2-(2-chlorophenyl)-N-[(1S)-2-hydroxy-1-phenylethyl]-1-(4-chlorophenyl)-1H-imidazole-4-carboxamide | 453 | | 2.89 | 2 | 10, 11, 12 |
| 326 | 2-Cl-Ph | 4-Cl-Ph | H | H | | 2-(2-chlorophenyl)-N-[1-(hydroxymethyl)cyclopentyl]-1H-imidazole-4-carboxamide | 431 | | 2.89 | 2 | 10, 11, 12 |
| 327 | 2-Cl-Ph | 4-Cl-Ph | H | H | | 2-(2-chlorophenyl)-1-(4-chlorophenyl)-N-[trans-2-hydroxy-1,2,3,4-tetrahydro-1-naphthalenyl]-1H-imidazole-4-carboxamide | 477 | | 2.92 | 2 | 10, 11, 12 |
| 328 | 2,4-Cl₂-Ph | 4-Cl-Ph | H | H | | 1-(4-chlorophenyl)-2-(2,4-dichlorophenyl)-N-[trans-2-hydroxycyclohexyl]-1H-imidazole-4-carboxamide | 464 | 0.14 (50% EtOAc in Hexane) | 3.20 | 1 | 13, 14 |
| 329 | 2-Cl-Ph | 4-Cl-Ph | H | H | | 2-(2-chlorophenyl)-1-(4-chlorophenyl)-N-[(1S,2S)-2-hydroxycyclopentyl]-1H-imidazole-4-carboxamide | 416 | 0.43 (50% EtOAc in Hexane) | 2.96 | 1 | 36 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 330 | 2,4-Cl₂-Ph | 4-Cl-Ph | H | H | cyclopentyl-OH | 1-(4-chlorophenyl)-2-(2,4-dichlorophenyl)-N-[(1R,2R)-2-hydroxycyclopentyl]-1H-imidazole-4-carboxamide | 450 | 0.45 (50% EtOAc in Hexane) | 3.24 | 1 | 36 |
| 331 | 2,4-Cl₂-Ph | 4-Cl-Ph | H | H | cyclopentyl-OH | 1-(4-chlorophenyl)-2-(2,4-dichlorophenyl)-N-[(1S,2S)-2-hydroxycyclopentyl]-1H-imidazole-4-carboxamide | 450 | 0.45 (50% EtOAc in Hexane) | 3.24 | 1 | 36 |
| 332 | 2,4-Cl₂-Ph | 4-Cl-Ph | H | H | cyclohexyl-OH | 1-(4-chlorophenyl)-2-(2,4-dichlorophenyl)-N-[(1R,2R)-2-hydroxycyclohexyl]-1H-imidazole-4-carboxamide | 464 | 0.67 (EtOAc) | 3.22 | 1 | 35 |
| 333 | 2-Cl-Ph | 4-Cl-Ph | H | H | cyclopentyl-OH | 2-(2-chlorophenyl)-1-(4-chlorophenyl)-N-[(1R,2R)-2-hydroxycyclopentyl]-1H-imidazole-4-carboxamide | 416 | 0.4 (EtOAc) | 2.83 | 1 | 36 |
| 334 | 2,4-Cl₂-Ph | 4-Cl-Ph | H | H | cyclohexyl-OH | 1-(4-chlorophenyl)-2-(2,4-dichlorophenyl)-N-[(1S,2S)-2-hydroxycyclohexyl]-1H-imidazole-4-carboxamide | 466 | 0.67 (EtOAc) | 3.32 | 1 | 35 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 335 | 2-Cl-Ph | 4-Cl-Ph | H | H | (bicyclic hydroxy structure) | 2-(2-chlorophenyl)-1-(4-chlorophenyl)-N-[(1S,2R,3S,4R)-3-hydroxy-4,7,7-trimethylbicyclo[2.2.1]hept-2-yl]-1H-imidazole-4-carboxamide | 484 | 0.22 (50% EtOAc in Hexane) | 3.55 | 1 | 8 |
| 336 | 2-Cl-Ph | 4-Cl-Ph | H | H | (hydroxycyclohexyl) | 2-(2-chlorophenyl)-1-(4-chlorophenyl)-N-[trans-2-hydroxycyclohexyl]-1H-imidazole-4-carboxamide | 430 | 0.45 (5% MeOH in CH2Cl2) | 2.95 | 1 | 13, 14 |
| 337 | 2-Cl-Ph | 4-Cl-Ph | H | H | (hydroxycyclohexyl) | 2-(2-chlorophenyl)-1-(4-chlorophenyl)-N-[cis-2-hydroxycyclohexyl]-1H-imidazole-4-carboxamide | 430 | 0.31 (66% EtOAc in Hexane) | 2.94 | 1 | 13, 14 |
| 338 | 2-Cl-Ph | 4-Cl-Ph | H | H | (hydroxycyclohexyl) | 2-(2-chlorophenyl)-1-(4-chlorophenyl)-N-[(1S,2S)-2-hydroxycyclohexyl]-1H-imidazole-4-carboxamide | 430 | 0.30 (66% EtOAc in Hexane) | 3.02 | 1 | 35 |
| 339 | 2-Cl-Ph | 4-Cl-Ph | H | H | (hydroxycyclohexyl) | 2-(2-chlorophenyl)-1-(4-chlorophenyl)-N-[(1R,2R)-2-hydroxycyclohexyl]-1H-imidazole-4-carboxamide | 430 | 0.30 (66% EtOAc in Hexane) | 2.96 | 1 | 35 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 340 | 2-Cl-Ph | 4-Cl-Ph | Et | H | (1S,2S)-2-hydroxycyclohexyl | 2-(2-chlorophenyl)-1-(4-chlorophenyl)-5-ethyl-N-[(1S,2S)-2-hydroxycyclohexyl]-1H-imidazole-4-carboxamide | 458 | 0.37 (75% EtOAc in Hexane) | 3.24 | 1 | 35 |
| 341 | 2-Cl-Ph | 4-Cl-Ph | n-Pr | H | (1S,2S)-2-hydroxycyclohexyl | 2-(2-chlorophenyl)-1-(4-chlorophenyl)-5-propyl-N-[(1S,2S)-2-hydroxycyclohexyl]-1H-imidazole-4-carboxamide | 472 | 0.41 (75% EtOAc in Hexane) | 3.38 | 1 | 35 |
| 342 | 2-Cl-Ph | 4-Br-Ph | Et | H | (1S,2S)-2-hydroxycyclohexyl | 2-(2-chlorophenyl)-1-(4-bromophenyl)-5-ethyl-N-[(1S,2S)-2-hydroxycyclohexyl]-1H-imidazole-4-carboxamide | 502 | 0.45 (EtOAc) | 3.19 | 1 | 35 |
| 343 | 2-Cl-Ph | 4-Cl-Ph | Me | H | (1S,2S)-2-hydroxycyclohexyl | 2-(2-chlorophenyl)-1-(4-chlorophenyl)-5-methyl-N-[(1S,2S)-2-hydroxycyclohexyl]-1H-imidazole-4-carboxamide | 444 | 0.29 (80% EtOAc in Hexane) | 3.06 | 1 | 35 |
| 344 | 2-Cl-Ph | 4-Cl-Ph | Et | H | (1S,2S)-2-hydroxycyclopentyl | 2-(2-chlorophenyl)-1-(4-chlorophenyl)-5-ethyl-N-[(1S,2S)-2-hydroxycyclopentyl]-1H-imidazole-4-carboxamide | 444 | 0.30 (67% EtOAc in Hexane) | 3.15 | 1 | 36 |

TABLE 12-continued

| Entry No. | R¹ | R² | R³ | R⁴ | R⁵ | IUPAC name | MS m/z [MH+] | TLC (solvent) | HPLC ret. time (min) | HPLC method | Synthesis Method of Ex. No. |
|---|---|---|---|---|---|---|---|---|---|---|---|
| 345 | 2-Cl-Ph | 4-Br-Ph | Et | H | (1S,2R,3S,4R)-3-hydroxy-4,7,7-trimethylbicyclo[2.2.1]hept-2-yl | 2-(2-chlorophenyl)-1-(4-bromophenyl)-N-[(1S,2R,3S,4R)-3-hydroxy-4,7,7-trimethylbicyclo[2.2.1]hept-2-yl]-5-ethyl-1H-imidazole-4-carboxamide | 556 | 0.40 (50% EtOAc in Hexane) | 3.97 | 1 | 8 |
| 346 | 2-Cl-Ph | 4-Br-Ph | Et | H | (1R,2S,3R,4S)-3-hydroxy-4,7,7-trimethylbicyclo[2.2.1]hept-2-yl | 2-(2-chlorophenyl)-1-(4-bromophenyl)-N-[(1R,2S,3R,4S)-3-hydroxy-4,7,7-trimethylbicyclo[2.2.1]hept-2-yl]-5-ethyl-1H-imidazole-4-carboxamide | 556 | 0.40 (50% EtOAc in Hexane) | 4.00 | 1 | 8 |
| 347 | 2-Cl-Ph | 4-Br-Ph | Et | H | (1R,2R)-2-hydroxycyclohexyl | 1-(4-bromophenyl)-2-(2-chlorophenyl)-5-ethyl-N-[(1R,2R)-2-hydroxycyclohexyl]-1H-imidazole-4-carboxamide | 502 | 0.45 (EtOAc) | 3.31 | 1 | 35 |
| 348 | 2-Cl-Ph | 4-Br-Ph | Et | H | cis-2-hydroxycyclohexyl | 1-(4-bromophenyl)-2-(2-chlorophenyl)-5-ethyl-N-[cis-2-hydroxycyclohexyl]-1H-imidazole-4-carboxamide | 502 | 0.26 (50% EtOAc in hexane) | 502.3 | 1 | 23 |

TABLE 13

| Entry No. | R¹ | R² | R³ | R¹⁴ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 349 | 2-Cl-Ph | 4-Cl-Ph | H | 1,1-dioxido-1-benzothien-2-yl | 1-{[2-(2-chlorophenyl)-1-(4-chlorophenyl)-1H-imidazol-4-yl]carbonyl}-4-(1,1-dioxido-1-benzothien-2-yl)-4-piperidinol | 580 | 0.29 (EtOAc) | 3.10 | 1 | 18 |
| 350 | 2-Cl-Ph | 4-Cl-Ph | H | 1,3-thiazol-2-yl | 1-{[2-(2-chlorophenyl)-1-(4-chlorophenyl)-1H-imidazol-4-yl]carbonyl}-4-(1,3-thiazol-2-yl)-4-piperidinol | 499 | 0.10 (1:2 Hexane/EtOAc) | 2.83 | 1 | 18 |
| 351 | 2-Cl-Ph | 4-Cl-Ph | H | 1-benzofuran-2-yl | 4-(1-benzofuran-2-yl)-1-{[2-(2-chlorophenyl)-1-(4-chlorophenyl)-1H-imidazol-4-yl]carbonyl}-4-piperidinol | 532 | 0.45 (EtOAc) | 3.44 | 1 | 18 |
| 352 | 2-Cl-Ph | 4-Cl-Ph | Et | 1-benzofuran-2-yl | 4-(1-benzofuran-2-yl)-1-{[2-(2-chlorophenyl)-1-(4-chlorophenyl)-5-ethyl-1H-imidazol-4-yl]carbonyl}-4-piperidinol | 560 | 0.39 (EtOAc) | 3.43 | 1 | 18 |
| 353 | 2-Cl-Ph | 4-Cl-Ph | nPr | 1-benzofuran-2-yl | 4-(1-benzofuran-2-yl)-1-{[2-(2-chlorophenyl)-1-(4-chlorophenyl)-5-propyl-1H-imidazol-4-yl]carbonyl}-4-piperidinol | 574 | 0.40 (EtOAc) | 3.55 | 1 | 18 |
| 354 | 2-Cl-Ph | 4-Cl-Ph | H | 1-benzothien-2-yl | 4-(1-benzothien-2-yl)-1-{[2-(2-chlorophenyl)-1-(4-chlorophenyl)-1H-imidazol-4-yl]carbonyl}-4-piperidinol | 548 | 0.50 (EtOAc) | 3.45 | 1 | 18 |
| 355 | 2-Cl-Ph | 4-Cl-Ph | nPr | 1-benzothien-2-yl | 4-(1-benzothien-2-yl)-1-{[2-(2-chlorophenyl)-1-(4-chlorophenyl)-5-propyl-1H-imidazol-4-yl]carbonyl}-4-piperidinol | 590 | 0.45 (EtOAc) | 3.66 | 1 | 18 |
| 356 | 2-Cl-Ph | 4-Cl-Ph | Et | 1-benzothien-2-yl | 4-(1-benzothien-2-yl)-1-{[2-(2-chlorophenyl)-1-(4-chlorophenyl)-5-ethyl-1H-imidazol-4-yl]carbonyl}-4-piperidinol | 576 | 0.44 (EtOAc) | 3.54 | 1 | 18 |
| 357 | 2-Cl-Ph | 4-Cl-Ph | H | 2,3-dihydro-1,4-benzodioxin-6-yl | 1-{[2-(2-chlorophenyl)-1-(4-chlorophenyl)-1H-imidazol-4-yl]carbonyl}-4-(2,3-dihydro-1,4-benzodioxin-6-yl)-4-piperidinol | 550 | 0.20 (1:2 Hexane/EtOAc) | 3.02 | 1 | 18 |

TABLE 13-continued

| Entry No. | R¹ | R² | R³ | R¹⁴ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 358 | 2-Cl-Ph | 4-Cl-Ph | H | 2,6-dimethyl-3-pyridinyl | 1-{[2-(2-chlorophenyl)-1H-imidazol-4-yl]carbonyl}-4-(2,6-dimethyl-3-pyridinyl)-4-piperidinol | 521 | 0.04 (EtOAc) | 2.24 | 1 | 18 |
| 359 | 2-Cl-Ph | 4-Cl-Ph | H | 2,4-(MeO)₂-Ph | 1-{[2-(2-chlorophenyl)-1H-imidazol-4-yl]carbonyl}-4-(2,4-dimethoxyphenyl)-4-piperidinol | 552 | 0.16 (1:2 Hexane/EtOAC) | 3.20 | 1 | 18 |
| 360 | 2-Cl-Ph | 4-Cl-Ph | H | 2,5-F₂-Ph | 1-{[2-(2-chlorophenyl)-1H-imidazol-4-yl]carbonyl}-4-(2,5-difluorophenyl)-4-piperidinol | 528 | 0.24 (1:2 Hexane/EtOAc) | 3.28 | 1 | 18 |
| 361 | 2-Cl-Ph | 4-Cl-Ph | H | 2,5-(MeO)₂-Ph | 1-{[2-(2-chlorophenyl)-1H-imidazol-4-yl]carbonyl}-4-(2,5-dimethoxyphenyl)-4-piperidinol | 552 | 0.23 (1:2 Hexane/EtOAc) | 3.15 | 1 | 18 |
| 362 | 2-Cl-Ph | 4-Cl-Ph | H | 2-CF₃O-Ph | 1-{[2-(2-chlorophenyl)-1H-imidazol-4-yl]carbonyl}-4-[2-(trifluoromethoxy)phenyl]-4-piperidinol | 576 | 0.22 (1:2 Hexane/EtOAc) | 3.45 | 1 | 18 |
| 363 | 2-Cl-Ph | 4-Cl-Ph | H | 2-CF₃-Ph | 1-{[2-(2-chlorophenyl)-1H-imidazol-4-yl]carbonyl}-4-[2-(trifluoromethyl)phenyl]-4-piperidinol | 560 | 0.24 (1:2 Hexane/EtOAc) | 3.41 | 1 | 18 |
| 364 | 2-Cl-Ph | 4-Cl-Ph | H | 2-Cl-Ph | 1-{[2-(2-chlorophenyl)-1H-imidazol-4-yl]carbonyl}-4-(2-chlorophenyl)-4-piperidinol | 526 | 0.13 (1:2 Hexane/EtOAc) | 3.34 | 1 | 18 |
| 365 | 2-Cl-Ph | 4-Cl-Ph | H | 2-F-Ph | 1-{[2-(2-chlorophenyl)-1H-imidazol-4-yl]carbonyl}-4-(2-fluorophenyl)-4-piperidinol | 510 | 0.13 (1:2 Hexane/EtOAc) | 3.24 | 1 | 18 |

TABLE 13-continued

| Entry No. | $R^1$ | $R^2$ | $R^3$ | $R^{14}$ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 366 | 2-Cl-Ph | 4-Cl-Ph | H | 2-furyl | 1-{[2-(2-chlorophenyl)-1H-imidazol-4-yl]carbonyl}-4-(2-furyl)-4-piperidinol | 482 | 0.22 (1:2 Hexane/EtOAc) | 2.98 | 1 | 18 |
| 367 | 2-Cl-Ph | 4-Cl-Ph | Et | 2-furyl | 1-{[2-(2-chlorophenyl)-5-ethyl-1H-imidazol-4-yl]carbonyl}-4-(2-furyl)-4-piperidinol | 510 | 0.29 (1:2 Hexane/EtOAc) | 3.04 | 1 | 18 |
| 368 | 2-Cl-Ph | 4-Cl-Ph | H | 2-MeO-Ph | 1-{[2-(2-chlorophenyl)-1H-imidazol-4-yl]carbonyl}-4-(2-methoxyphenyl)-4-piperidinol | 522 | 0.22 (1:2 Hexane/EtOAc) | 3.23 | 1 | 18 |
| 369 | 2-Cl-Ph | 4-Cl-Ph | H | 2-pyridinyl | 1-{[2-(2-chlorophenyl)-1H-imidazol-4-yl]carbonyl}-4-(2-pyridinyl)-4-piperidinol | 493 | 0.05 (1:2 Hexane/EtOAc) | 2.26 | 1 | 18 |
| 370 | 2-Cl-Ph | 4-Cl-Ph | H | 2-thienyl | 1-{[2-(2-chlorophenyl)-1H-imidazol-4-yl]carbonyl}-4-(2-thienyl)-4-piperidinol | 498 | 0.22 (1:2 Hexane/EtOAc) | 3.11 | 1 | 18 |
| 371 | 2-Cl-Ph | 4-Cl-Ph | nPr | 2-thienyl | 1-{[2-(2-chlorophenyl)-5-propyl-1H-imidazol-4-yl]carbonyl}-4-(2-thienyl)-4-piperidinol | 540 | 0.41 (EtOAc) | 3.33 | 1 | 18 |
| 372 | 2-Cl-Ph | 4-Cl-Ph | Et | 2-thienyl | 1-{[2-(2-chlorophenyl)-5-ethyl-1H-imidazol-4-yl]carbonyl}-4-(2-thienyl)-4-piperidinol | 526 | 0.42 (EtOAc) | 3.20 | 1 | 18 |
| 373 | 2-Cl-Ph | 4-Cl-Ph | Et | 3-CF$_3$-4-Cl-Ph | 1-{[2-(2-chlorophenyl)-5-ethyl-1H-imidazol-4-yl]carbonyl}-4-[4-chloro-3-(trifluoromethyl)phenyl]-4-piperidinol | 622 | 0.47 (EtOAc) | 3.73 | 1 | 18 |

TABLE 13-continued

| Entry No. | R¹ | R² | R³ | R¹⁴ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 374 | 2-Cl-Ph | 4-Cl-Ph | nPr | 3-CF₃-4-Cl-Ph | 1-{[2-(2-chlorophenyl)-1-(4-chlorophenyl)-5-propyl-1H-imidazol-4-yl]carbonyl}-4-[4-chloro-3-(trifluoromethyl)phenyl]-4-piperidinol | 636 | 0.42 (EtOAc) | 3.82 | 1 | 18 |
| 375 | 2-Cl-Ph | 4-Cl-Ph | H | 3-CF₃O-Ph | 1-{[2-(2-chlorophenyl)-1-(4-chlorophenyl)-1H-imidazol-4-yl]carbonyl}-4-[3-(trifluoromethoxy)phenyl]-4-piperidinol | 576 | 0.38 (1:2 Hexane/EtOAc) | 3.37 | 1 | 18 |
| 376 | 2-Cl-Ph | 4-Cl-Ph | Et | 3-CF₃-Ph | 1-{[2-(2-chlorophenyl)-1-(4-chlorophenyl)-5-ethyl-1H-imidazol-4-yl]carbonyl}-4-[3-(trifluoromethyl)phenyl]-4-piperidinol | 588 | 0.46 (EtOAc) | 3.55 | 1 | 18 |
| 377 | 2-Cl-Ph | 4-Cl-Ph | nPr | 3-CF₃-Ph | 1-{[2-(2-chlorophenyl)-1-(4-chlorophenyl)-5-propyl-1H-imidazol-4-yl]carbonyl}-4-[3-(trifluoromethyl)phenyl]-4-piperidinol | 602 | 0.43 (EtOAc) | 3.65 | 1 | 18 |
| 378 | 2-Cl-Ph | 4-Cl-Ph | H | 3-Cl-Ph | 1-{[2-(2-chlorophenyl)-1-(4-chlorophenyl)-1H-imidazol-4-yl]carbonyl}-4-(3-chlorophenyl)-4-piperidinol | 526 | 0.18 (1:2 Hexane/EtOAc) | 3.39 | 1 | 18 |
| 379 | 2-Cl-Ph | 4-Cl-Ph | Et | 3-Cl-Ph | 1-{[2-(2-chlorophenyl)-1-(4-chlorophenyl)-5-ethyl-1H-imidazol-4-yl]carbonyl}-4-(3-chlorophenyl)-4-piperidinol | 554 | 0.42 (EtOAc) | 3.44 | 1 | 18 |
| 380 | 2-Cl-Ph | 4-Cl-Ph | nPr | 3-Cl-Ph | 1-{[2-(2-chlorophenyl)-1-(4-chlorophenyl)-5-propyl-1H-imidazol-4-yl]carbonyl}-4-(3-chlorophenyl)-4-piperidinol | 568 | 0.41 (EtOAc) | 3.58 | 1 | 18 |
| 381 | 2-Cl-Ph | 4-Cl-Ph | H | 3-F-4-CF₃-Ph | 1-{[2-(2-chlorophenyl)-1-(4-chlorophenyl)-1H-imidazol-4-yl]carbonyl}-4-[3-fluoro-4-(trifluoromethyl)phenyl]-4-piperidinol | 578 | 0.22 (1:2 Hexane/EtOAc) | 3.53 | 1 | 18 |
| 382 | 2-Cl-Ph | 4-Cl-Ph | H | 3-F-4-Cl-Ph | 1-{[2-(2-chlorophenyl)-1-(4-chlorophenyl)-1H-imidazol-4-yl]carbonyl}-4-(3-fluoro-4-chlorophenyl)-4-piperidinol | 544 | 0.25 (1:2 Hexane/EtOAc) | 3.36 | 1 | 18 |

TABLE 13-continued

| Entry No. | R¹ | R² | R³ | R¹⁴ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 383 | 2-Cl-Ph | 4-Cl-Ph | H | 3-F-Ph | 1-{[2-(2-chlorophenyl)-1-(4-chlorophenyl)-1H-imidazol-4-yl]carbonyl}-4-(3-fluorophenyl)-4-piperidinol | 510 | 0.24 (1:2 Hexane/EtOAc) | 3.19 | 1 | 18 |
| 384 | 2-Cl-Ph | 4-Cl-Ph | Et | 3-F-Ph | 1-{[2-(2-chlorophenyl)-1-(4-chlorophenyl)-5-ethyl-1H-imidazol-4-yl]carbonyl}-4-(3-fluorophenyl)-4-piperidinol | 538 | 0.43 (EtOAc) | 3.30 | 1 | 18 |
| 385 | 2-Cl-Ph | 4-Cl-Ph | nPr | 3-F-Ph | 1-{[2-(2-chlorophenyl)-1-(4-chlorophenyl)-5-propyl-1H-imidazol-4-yl]carbonyl}-4-(3-fluorophenyl)-4-piperidinol | 552 | 0.43 (EtOAc) | 3.41 | 1 | 18 |
| 386 | 2-Cl-Ph | 4-Cl-Ph | H | 6-methyl-2-pyridinyl | 1-{[2-(2-chlorophenyl)-1-(4-chlorophenyl)-1H-imidazol-4-yl]carbonyl}-4-(6-methyl-2-pyridinyl)-4-piperidinol | 507 | 0.32 (EtOAc) | 2.29 | 1 | 18 |
| 387 | 2-Cl-Ph | 4-Cl-Ph | Et | 6-methyl-2-pyridinyl | 1-{[2-(2-chlorophenyl)-1-(4-chlorophenyl)-5-ethyl-1H-imidazol-4-yl]carbonyl}-4-(6-methyl-2-pyridinyl)-4-piperidinol | 535 | 0.27 (1:2 Hexane/EtOAc) | 2.75 | 1 | 18 |
| 388 | 2-Cl-Ph | 4-Cl-Ph | H | 3-Me-4-MeO-Ph | 1-{[2-(2-chlorophenyl)-1-(4-chlorophenyl)-1H-imidazol-4-yl]carbonyl}-4-(4-methoxy-3-methylphenyl)-4-piperidinol | 537 | 0.20 (1:2 Hexane/EtOAc) | 3.25 | 1 | 18 |
| 389 | 2-Cl-Ph | 4-Cl-Ph | H | 3-MeO-Ph | 1-{[2-(2-chlorophenyl)-1-(4-chlorophenyl)-1H-imidazol-4-yl]carbonyl}-4-(3-methoxyphenyl)-4-piperidinol | 522 | 0.24 (1:2 Hexane/EtOAc) | 3.12 | 1 | 18 |
| 390 | 2-Cl-Ph | 4-Cl-Ph | H | 3-thienyl | 1-{[2-(2-chlorophenyl)-1-(4-chlorophenyl)-1H-imidazol-4-yl]carbonyl}-4-(3-thienyl)-4-piperidinol | 498 | 0.22 (1:2 Hexane/EtOAc) | 3.10 | 1 | 18 |
| 391 | 2-Cl-Ph | 4-Cl-Ph | H | 4,6-dimethyl-2-pyrimidinyl | 1-{[2-(2-chlorophenyl)-1-(4-chlorophenyl)-1H-imidazol-4-yl]carbonyl}-4-(4,6-dimethyl-2-pyrimidinyl)-4-piperidinol | 522 | 0.09 (EtOAc) | 2.55 | 1 | 18 |

TABLE 13-continued

| Entry No. | R¹ | R² | R³ | R¹⁴ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 392 | 2-Cl-Ph | 4-Cl-Ph | H | 4-CF₃O-Ph | 1-{[2-(2-chlorophenyl)-1-(4-chlorophenyl)-1H-imidazol-4-yl]carbonyl}-4-(4-trifluoromethoxyphenyl)-4-piperidinol | 576 | 0.18 (1:2 Hexane/EtOAc) | 3.48 | 1 | 18 |
| 393 | 2-Cl-Ph | 4-Cl-Ph | Et | 4-CF₃O-Ph | 1-{[2-(2-chlorophenyl)-1-(4-chlorophenyl)-5-ethyl-1H-imidazol-4-yl]carbonyl}-4-(4-trifluoromethoxyphenyl)-4-piperidinol | 604 | 0.39 (EtOAc) | 3.58 | 1 | 18 |
| 394 | 2-Cl-Ph | 4-Cl-Ph | nPr | 4-CF₃O-Ph | 1-{[2-(2-chlorophenyl)-1-(4-chlorophenyl)-5-propyl-1H-imidazol-4-yl]carbonyl}-4-(4-trifluoromethoxyphenyl)-4-piperidinol | 618 | 0.40 (EtOAc) | 3.70 | 1 | 18 |
| 395 | 2-Cl-Ph | 4-Cl-Ph | Et | 4-CF₃-Ph | 1-{[2-(2-chlorophenyl)-1-(4-chlorophenyl)-5-ethyl-1H-imidazol-4-yl]carbonyl}-4-(4-trifluoromethylphenyl)-4-piperidinol | 588 | 0.42 (EtOAc) | 3.55 | 1 | 18 |
| 396 | 2-Cl-Ph | 4-Cl-Ph | nPr | 4-CF₃-Ph | 1-{[2-(2-chlorophenyl)-1-(4-chlorophenyl)-5-propyl-1H-imidazol-4-yl]carbonyl}-4-(4-trifluoromethylphenyl)-4-piperidinol | 602 | 0.40 (EtOAc) | 3.66 | 1 | 18 |
| 397 | 2-Cl-Ph | 4-Cl-Ph | Et | 4-Cl-Ph | 1-{[2-(2-chlorophenyl)-1-(4-chlorophenyl)-5-ethyl-1H-imidazol-4-yl]carbonyl}-4-(4-chlorophenyl)-4-piperidinol | 554 | 0.42 (EtOAc) | 3.48 | 1 | 17 |
| 398 | 2-Cl-Ph | 4-Cl-Ph | nPr | 4-Cl-Ph | 1-{[2-(2-chlorophenyl)-1-(4-chlorophenyl)-5-propyl-1H-imidazol-4-yl]carbonyl}-4-(4-chlorophenyl)-4-piperidinol | 568 | 0.38 (EtOAc) | 3.57 | 1 | 17 |
| 399 | 2-Cl-Ph | 4-Cl-Ph | H | 4-F-Ph | 1-{[2-(2-chlorophenyl)-1-(4-chlorophenyl)-1H-imidazol-4-yl]carbonyl}-4-(4-fluorophenyl)-4-piperidinol | 510 | 0.25 (1:2 Hexane/EtOAc) | 3.18 | 1 | 17 |
| 400 | 2-Cl-Ph | 4-Cl-Ph | Et | 4-F-Ph | 1-{[2-(2-chlorophenyl)-1-(4-chlorophenyl)-5-ethyl-1H-imidazol-4-yl]carbonyl}-4-(4-fluorophenyl)-4-piperidinol | 538 | 0.36 (EtOAc) | 3.29 | 1 | 17 |

TABLE 13-continued

[Structure diagram with R¹, R², R³, R¹⁴ substituents on imidazole-piperidinol scaffold]

| Entry No. | R¹ | R² | R³ | R¹⁴ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 401 | 2-Cl-Ph | 4-Cl-Ph | nPr | 4-F-Ph | 1-{[2-(2-chlorophenyl)-1-(4-chlorophenyl)-5-propyl-1H-imidazol-4-yl]carbonyl}-4-(4-fluorophenyl)-4-piperidinol | 552 | 0.36 (EtOAc) | 3.41 | 1 | 17 |
| 402 | 2-Cl-Ph | 4-Cl-Ph | H | 5-methyl-2-pyridinyl | 1-{[2-(2-chlorophenyl)-1-(4-chlorophenyl)-1H-imidazol-4-yl]carbonyl}-4-(5-methyl-2-pyridinyl)-4-piperidinol | 507 | 0.15 (1:2 Hexane/EtOAc) | 2.31 | 1 | 18 |
| 403 | 2-Cl-Ph | 4-Cl-Ph | H | 4-MeO-Ph | 1-{[2-(2-chlorophenyl)-1-(4-chlorophenyl)-1H-imidazol-4-yl]carbonyl}-4-(4-methoxyphenyl)-4-piperidinol | 522 | 0.21 (1:2 Hexane/EtOAc) | 3.10 | 1 | 17 |
| 404 | 2-Cl-Ph | 4-Cl-Ph | H | 4-MeS-Ph | 1-{[2-(2-chlorophenyl)-1-(4-chlorophenyl)-1H-imidazol-4-yl]carbonyl}-4-[4-(methylsulfanyl)phenyl]-4-piperidinol | 538 | 0.18 (1:2 Hexane/EtOAc) | 3.29 | 1 | 18 |
| 405 | 2-Cl-Ph | 4-Cl-Ph | H | 4-methyl-2-pyridinyl | 1-{[2-(2-chlorophenyl)-1-(4-chlorophenyl)-1H-imidazol-4-yl]carbonyl}-4-(4-methyl-2-pyridinyl)-4-piperidinol | 521 | 0.18 (EtOAc) | 2.24 | 1 | 18 |
| 406 | 2-Cl-Ph | 4-Cl-Ph | H | Et | 1-{[2-(2-chlorophenyl)-1-(4-chlorophenyl)-1H-imidazol-4-yl]carbonyl}-4-ethyl-4-piperidinol | 444 | 0.15 (1:2 Hexane) | 2.86 | 1 | 17 |
| 407 | 2-Cl-Ph | 4-Cl-Ph | H | iso-butyl | 1-{[2-(2-chlorophenyl)-1-(4-chlorophenyl)-1H-imidazol-4-yl]carbonyl}-4-isobutyl-4-piperidinol | 472 | 0.10 (1:2 Hexane/EtOAc) | 3.24 | 1 | 17 |
| 408 | 2-Cl-Ph | 4-Cl-Ph | H | Me | 1-{[2-(2-chlorophenyl)-1-(4-chlorophenyl)-1H-imidazol-4-yl]carbonyl}-4-methyl-4-piperidinol | 431 | 0.08 (1:2 Hexane/EtOAc) | 2.69 | 1 | 17 |
| 409 | 2-Cl-Ph | 4-Cl-Ph | H | n-butyl | 1-{[2-(2-chlorophenyl)-1-(4-chlorophenyl)-1H-imidazol-4-yl]carbonyl}-4-butyl-4-piperidinol | 472 | 0.11 (1:2 Hexane/EtOAc) | 3.84 | 1 | 18 |
| 410 | 2-Cl-Ph | 4-Cl-Ph | H | n-pentyl | 1-{[2-(2-chlorophenyl)-1-(4-chlorophenyl)-1H-imidazol-4-yl]carbonyl}-4-pentyl-4-piperidinol | 486 | 0.30 (EtOAc) | 3.45 | 1 | 17 |

TABLE 13-continued

| Entry No. | R¹ | R² | R³ | R¹⁴ | IUPAC name | MS m/z (MH + 1) | TLC Rf (solvent) | HPLC RT (min) | HPLC method | Synthesis Method of Ex. No. |
|---|---|---|---|---|---|---|---|---|---|---|
| 411 | 2-Cl-Ph | 4-Cl-Ph | H | Ph | 1-{[2-(2-chlorophenyl)-1-(4-chlorophenyl)-1H-imidazol-4-yl]carbonyl}-4-phenyl-4-piperidinol | 474 | | 3.03 | 2 | 10, 11, 12 |
| 412 | 2,4-Cl₂-Ph | 4-MeO-Ph | H | Ph | 1-{[2-(2-chlorophenyl)-1-(4-methoxyphenyl)-1H-imidazol-4-yl]carbonyl}-4-phenyl-4-piperidinol | 522 | | 3.55 | 2 | 10, 11, 12 |
| 413 | 2,4-Cl₂-Ph | 4-Cl-Ph | H | Ph | 1-{[2-(2,4-dichlorophenyl)-1-(4-chlorophenyl)-1H-imidazol-4-yl]carbonyl}-4-phenyl-4-piperidinol | 526 | | 3.33 | 2 | 10, 11, 12 |
| 414 | 2-Me-Ph | 4-Cl-Ph | H | Ph | 1-{[2-(2-methylphenyl)-1-(4-chlorophenyl)-1H-imidazol-4-yl]carbonyl}-4-phenyl-4-piperidinol | 472 | | 2.90 | 2 | 10, 11, 12 |
| 415 | 2,4-Cl₂-Ph | 4-F-Ph | H | Ph | 1-{[2-(2,4-dichlorophenyl)-1-(4-fluorophenyl)-1H-imidazol-4-yl]carbonyl}-4-phenyl-4-piperidinol | 509 | | 3.03 | 2 | 10, 11, 12 |
| 416 | 2-Cl-Ph | 4-Cl-Ph | H | 4-Br-Ph | 1-{[2-(2-chlorophenyl)-1H-imidazol-4-yl]carbonyl}-4-(4-bromophenyl)-4-piperidinol | 570 | | 3.14 | 2 | 10, 11, 12 |
| 417 | 2-Cl-Ph | 4-Cl-Ph | H | benzyl | 1-{[2-(2-chlorophenyl)-1-(4-chlorophenyl)-1H-imidazol-4-506yl]carbonyl}-4-benzyl-4-piperidinol | 506 | | 2.98 | 2 | 10, 11, 12 |
| 418 | 2-Cl-Ph | 4-Cl-Ph | H | 3-CF₃-4-Cl-Ph | 1-{[2-(2-chlorophenyl)-1-(4-chlorophenyl)-1H-imidazol-4-yl]carbonyl}-4-[4-chloro-3-(trifluoromethyl)phenyl]-4-piperidinol | 594 | | 3.38 | 2 | 10, 11, 12 |
| 419 | 2-Cl-Ph | 4-Cl-Ph | H | 4-Cl-Ph | 1-{[2-(2-chlorophenyl)-1-(4-chlorophenyl)-1H-imidazol-4-yl]carbonyl}-4-(4-chlorophenyl)-4-piperidinol | 526 | | 3.11 | 2 | 10, 11, 12 |
| 420 | 2-Cl-Ph | 4-Cl-Ph | H | 3-CF₃-Ph | 1-{[2-(2-chlorophenyl)-1-(4-chlorophenyl)-1H-imidazol-4-yl]carbonyl}-4-[3-(trifluromethyl)phenyl]-4-piperidinol | 560 | | 3.17 | 2 | 10, 11, 12 |

TABLE 14

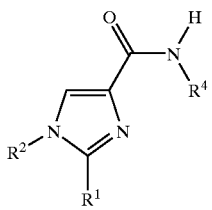

| Entry No. | R¹ | R² | R⁴ | IUPAC name | MS m/z [MH+] | TLC Rf (solvent) | HPLC RT (min.) | HPLC method | Synthesis Method of Ex. No. |
|---|---|---|---|---|---|---|---|---|---|
| 421 | 2-Cl-Ph | 3-pyridinyl | cyclohexyl | 2-(2-chlorophenyl)-N-cyclohexyl-1-(3-pyridinyl)-1H-imidazole-4-carboxamide | 381.2 | 0.23(4% MeOH in CH₂Cl₂) | 2.71 | 1 | 8 |
| 422 | 2-Cl-3-pyridinyl | 4-F-Ph | 1-piperidinyl | 2-(2-chloro-3-pyridinyl)-1-(4-fluorophenyl)-N-(1-piperidinyl)-1H-imidazole-4-carboxamide | 400.3 | 0.19 (EtOAc) | 2.32 | 1 | 10,11, 12 |
| 423 | 4-CF₃-3-pyridinyl | 4-Cl-Ph | 1-piperidinyl | 1-(4-chlorophenyl)-N-(1-piperidinyl) 2-[4-(trifluoromethyl)-3-pyridinyl]-1H-imidazole-4-carboxamide | 450.3 | 0.45(10% MeOH in EtOAc) | 2.58 | 1 | 8 |
| 424 | 3-Me-2-pyridinyl | 4-Cl-Ph | 1-piperidinyl | 1-(4-chlorophenyl)-2-(3-methyl-2-pyridinyl)-N-(1-piperidinyl)-1H-imidazole-4-carboxamide | 396.3 | 0.25 (EtOAc) | 2.27 | 1 | 8 |
| 425 | 3-Me-4-pyridinyl | 4-Cl-Ph | 1-piperidinyl | 1-(4-chlorophenyl)-2-(3-methyl-4-pyridinyl)-N-(1-piperidinyl)-1H-imidazole-4-carboxamide | 396.3 | 0.30(2% MeOH in EtOAc) | 2.10 | 1 | 13, 14 |
| 426 | 4-CF₃-3-pyridinyl | 4-Cl-Ph | 2-CF₃-anillino | 1-(4-chlorophenyl)-N'-[2-(trifluoromethyl)phenyl]-2-[4-(trifluoromethyl)-3-pyridinyl]-1H-imidazole-4-carbohydrazide hydrochloride | 525 | | 3.65 | 1 | 10,11, 12 |
| 427 | 3-Me-2-thienyl | 4-Cl-Ph | 1-piperidinyl | 1-(4-chlorophenyl)-2-(3-methyl-2-thienyl)-N-(1-piperidinyl)-1H-imidazole-4-carboxamide | 401.2 | 0.22(67% EtOAc in hexane) | 2.8 | 1 | 6 |
| 428 | 2-furyl | 4-Cl-Ph | 1-piperidinyl | 1-(4-chlorophenyl)-2-(2-furyl)-N-(1-piperidinyl)-1H-imidazole-4-carboxamide | 371.2 | 0.27(80% EtOAc in hexane) | 2.57 | 1 | 6 |
| 429 | 2-Cl-Ph | 5-t-Bu-3-isoxazolyl | 1-piperidinyl | 1-(5-tert-butyl-3-isoxazolyl)-2-(2-chlorophenyl)-N-(1-piperidinyl)-1H-imidazole-4-carboxamide | 428.2 | 0.12(1:1 EtOAc/ hexane) | 3.06 | 1 | 13, 14 |
| 430 | 2-Cl-Ph | 5-t-Bu-3-isoxazolyl | cyclohexyl | 1-(5-tert-butyl-3-isoxazolyl)-2-(2-chlorophenyl)-N-cyclohexyl-1H-imidazole-4-carboxamide | 427.2 | 0.39(1:1 EtOAc/ hexane) | 3.68 | 1 | 13, 14 |
| 431 | 2-Cl-Ph | 5-t-Bu-3-isoxazolyl | 2-(S)-benzyloxy-1-(S)-cyclohexyl | N-[(1S, 2S)-2-(benzyloxy)cyclohexyl]-1-(5-tert-chlorophenyl)-1H-imidazole-4-carboxamide | 533.1 | 0.34(1:1 EtOAc/ hexane) | 3.89 | 1 | 13, 14 |
| 432 | 2-Cl-Ph | 3-quinolinyl | 1-piperidinyl | 2-(2-chlorophenyl)-N-(1-piperidinyl) 1-(3-quinolinyl)-1H-imidazole-4-carboxamide | 432.2 | 0.11 (RtOAc) | 2.61 | 1 | 13, 14 |
| 433 | 2-Cl-Ph | 3-quinolinyl | cyclohexyl | 2-(2-chlorophenyl)-N-cyclohexyl-1-(3-quinolinyl)-1H-imidazole-4-carboxamide | 431.2 | 0.44 (EtOAc) | 3.23 | 1 | 13, 14 |
| 434 | 2-Cl-Ph | 3-quinolinyl | 2-(S)-benzyloxy-1-(S)-cyclohexyl | N-[(1S, 2S)-2-(benzyloxy)cyclohexyl]-2-(2-chlorophenyl)-1-(3-quinolinyl)-1H-imidazole-4-carboxamide | 537.1 | 0.46 (EtOAc) | 3.51 | 1 | 13, 14 |
| 435 | 2-Cl-Ph | isoxazolyl isoxazolyl | 2-(S)-hydroxy-1-(S)-cyclohexyl | 1-(5-tert-butyl-3-isoxazolyl)-2-(2-chlorophenyl)-N-[(1S, 2S)-2-hydroxycyclohexyl]-1H-imidazole-4 carboxamide | 443.2 | 0.43 (EtOAc) | 3.07 | 1 | 35 |
| 436 | 2-Cl-Ph | 3-quinolinyl | 2-(S)-hydroxy-1-(S)-cyclohexyl | 2-(2-chlorophenyl)-N-[(1S, 2S)-2-hydroxycyclohexyl]-1-(3-quinolinyl) 1H-imidazole-4-carboxamide | 447.2 | 0.19 (EtOAC) | 2.65 | 1 | 35 |
| 437 | 2-Me-4-thiazolyl | 4-Cl-Ph | 1-piperidinyl | 1-(4-chlorophenyl)-2-(2-methyl-1,3-thiazol-4-yl)-N-(1-piperidinyl)-1H-imidazole-4-carboxamide | 402.2 | 0.21 (EtOAc) | 2.41 | 1 | 6 |
| 438 | 1-naphthyl | 4-Cl-Ph | 1-piperidinyl | 1-(4-chlorophenyl)-2-(1-naphthyl)-N-(1-piperidinyl)-1H-imidazole-4-carboxamide | 431.2 | 0.42 (EtOAc) | 3.06 | 1 | 6 |

TABLE 14-continued

| Entry No. | R¹ | R² | R⁴ | IUPAC name | MS m/z [MH+] | TLC Rf (solvent) | HPLC RT (min.) | HPLC method | Synthesis Method of Ex. No. |
|---|---|---|---|---|---|---|---|---|---|
| 439 | 2-Cl-Ph | 1,3-thiazol-2-yl | 1-piperidinyl | 2-(2-chlorophenyl)-N-(1-piperidinyl) 1-(1,3-thiazol-2-yl)-1H-imidazole-4-carboxamide | 388.1 | 0.27 (EtOAc) | 2.46 | 1 | 13, 14 |
| 440 | 2-Cl-Ph | 1,3-thiazol-2-yl | cyclohexyl | 2-(2-chlorophenyl)-N-cyclohexyl-1-(1,3-thiazol-2-yl)-1H-imidazoie-4-carboxamide | 387.1 | 0.52 (EtOAc) | 3.15 | 1 | 13, 14 |

TABLE 15

| Entry No. | R¹ | R² | R³ | R⁴ | IUPAC name | MS m/z [MH⁺] | TLC Rf (solvent) | HPLC RT (min.) | HPLC method | Synthesis Method of Ex. No. |
|---|---|---|---|---|---|---|---|---|---|---|
| 441 | 2-Cl-Ph | 4-Cl-benzyl | Me | cyclohexyl | 1-(4-chlorobenzyl)-2-(2-chlorophenyl)-N-cyclohexyl-5-methyl-1H-imidazole-4-carboxamide | 442.2 | | 2.65 | 1 | 8 |
| 442 | 2-Cl-Ph | 1-piperidinyl | H | 1-piperidinyl | 2-(2-chlorophenyl)-N,1-di(1-piperidinyl)-1H-imidazole-4-carboxamide | 388.3 | 0.10(1:1 EtOAc/hexane) | 2.76 | 1 | 10,11,12 |
| 443 | 2-Cl-Ph | 1-piperidinyl | H | cyclohexyl | 2-(2-chlorophenyl)-N-cyclohexyl-1-(1-piperidinyl)-1H-imidazole-4-carboxamide | 387.3 | 0.38(1:1 EtOAc/hexane) | 3.44 | 1 | 10,11,12 |
| 444 | 2-Cl-Ph | 4-morpholinyl | H | 1-piperidinyl | 2-(2-chlorophenyl)-1-(4-morpholinyl)-N-(1-piperidinyl) 1H-imidazole-4-carboxamide | 390.4 | 0.13 (EtOAc) | 2.21 | 1 | 10,11,12 |
| 445 | 2-Cl-Ph | 4-morpholinyl | H | cyclohexyl | 2-(2-chlorophenyl)-N-cyclohexyl-1-(4-morpholinyl)-1H-imidazole-4-carboxamide | 389.3 | 0.13(1:1 EtOAc/hexane) | 2.87 | 1 | 10,11,12 |
| 446 | 2-Cl-Ph | cyclohexyl | H | 1-piperidinyl | 2-(2-chlorophenyl)-1-cyclohexyl-N-(1-piperidinyl)-1H-imidazole-4-carboxamide | 387.4 | 0.18 EtOAC | 2.60 | 1 | 10,11,12 |
| 447 | 2-Cl-Ph | cyclohexyl | H | cyclohexyl | 2-(2-chlorophenyl)-N,1-dicyclohexyl-1H-imidazole-4-carboxamide | 386.4 | 0.30(1:1 EtOAc/hexane) | 3.23 | 1 | 10,11,12 |
| 448 | 2-Cl-Ph | 4-Me-cyclohexyl | H | cyclohexyl | 2-(2-chlorophenyl)-N-cyclohexyl-1-(4-methylcyclohexyl)-1H-imidazole-4-carboxamide | 400.4 | 0.38(1:1 EtOAc/hexane) | 3.43 | 1 | 10,11,12 |
| 449 | 2-Cl-Ph | 4-Me-cyclohexyl | H | 1-piperidinyl | 2-(2-chlorophenyl)-1-(4-methylcyclohexyl)-N-(1-piperidinyl)-1H-imidazole-4-carboxamide | 401.4 | 0.32 (EtOAc) | 2.83 | 1 | 10,11,12 |

TABLE 15-continued

TABLE 15-continued

| Entry No. | R¹ | R² | R³ | R⁴ | IUPAC name | MS m/z [MH⁺] | TLC Rf (solvent) | HPLC RT (min.) | HPLC method | Synthesis Method of Ex. No. |
|---|---|---|---|---|---|---|---|---|---|---|
| 450 | 2-Me-1-propyl | 4-Cl-Ph | H | 1-piperidinyl | 1-(4-chlorophenyl)-2-isobutyl-N-(1-piperidinyl)-1H-imidazole-4-carboxamide | 361.1 | 0.28 (EtOAc) | 2.43 | 1 | 6 |
| 451 | 2-Cl-Ph | 4-F-benzyl | Et | 1-piperidinyl | 2-(2-chlorophenyl)-5-ethyl-1-(4-fluorobenzyl)-N-(1-piperidinyl)-1H-imidazole-4-carboxamide | 441.2 | 0.21 (EtOAc) | 2.75 | 1 | 13,14 |
| 452 | 2-Cl-Ph | 4-MeO-PhCO | Et | 1-piperidinyl | 2-(2-chlorophenyl)-5-ethyl-1-(4-methoxybenzoyl)-N-(1-piperidinyl)-1H-imidazole-4-carboxamide | 467.2 | 0.24(1:1 EtOAc/hexane) | 3.01 | 1 | 6 |
| 453 | benzyl | 4-Cl-Ph | H | 1-piperidinyl | 2-benzyl-1-(4-chlorophenyl)-N-(1-piperidinyl)-1H-imidazole-4-carboxamide | 395.2 | 0.26 (EtOAc) | 2.75 | 1 | 6 |
| 454 | n-hexyl | 4-Cl-Ph | H | 1-piperidinyl | 1-(4-chlorophenyl)-2-hexyl-N-(1-piperidinyl)-1H-imidazole-4 carboxamide | 389.2 | 0.30 (EtOAC) | 3 | 1 | 6 |

TABLE 16

| Entry No. | R¹⁰ | IUPAC name | MS m/z [MH+] | LC-MS RT (min) | HPLC method | Synthesis Method of Ex. No. |
|---|---|---|---|---|---|---|
| 455 | Me | N-{[2-(2-chlorophenyl)-1-(4-chlorophenyl) 1H-imidazol-4-yl]carbonyl}methanesulfonamide | 410 | 2.70 | 2 | 16 |
| 456 | 4-CF₃-Ph | N-{[2-(2-chlorophenyl)-1-(4-chlorophenyl) 1H-imidazol-4-yl]carbonyl}-4-(trifluoromethyl)benzenesulfonamide | 540 | 3.55 | 2 | 16 |
| 457 | Ph | N-{[2-(2-chlorophenyl)-1-(4-chlorophenyl) 1H-imidazol-4-yl]carbonyl}benzenesulfonamide | 472 | 3.14 | 2 | 16 |
| 458 | 4-MeO-Ph | N-{[2-(2-chlorophenyl)-1-(4-chlorophenyl) 1H-imidazol-4-y]carbonyl}-4-methoxybenzenesulfonamide | 502 | 3.22 | 2 | 16 |

TABLE 17

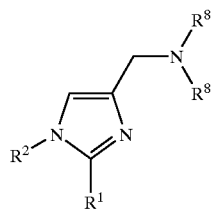

| Entry No. | R¹ | R² | R⁸ | R⁹ | IUPAC name | MS m/z [MH⁺] | TLC Rf (solvent) | HPLC RT (min) | HPLC method | Synthesis Method of Ex. No. |
|---|---|---|---|---|---|---|---|---|---|---|
| 459 | 2-MeO-Ph | 4-Cl-Ph | H | 4-F-benzyl | N-{[1-(4-chlorophenyl)-2-(2-methoxyphenyl)-1H-imidazol-4-yl]methyl}-N-(4-4 fluorobenzyl)amine | 422 | 0.3(88% EtOAc in hexane) | 2.48 | 1 | 33 |
| 460 | 2,4-Cl₂-Ph | 4-F-Ph | Me | cyclohexyl | N-cyclohexyl-N-{[2-(2,4-dichlorophenyl)-1-4-fluorophenyl)-1H-imidazol-4-yl]methyl}-N methylamine | 432 | 0.19(10% MeOH in hexane) | 2.65 | 1 | 34 |
| 461 | 2,4-Cl₂-Ph | 4-Cl-Ph | H | 4-F-benzyl | N-{[1-(4-chlorophenyl)-2-(2,4-dichlorophenyl)-1H-imidazol-4-yl]methyl}-N-(4-fluorobenzyl)amine | 460 | 0.33(10% MeOH in EtOAc) | 2.88 | 1 | 33 |
| 462 | 2,4-Cl₂-Ph | 4-Cl-Ph | H | 4-CF₃-benzyl | N-{[1-(4-chlorophenyl)-2-(2,4-dichlorophenyl)-1H-imidazol-4-yl]methyl}-N-[4-(trifluoromethyl)benzyl]amine | 510 | 0.33(5% MeOH in EtOAc) | 3.03 | 1 | 33 |
| 463 | 2,4-Cl₂-Ph | 4-Cl-Ph | H | trans-2-OH-cyclphexyl | trans-2-({[1-(4-chlorophenyl)-2-(2,4-dichlorophenyl)-1H-imidazol-4-yl]methyl)amino)cyclohexanol | 451 | 0.3(33% MeOH in EtOAc) | 2.69 | 1 | 33 |
| 464 | 2,4-Cl₂-Ph | 4-Cl-Ph | H | cyclohexyl | N-{[1-(4-chlorophenyl)-2-(2,4-dichlorophenyl)-1H-imidazol-4-yl]methyl}-N-cyclohexyamine | 434 | 0.31(25% MeOH in EtOAc) | 2.83 | 1 | 33 |
| 465 | 2,4-Cl₂-Ph | 4-Cl-Ph | H | 4-(4-Me-Ph)-1-piperazinyl | 1-{[1-(4-chlorophenyl)-2-(2,4-dichlorophenyl)-1H-imidazol-4-yl]methyl}-4-(4-methylphenyl)piperazine bis(trifluoroacetate) | 511 | | 2.94 | 1 | 34 |
| 466 | 2-Cl-Ph | 4-Cl-Ph | H | cyclohexyl | N-{[2-(2-chlorophenyl)-1-(4-chlorophenyl)-1H-imidazol-4-yl]methyl}-N-cyclohexylamine | 401 | 0.35(50% EtOAc in MeOH) | 2.32 | 1 | 33 |

TABLE 18

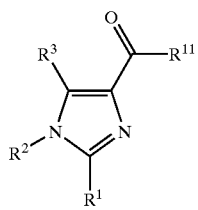

| Entry No. | R¹ | R² | R³ | R¹¹ | IUPAC Name | MS m/z (MH+) | TLC Rf (solvent) | HPLC RT (min) (LC-MS) | Synthesis Method of Ex. No. |
|---|---|---|---|---|---|---|---|---|---|
| 467 | 2-Cl-Ph | 4-Cl-Ph | Et | 2-thienyl | [2-(2-chlorophenyl)-1-(4-chlorophenyl)-5-ethyl-1H-imidazol-4-yl](2-thienyl)methanone | 427 | 0.13(1:5 EtOAc/Hexane) | 3.93 | 31 |
| 468 | 2-Cl-Ph | 4-Cl-Ph | H | n-propyl | 1-[2-(2-chlorophenyl)-1-(4-chlorophenyl)-1H-imidazol-4-yl]-1-butanone | 359 | 0.49(1:1 EtOAc/Hexane) | 3.30 | 29 |
| 469 | 2-Cl-Ph | 4-Cl-Ph | H | 1-methylpropyl | 1-[2-(2-chlorophenyl)-1-(4-chlorophenyl)-1H-imidazol-4-yl]-3-methyl-1-butanone | 373 | 0.53(1:1 EtOAc/Hexane) | 3.47 | 29 |
| 470 | 2-Cl-Ph | 4-Cl-Ph | H | 1-methylpropyl | 1-[2-(2-chlorophenyl)-1-(4-chlorophenyl)-1H-imidazol-4-yl]-2-methyl-1-butanone | 373 | 0.56(1:1 EtOAc/Hexane) | 3.47 | 29 |
| 471 | 2-Cl-Ph | 4-Cl-Ph | H | n-pentyl | 1-[2-(2-chlorophenyl)-1-(4-chlorophenyl)-1H-imidazol-4-yl]-1-hexanone | 387 | 0.56(1:1 EtOAc/Hexane) | 3.71 | 29 |
| 472 | 2-Cl-Ph | 4-Cl-Ph | H | cyclopentyl | [2-(2-chlorophenyl)-1-(4-chlorophenyl)-1H-imidazol-4-yl](cyclopentyl)methanone | 385 | 0.54(1:1 EtOAc/Hexane) | 3.54 | 29 |

TABLE 18-continued

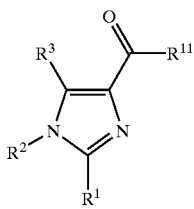

| Entry No. | $R^1$ | $R^2$ | $R^3$ | $R^{11}$ | IUPAC Name | MS m/z (MH+) | TLC Rf (solvent) | HPLC RT (min) (LC-MS) | Synthesis Method of Ex. No. |
|---|---|---|---|---|---|---|---|---|---|
| 473 | 2-Cl-Ph | 4-Cl-Ph | H | cyclohexyl | [2-(2-chlorophenyl)-1-(4-chlorophenyl)-1H-imidazol-4-yl](cyclohexyl)methanone | 399 | 0.56(1:1 EtOAc/Hexane) | 3.71 | 29 |
| 474 | 2-Cl-Ph | 4-Cl-Ph | H | 4-F-Ph | [2-(2-chlorophenyl)-1-(4-chlorophenyl)-1H-imidazol-4-yl](4-fluorophenyl)methanone | 411 | 0.58(1:1 EtOAc/Hexane) | 3.57 | 29 |
| 475 | 2-Cl-Ph | 4-Cl-Ph | H | 4-Cl-Ph | (4-chlorophenyl)[2-(2-chlorophenyl)-1-(4-chlorophenyl)-1H-imidazol-4-yl]methanone | 427 | 0.37(1:3 EtOAc/Hexane) | 3.83 | 29 |
| 476 | 2-Cl-Ph | 4-Cl-Ph | H | 2-MeO-Ph | [2-(2-chlorophenyl)-1-(4-chlorophenyl)-1H-imidazol-4-yl](3-methoxyphenyl)methanone | 423 | 0.20(1:3 EtOAc/Hexane) | 3.52 | 29 |
| 477 | 2-Cl-Ph | 4-Cl-Ph | H | 4-MeO-Ph | [2-(2-chlorophenyl)-1-(4-chlorophenyl)-1H-imidazol-4-yl](4-methoxyphenyl)methanone | 423 | 0.18(1:3 EtOAc/Hexane) | 3.51 | 29 |
| 478 | 2-Cl-Ph | 4-Cl-Ph | H | Et | 1-[2-(2-chlorophenyl)-1-(4-chlorophenyl)-1H-imidazol-4-yl]-1-propanone | 345 | 0.42(1:1 EtOAc/Hexane) | 3.10 | 29 |
| 479 | 2-Cl-Ph | 4-Cl-Ph | H | benzyl | 1-[2-(2-chlorophenyl)-1-(4-chlorophenyl)-1-H-imidazol-4-yl]-2-phenylethanone | 407 | 0.51(1:1 EtOAc/Hexane) | 3.54 | 29 |
| 480 | 2-Cl-Ph | 4-Cl-Ph | H | Ph | [2-(2-chlorophenyl)-1-(4-chlorophenyl)-1H-imidazol-4-yl](phenyl)methanone | 393 | 0.5(1:1 EtOAc/Hexane) | 3.48 | 29 |

Evaluation of Biological Activity
Evaluation of Compound's Efficacy on the Reduction of Food Intake in Lean Overnight Fasted Rats
Fasted-Refed Acute Feeding Assay The purpose of this protocol is to determine the effect of a single dose of an unknown compound on food consumption of lean overnight fasted rats. The fasted-refed rat model is frequently used in the field of obesity to identify compounds with potential for anorectic effects. This animal model has been successfully used in the identification and characterization of the efficacy profile of compounds that are or have been used in the management of body weight in obese humans (see, e.g., Balvet et al., Gen. Pharmacol. 13:293–297, 1982; Grignaschi et al., Br. J. Pharmacol. 127:1190–1194, 1999; McTavish and Heel, Drug 43:713–733, 1992; Rowland et al., Life Sci. 36:2295–2300, 1985).

A typical study includes 60–80 male rats (n=10/treatment group) with an average body weight of approximately 280 g. Rats are kept in standard animal rooms under controlled temperature and humidity and a 12/12 light dark cycle. Rats are single-housed in suspended cages with a mesh floor. Water and food are continuously available unless the animals are being fasted for the study.

The vehicle test: The rats are grouped based upon their performance on a vehicle test. The vehicle test is performed between 2 and 7 days before the efficacy test. The rats are fasted overnight during the dark phase (total of approx. 16–18 hrs). The animal is dosed with 0.5 mL deionized water. One hour after dosing, pre-weighed food jars are returned to the animal home cage. The rats are allowed one hour of feeding time. After 1 hour, the spillage is returned to the food jar and the amount of food consumed is determined. The rats are assigned to groups so that the mean and standard error of the mean of 1-hour food consumption are similar between groups.

The efficacy test: The rats are fasted overnight during the dark phase (total of approx. 16–18 hr). The animal is dosed with an assigned treatment (2 mg/ml). One hour after dosing, pre-weighed food jars are returned to the cage. Food intake is recorded 30, 60, 90, 180, and 240 minutes post-food return. At each time point, spillage is returned to the food jar and then the food jars are weighed. The amount of food consumed is determined for each time point. Difference between treatment group is determined using appropriate statistical analysis.

Compounds of the present invention were found to be active in this fasted-refed acute feeding assay. For example, when the imidazole derivative 2-(2-chlorophenyl)-1-(4-chlorophenyl)-N-[(1S,2S)-2-hydroxycyclohexyl]-1H-imidazole-4-carboxamide was dosed at 10 mg/kg p.o., food consumption was reduced (relative to the food consumption observed for the vehicle control group) by 34% to 62% when measured at time points from 30 to 240 minutes. Likewise, when the imidazole derivative 2-(2-chlorophenyl)-1-(4-chlorophenyl)-N'-[4-(trifluoromethyl)phenyl]-1H-imidazole-4-carbohydrazide hydrochloride was dosed at 10 mg/kg p.o., food consumption was reduced (relative to the food consumption observed for the vehicle control group) by 31% to 53% when measured at time points from 30 to 240 minutes.

Evaluation of Compound's Efficacy on the Reduction of Body Weight and Food and Water Consumption in Obese Zucker fa/fa Rats
Chronic Feeding Assay The purpose of this protocol is to determine the effect of chronic administration of an unknown compound on body weight and food and water consumption in obese Zucker fa/fa rats. Obese Zucker fa/fa rats are frequently used in the determination of compound efficacy in the reduction of body weight. This animal model has been successfully used in the identification and characterization of the efficacy profile of compounds that are or have been used in the management of body weight in obese humans (see, e.g., Al-Barazanji et al., Obes Res. 8:317–323, 2000; Assimacopoulos-Jeannet et al., Am. J. Physiol. 260(2 Pt 2):R278–283, 1991; Dryden et al., Horm. Metab. Res. 31:363–366, 1999; Edwards and Stevens, Pharmacol. Biochem. Behav. 47:865–872, 1994; Grinker et al., Pharmacol. Biochem. Behav. 12:265–275, 1980).

A typical study includes 60–80 male Zucker fa/fa (n=10/treatment group) with an average body weight of approximately 550 g. Rats are kept in standard animal rooms under controlled temperature and humidity and a 12/12 light dark cycle. Water and food are continuously available. Rats are single-housed in large rat shoeboxes containing grid floor. Animals are adapted to the grid floors and sham-dosed with study vehicle for at least four days before the recording of two-days baseline measurement of body weight and 24-hr food and water consumption. Rats are assigned to one of 6–8 treatment groups based upon their body weight on baseline. The groups are set up so that the mean and standard error of the mean of body weight were similar.

Animals are orally gavaged (2 mL/kg) daily before the dark phase of the LD/cycle for a pre-determined number of days (typically 6–14 days) with their assigned dose/compound. At this time, body weight, food and water consumption are measured. On the final day, animals are euthanized by $CO_2$ inhalation, and the body weight is measured.

Compounds of this invention were found to be active in this chronic feeding assay. For example, when the imidazole derivative 2-(2-chlorophenyl)-1-(4-chlorophenyl)-N-[(1S, 2S)-2-hydroxycyclohexyl]-1H-imidazole-4-carboxamide was dosed once a day at 10 mg/kg p.o., on day 6 of treatment the increase in body weight from baseline was approximately 2.4%, representing approximately 50% reduction in body weight gain as compared to the vehicle control group, where an approximately 4.6% increase in body weight from baseline was observed. Likewise, when the imidazole derivative 2-(2-chlorophenyl)-1-(4-chlorophenyl)-N'-[4-(trifluoromethyl)phenyl]-1H-imidazole-4-carbohydrazide hydrochloride was dosed once a day at 10 mg/kg p.o., on day 6 of treatment the increase in body weight from baseline was approximately 1.8%, representing approximately 60% reduction in body weight gain as compared to the vehicle control group, where an approximately 4.6% increase in body weight from baseline was observed.

Measurement of Brain Exposure

Male obese Zucker fa/fa rats were administered compounds, typically at 10 mg/kg p.o., and then brains were collected at 2 hours post-dosing for determination of brain concentration. Brains were weighed and homogenized with 4 mL 10 mM ammonium acetate buffer (pH 3), and the brain tissue homogenate samples were extracted via protein precipitation with acetonitrile. Samples were vortexed, centrifuged, and analyzed by liquid chromatography utilizing mass spectrometer selective detection (LC/MS/MS) using the heated nebulizer interface. Samples were quantitated using weighted ($1/x^2$) linear internal standard calibration curve. For example, when 1-(4-chlorophenyl)-2-(2-chlorophenyl)-N-(1-piperidinyl)-5-butyl-1H-imidazole-4-carboxamide was dosed at 10 mg/kg p.o., a brain homogenate exposure level of approximately 200 nM was determined; when 2-(2-chlorophenyl)-1-(4-chlorophenyl)-5-ethyl-N-[(1S,2S)-2-hydroxycyclohexyl]-1H-imidazole-4-carboxamide was dosed at 10 mg/kg p.o., a brain homogenate exposure level of approximately 200 nM was determined.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 14 days. At this point, the animals are bled again by eye or tail vein and blood glucose levels are determined. In each case, glucose levels are measured with a Glucometer Elite XL (Bayer Corporation, Elkhart, Ind.).

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 8 days. The animals are then bled again by eye or tail vein, and serum triglyceride levels are determined. In each case, triglyceride levels are measured using a Technicon Axon Autoanalyzer (Bayer Corporation, Tarrytown, N.Y.).

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 days, and then bled again on day 8. Plasma is analyzed for HDL-cholesterol using the Synchron Clinical System (CX4) (Beckman Coulter, Fullerton, Calif.).

Method for Measuring Total Cholesterol, HDL-Cholesterol, Triglycerides, and Glucose Levels In another in vivo assay, obese monkeys are bled, then orally dosed once daily with vehicle or test compound for 4 weeks, and then bled again. Serum is analyzed for total cholesterol, HDL-cholesterol, triglycerides, and glucose using the Synchron Clinical System (CX4) (Beckman Coulter, Fullerton, Calif.). Lipoprotein subclass analysis is performed by NMR spectroscopy as described by Oliver et al., (Proc. Natl. Acad. Sci. USA 98:5306–5311, 2001).

Method for Measuring an Effect on Cardiovascular Parameters

Cardiovascular parameters (e.g., heart rate and blood pressure) are also evaluated. SHR rats are orally dosed once daily with vehicle or test compound for 2 weeks. Blood pressure and heart rate are determined using a tail-cuff method as described by Grinsell et al., (Am. J. Hypertens. 13:370–375, 2000). In monkeys, blood pressure and heart rate are monitored as described by Shen et al., (J. Pharmacol. Exp. Therap. 278:1435–1443, 1996).

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149–153, 1990; Morris, J. Neurosci. Methods 11:47–60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442–448, 2002; Campbell et al., Exp. Clin. Psychopharmacol. 8:312–25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior. Tests are conducted every two days, and the order of the administration of the test compound doses is controlled.

Pharmaceutical Compositions

Based on the above tests, or other well known assays used to determine the efficacy for treatment of conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered may generally range from about 0.001 mg/kg to about 200 mg/kg, and preferably from about 0.01 mg/kg to about 200 mg/kg body weight per day. A unit dosage may contain from about 0.05 mg to about 1500 mg of active ingredient, and may be administered one or more times per day. The daily dosage for administration by injection, including intravenous, intramuscular, subcutaneous, and parenteral injections, and use of infusion techniques may be from about 0.01 to about 200 mg/kg. The daily rectal dosage regimen may be from 0.01 to 200 mg/kg of total body weight. The transdermal concentration may be that required to maintain a daily dose of from 0.01 to 200 mg/kg.

Of course, the specific initial and continuing dosage regimen for each patient will vary according to the nature and severity of the condition as determined by the attending diagnostician, the activity of the specific compound employed, the age of the patient, the diet of the patient, time of administration, route of administration, rate of excretion of the drug, drug combinations, and the like. The desired mode of treatment and number of doses of a compound of the present invention or a pharmaceutically acceptable salt thereof may be ascertained by those skilled in the art using conventional treatment tests.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular condition or disease. Therefore, the present invention includes pharmaceutical compositions which are comprised of a pharmaceutically acceptable carrier and a pharmaceutically effective amount of a compound identified by the methods described herein, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of a compound is that amount which produces a result or exerts an influence on the particular condition being treated. The compounds identified by the methods described herein may be administered with a pharmaceutically-acceptable carrier using any effective conventional dosage unit forms, including, for example, immediate and timed release preparations, orally, parenterally, topically, or the like.

For oral administration, the compounds may be formulated into solid or liquid preparations such as, for example, capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, and (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil; or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring and coloring agents.

The compounds of this invention may also be administered parenterally, that is, subcutaneously, intravenously, intramuscularly, or interiperitoneally, as injectable dosages of the compound in a physiologically acceptable diluent with a pharmaceutical carrier which may be a sterile liquid or mixture of liquids such as water, saline, aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol, ethers such as poly(ethyleneglycol) 400; an oil; a fatty acid; a fatty acid ester or glyceride; or an acetylated fatty acid glyceride with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention may typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions may be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. For example, direct techniques for administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, incorporated herein by reference.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

Commonly used pharmaceutical ingredients which may be used as appropriate to formulate the composition for its intended route of administration include: acidifying agents, for example, but are not limited to, acetic acid, citric acid, fumaric acid, hydrochloric acid, nitric acid; and alkalinizing agents such as, but are not limited to, ammonia solution, ammonium carbonate, diethanolamine, monoethanolamine, potassium hydroxide, sodium borate, sodium carbonate, sodium hydroxide, triethanolamine, trolamine.

Other pharmaceutical ingredients include, for example, but are not limited to, adsorbents (e.g., powdered cellulose and activated charcoal); aerosol propellants (e.g., carbon dioxide, $CCl_2F_2$, $F_2ClC-CClF_2$ and $CClF_3$); air displacement agents (e.g., nitrogen and argon); antifungal preservatives (e.g., benzoic acid, butylparaben, ethylparaben, methylparaben, propylparaben, sodium benzoate); antimicrobial preservatives (e.g., benzalkonium chloride, benzethonium chloride, benzyl alcohol, cetylpyridinium chloride, chlorobutanol, phenol, phenylethyl alcohol, phenylmercuric nitrate and thimerosal); antioxidants (e.g., ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite); binding materials (e.g., block polymers, natural and synthetic rubber, polyacrylates, polyurethanes, silicones and styrene-butadiene copolymers); buffering agents (e.g., potassium metaphosphate, potassium phosphate monobasic, sodium acetate, sodium citrate anhydrous and sodium citrate dihydrate); carrying agents (e.g., acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (e.g., edetate disodium and edetic acid); colorants (e.g., FD&C Red No. 3, FD&C Red No. 20, FD&C Yellow No. 6, FD&C Blue No. 2, D&C Green No. 5, D&C Orange No. 5, D&C Red No. 8, caramel and ferric oxide red); clarifying agents (e.g., bentonite); emulsifying agents (but are not limited to, acacia, cetomacrogol, cetyl alcohol, glyceryl monostearate, lecithin, sorbitan monooleate, polyethylene 50 stearate); encapsulating agents (e.g., gelatin and cellulose acetate phthalate); flavorants (e.g., anise oil, cinnamon oil, cocoa, menthol, orange oil, peppermint oil and vanillin); humectants (e.g., glycerin, propylene glycol and sorbitol); levigating agents (e.g., mineral oil and glycerin); oils (e.g., arachis oil, mineral oil, olive oil, peanut oil, sesame oil and vegetable oil); ointment bases (e.g., lanolin, hydrophilic ointment, polyethylene glycol ointment, petrolatum, hydrophilic petrolatum, white ointment, yellow ointment, and rose water ointment); penetration enhancers (transdermal delivery) (e.g., monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (e.g., diethyl phthalate and glycerin); solvents (e.g., alcohol, corn oil, cottonseed oil, glycerin, isopropyl alcohol, mineral oil, oleic acid, peanut oil, purified water, water for injection, sterile water for injection and sterile water for irrigation); stiffening agents (e.g., cetyl alcohol, cetyl esters wax, microcrystalline wax, paraffin, stearyl alcohol, white wax and yellow wax); suppository bases (e.g., cocoa butter and polyethylene glycols (mixtures)); surfactants (e.g., benzalkonium chloride, nonoxynol 10, oxtoxynol 9, polysorbate 80, sodium lauryl sulfate and sorbitan monopalmitate); suspending agents (e.g., agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening e.g., aspartame, dextrose, glycerin, mannitol, propylene glycol, saccharin sodium, sorbitol and sucrose); tablet anti-adherents (e.g., magnesium stearate and talc); tablet binders (e.g., acacia, alginic acid, carboxymethylcellulose sodium, compressible sugar, ethylcellulose, gelatin, liquid glucose, methylcellulose, povidone and pregelatinized starch); tablet and capsule diluents (e.g., dibasic calcium phosphate, kaolin, lactose, mannitol, microcrystalline cellulose, powdered cellulose, precipitated calcium carbonate, sodium carbonate, sodium phosphate, sorbitol and starch); tablet coating agents (e.g., liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (e.g., dibasic calcium phosphate); tablet disintegrants (e.g., alginic acid, carboxymethylcellulose calcium, microcrystalline cellulose, polacrillin potassium, sodium alginate, sodium starch glycollate and starch); tablet glidants (e.g., colloidal silica, corn starch and talc); tablet lubricants (e.g., calcium stearate, magnesium stearate, mineral oil, stearic acid and zinc stearate); tablet/capsule opaquants (e.g., titanium dioxide); tablet polishing agents (e.g., carnuba wax and white wax); thickening agents (e.g., beeswax, cetyl alcohol and paraffin); tonicity agents (e.g., dextrose and sodium chloride); viscosity increasing agents (e.g., alginic acid, bentonite, carbomers, carboxymethylcellulose sodium, methylcellulose, povidone, sodium alginate and tragacanth); and wetting agents (e.g., heptadecaethylene oxycetanol, lecithins, polyethylene sorbitol monooleate, polyoxyethylene sorbitol monooleate, and polyoxyethylene stearate).

The compounds identified by the methods described herein may be administered as the sole pharmaceutical agent or in combination with one or more other pharmaceutical agents where the combination causes no unacceptable adverse effects. For example, the compounds of this invention can be combined with known anti-obesity, or with known antidiabetic or other indication agents, and the like, as well as with admixtures and combinations thereof.

The compounds identified by the methods described herein may also be utilized, in free base form or in compositions, in research and diagnostics, or as analytical reference standards, and the like. Therefore, the present invention includes compositions which are comprised of an inert carrier and an effective amount of a compound identified by the methods described herein, or a salt or ester thereof. An inert carrier is any material which does not interact with the compound to be carried and which lends support, means of conveyance, bulk, traceable material, and the like to the compound to be carried. An effective amount of compound is that amount which produces a result or exerts an influence on the particular procedure being performed.

Formulations suitable for subcutaneous, intravenous, intramuscular, and the like; suitable pharmaceutical carriers; and techniques for formulation and administration may be prepared by any of the methods well known in the art (see, e.g., Remington's Pharmaceutical Sciences, Mack Publishing Co., Easton, Pa., 20$^{th}$ edition, 2000)

The following examples are presented to illustrate the invention described herein, but should not be construed as limiting the scope of the invention in any way.

Capsule Formulation

A capsule formula is prepared from:

| | |
|---|---|
| Compound of this invention | 40 mg |
| Starch | 109 mg |
| Magnesium stearate | 1 mg |

The components are blended, passed through an appropriate mesh sieve, and filled into hard gelatin capsules.

Tablet Formulation

A tablet is prepared from:

| | |
|---|---|
| Compound of this invention | 25 mg |
| Cellulose, microcrystaline | 200 mg |
| Colloidal silicon dioxide | 10 mg |
| Stearic acid | 5.0 mg |

The ingredients are mixed and compressed to form tablets. Appropriate aqueous and non-aqueous coatings may be applied to increase palatability, improve elegance and stability or delay absorption.

Sterile IV Solution

A 5 mg/ml solution of the desired compound of this invention is made using sterile, injectable water, and the pH is adjusted if necessary. The solution is diluted for administration to 1–2 mg/ml with sterile 5% dextrose and is administered as an IV infusion over 60 minutes.

Intramuscular Suspension

The following intramuscular suspension is prepared:

| | |
|---|---|
| Compound of this invention | 50 mg/ml |
| Sodium carboxymethylcellulose | 5 mg/ml |
| TWEEN 80 | 4 mg/ml |
| Sodium chloride | 9 mg/ml |
| Benzyl alcohol | 9 mg/ml |

The suspension is administered intramuscularly.

Hard Shell Capsules

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

What is claimed:

1. A compound 1-(4-chlorophenyl)-2-(2-chlorophenyl)-N-(1-piperidinyl)-5-ethyl-1H-imidazole-4-carboxamide, and pharmaceutical salts thereof.

2. A pharmaceutical composition comprising an effective amount of the compound of claim 1, or a pharmaceutically acceptable salt thereof, in combination with a pharmaceutically acceptable carrier.

3. A pharmaceutical composition comprising an effective amount of the compound of claim 1, or a pharmaceutically acceptable salt thereof, in combination with a pharmaceutically acceptable carrier and one or more agents for the treatment of diabetes.

4. The pharmaceutical composition of claim 3, wherein said agent for the treatment of diabetes is selected from the group consisting of insulin, biguanidines, sulfonylureas, insulin secretagogues, α-glycosidase inhibitors, and $\beta_3$-adrenoreceptor agonists.

5. A pharmaceutical composition comprising an effective amount of the compound of claim 1, or a pharmaceutically acceptable salt thereof, in combination with a pharmaceutically acceptable carrier and one or more agents selected from the group consisting of HMG CoA reductase inhibitor, bile acid binding agent, fibric acid derivative, and agent that regulates hypertension.

6. A pharmaceutical composition comprising an effective amount of the compound of claim 1, or a pharmaceutically acceptable salt or ester thereof, in combination with a pharmaceutically acceptable carrier and one or more agents selected from the group consisting of agents that modulate thermogenesis, lipolysis, gut motility, fat absorption, and satiety.

7. A composition comprising an effective amount of the compound of claim 1, or a salt thereof, in combination with an inert carrier.

8. A method of treating obesity comprising the step of administering to a patient in need thereof a pharmaceutically effective amount of the compound of claim 1.

* * * * *